(12) United States Patent
Cheung et al.

(10) Patent No.: US 9,090,559 B2
(45) Date of Patent: Jul. 28, 2015

(54) ANTIVIRAL COMPOUNDS

(71) Applicant: Hoffmann-La Roche Inc., Nutley, NJ (US)

(72) Inventors: Adrian Wai-Hing Cheung, Glen Rock, NJ (US); Ryan Craig Schoenfeld, Basking Ridge, NJ (US); Weiya Yun, Warren, NJ (US); Shu-Hai Zhao, Cupertino, CA (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/376,336

(22) PCT Filed: Feb. 21, 2013

(86) PCT No.: PCT/EP2013/053409
§ 371 (c)(1),
(2) Date: Aug. 1, 2014

(87) PCT Pub. No.: WO2013/124335
PCT Pub. Date: Aug. 29, 2013

(65) Prior Publication Data
US 2015/0005283 A1 Jan. 1, 2015

Related U.S. Application Data

(60) Provisional application No. 61/602,687, filed on Feb. 24, 2012.

(51) Int. Cl.
| C07D 215/02 | (2006.01) |
| C07D 211/06 | (2006.01) |
| C07D 207/16 | (2006.01) |
| C07D 401/12 | (2006.01) |
| C07D 413/04 | (2006.01) |
| C07D 211/60 | (2006.01) |
| C07D 403/06 | (2006.01) |

(52) U.S. Cl.
CPC ............ *C07D 207/16* (2013.01); *C07D 211/60* (2013.01); *C07D 401/12* (2013.01); *C07D 403/06* (2013.01); *C07D 413/04* (2013.01)

(58) Field of Classification Search
CPC ...................................................... C07D 207/16
USPC .................................................. 546/166, 206
See application file for complete search history.

(56) References Cited

U.S. PATENT DOCUMENTS 8,729,098 B2 * 5/2014 Gagliardi et al. ............. 514/314

FOREIGN PATENT DOCUMENTS

| WO | WO 00/09543 | 2/2000 |
| WO | WO 2010/015815 | 2/2010 |

OTHER PUBLICATIONS

Ding et al. Journal of Medicianl Chemistry, 2005, 48, 3171-3181.*
International Search Report dated Apr. 11, 2013 from the European Patent Office citing two foreign references for Internat'l Appln. No. PCT/EP2013/053409 filed Feb. 21, 2013.
Written Opinion of the International Searching Authority dated Apr. 11, 2013 for Internat'l Appln. No. PCT/EP2013/053409 filed Feb. 21, 2013.

* cited by examiner

*Primary Examiner* — Nizal Chandrakumar

(57) ABSTRACT

The present invention provides compounds, compositions and methods for the treatment of hepatitis C virus (HCV) infection. Also disclosed are pharmaceutical compositions containing such compounds and methods for using these compounds in the treatment of HCV infection.

22 Claims, No Drawings

ANTIVIRAL COMPOUNDS

This application is a National Stage Application of PCT/EP2013/053409 filed Feb. 21, 2013, which claims priority from Provisional Patent Application No. 61/602,687 filed on Feb. 24, 2012, which applications are hereby incorporated by reference herein in their entirety.

FIELD OF THE INVENTION

The present invention provides compounds of Formula I and certain derivatives thereof, which are useful as inhibitors of hepatitis C virus (HCV) replication, and for the treatment of hepatitis C infection.

Hepatitis C virus (HCV) infection is a major health problem that leads to chronic liver disease, such as cirrhosis and hepatocellular carcinoma, in a substantial number of infected individuals. Current standard treatments for HCV infection is a combination of pegylated interferon-α (PEG-IFNα) with ribavirin (RBV) that leading to a sustained viral response (SVR) in ~80% in patients infected with HCV genotypes 2 and 3, and between 40-50% in those with genotype 1 (Ghany M G et al. 2009. Hepatology 49(4): 1335-1374). Systemic administration of IFN is associated with numerous side effects, and significant efforts are currently being pursued to develop IFNα-free therapy, mostly by directly targeting HCV proteins involved in viral replication (direct-acting antivirals, DAAs). While DAAs such as NS3 protease and NS5A inhibitors have been shown to increase SVR when given with PEG-IFNα, these classes of compounds induced rapid selection of resistant virus in vivo (Soriano V et al. 2011. Antimicrob. Chemother. 66: 1673-1686). Thus, other alternatives for HCV treatment are to develop drugs that has higher barrier to resistance such as nucleos(t)ide analog of viral NS5B polymerase, or those target host factor(s) required for virus replication, or combination of both. Host factors are well conserved and therefore, drugs interfering with such factors are expected to be active across different genotypes and less likely to induce development of resistant virus (Buhler S & Bartenschlager R. 2012. Liver Int. doi: 10.1111/j.1478-3231).

The development and success of DAA is attributed to the robust cell culture system that supports self-replicating HCV RNA. This system, so-called replicon, contains part of HCV genome that is required for viral replication. The replicon system provided the first functional cell-based platform for screening of antiviral agents targeting HCV RNA replication and for validation of compounds directed against recombinant viral enzymes such as NS3 protease. Likewise, replicon system can be used to discover novel compounds that act on host targets required for HCV replication.

There is a clear and long-felt need to develop effective therapeutics for treatment of HCV infection. Specifically, there is a need to develop compounds that are useful for treating HCV-infected patients and compounds that selectively inhibit HCV viral replication.

SUMMARY OF THE INVENTION

The application provides a compound of Formula I

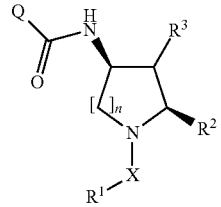

wherein:
n is 1 or 2;
Q is phenyl or naphthalene substituted with one or more Q';
  Q' is hydroxyl, lower alkyl, or halo;
$R^1$ is lower alkyl, cycloalkyl, phenyl, or heterocycloalkyl;
$R^2$ is $—C(=O)OR^{2'}$, $—C=O)R^{2'}$, $—C(=O)ON(R^{2'})_2$, monocyclic or bicyclic heteroaryl, optionally substituted with one or more $R^{2'}$;
  each $R^{2'}$ is independently H, lower alkyl or heterocycloalkyl;
$R^3$ is H or lower alkyl; and
X is $CH_2$ or $C(=O)$;
or a pharmaceutically acceptable salt thereof.

The application provides a method for treating a Hepatitis C Virus (HCV) infection comprising administering to a patient in need thereof a therapeutically effective amount of a compound of Formula I.

The application provides a composition comprising a compound of Formula and a pharmaceutically acceptable excipient.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

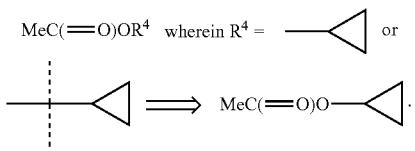

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—☐—C(—OH)=CH—), amide/imidic acid (—C(=O)—NH—☐—C(—OH)=N—) and amidine (—C(=NR)—NH—☐—C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diazaspiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "$PCy_3$", refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" or "hydroxyl lower alkyl", as used herein denotes an alkyl radical, or lower alkyl radical, as herein defined, wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "carboxy" or "carboxyl" refers to a —$CO_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of HCV NS5A

The application provides a compound of Formula I

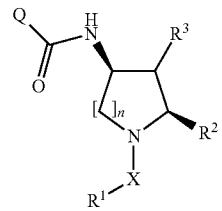

wherein:
n is 1 or 2;
Q is phenyl or naphthalene substituted with one or more Q';
Q' is hydroxyl, lower alkyl, or halo;
$R^1$ is lower alkyl, cycloalkyl, phenyl, or heterocycloalkyl;
$R^2$ is —C(=O)O$R^{2'}$, —C(=O)ON($R^{2'}$)$_2$, monocyclic or bicyclic heteroaryl, optionally substituted with one or more $R^{2'}$;
each $R^{2'}$ is independently H, lower alkyl or heterocycloalkyl;
$R^3$ is H or lower alkyl; and
X is $CH_2$ or C(=O);
or a pharmaceutically acceptable salt thereof.

The application provides a compound of Formula I, wherein n is 1.

The application provides a compound of Formula I, wherein $R^3$ is H.

The application provides a compound of Formula I, wherein $R^3$ is H and n is 1.

The application provides a compound of Formula I, wherein X is $CH_2$.

The application provides a compound of Formula I, wherein X is $CH_2$ and $R^3$ is H.

The application provides a compound of Formula I, wherein X is $CH_2$ and n is 1.

The application provides a compound of Formula I, wherein X is $CH_2$, $R^3$ is H, and n is 1.

The application provides a compound of Formula I, wherein $R^2$ is —C(=O)N($R^{2'}$)$_2$.

The application provides a compound of Formula I, wherein $R^2$ is —C(=O)N($R^{2'}$)$_2$ and n is 1.

The application provides a compound of Formula I, wherein $R^2$ is —C(=O)N($R^{2'}$)$_2$ and $R^3$ is H.

The application provides a compound of Formula I, wherein $R^2$ is —C(=C)N($R^{2'}$)$_2$ and X is $CH_2$.

The application provides a compound of Formula I, wherein $R^2$ is —C(=O)N($R^{2'}$)$_2$, X is $CH_2$, $R^3$ is H, and n is 1.

The application provides a compound of Formula I, wherein $R^2$ is monocyclic or bicyclic heteroaryl, optionally substituted with one or more $R^{2'}$.

The application provides a compound of Formula I, wherein $R^2$ is —C(=O)O$R^{2'}$.

The application provides a compound of Formula I, wherein $R^{2'}$ is lower alkyl.

The application provides a compound of Formula I, wherein $R^2$ is —C(=O)O$R^{2'}$ and $R^{2'}$ is lower alkyl.

The application provides a compound of Formula I, wherein $R^2$ is monocyclic or bicyclic heteroaryl, optionally substituted with one or more $R^{2'}$, X is $CH_2$, $R^3$ is H, and n is 1.

The application provides a compound of Formula I, wherein $R^2$ is —C(=O)O$R^{2'}$, X is $CH_2$, $R^3$ is H, and n is 1.

The application provides a compound of Formula I, wherein $R^{2'}$ is lower alkyl, X is $CH_2$, $R^3$ is H, and n is 1.

The application provides a compound of Formula I, wherein $R^2$ is —C(=O)O$R^{2'}$, $R^{2'}$ is lower alkyl, X is $CH_2$, $R^3$ is H, and n is 1.

The application provides a compound of Formula I, wherein $R^1$ is lower alkyl or cycloalkyl.

The application provides a compound of Formula I, wherein R' is cyclohexyl.

The application provides a compound of Formula I, wherein R' is lower alkyl or cycloalkyl, $R^2$ is —C(=O)O$R^{2'}$, $R^{2'}$ is lower alkyl, X is $CH_2$, $R^3$ is H, and n is 1.

The application provides a compound of Formula I, wherein $R^1$ is cyclohexyl, $R^2$ is —C(=O)O$R^{2'}$, $R^{2'}$ is lower alkyl, X is $CH_2$, $R^3$ is H, and n is 1.

The application provides a compound of Formula I, wherein n is 1.

The application provides a compound of Formula I, wherein $R^3$ is H.

The application provides a compound of Formula I, wherein $R^3$ is H and n is 1.

The application provides a compound of Formula I, wherein X is $CH_2$.

The application provides a compound of Formula I, wherein X is $CH_2$ and $R^3$ is H.

The application provides a compound of Formula I, wherein X is $CH_2$ and n is 1.

The application provides a compound of Formula I, wherein X is $CH_2$, $R^3$ is H, and n is 1.

The application provides a compound of Formula I, wherein $R^2$ is —C(=O)N($R^{2'}$)$_2$.

The application provides a compound of Formula I, wherein $R^2$ is —C(=O)N($R^{2'}$)$_2$ and n is 1.

The application provides a compound of Formula I, wherein $R^2$ is —C(=O)N($R^{2'}$)$_2$ and $R^3$ is H.

The application provides a compound of Formula I, wherein $R^2$ is —C(=O)N($R^{2'}$)$_2$ and X is $CH_2$.

The application provides a compound of Formula I, wherein $R^2$ is —C(=O)N($R^{2'}$)$_2$, X is $CH_2$, $R^3$ is H, and n is 1.

The application provides a compound of Formula I, wherein $R^2$ is monocyclic or bicyclic heteroaryl, optionally substituted with one or more $R^{2'}$.

The application provides a compound of Formula I, wherein $R^2$ is —C(=O)O$R^{2'}$.

The application provides a compound of Formula I, wherein $R^{2'}$ is lower alkyl.

The application provides a compound of Formula I, wherein $R^2$ is —C(=O)O$R^{2'}$ and $R^{2'}$ is lower alkyl.

The application provides a compound of Formula I, wherein $R^2$ is monocycle or bicyclic heteroaryl, optionally substituted with one or more $R^{2'}$, X is $CH_2$, $R^3$ is H, and n is 1.

The application provides a compound of Formula I, wherein $R^2$ is —C(=O)O$R^{2'}$, X is $CH_2$, $R^3$ is H, and n is 1.

The application provides a compound of Formula I, wherein $R^{2'}$ is lower alkyl, X is $CH_2$, $R^3$ is H, and n is 1.

The application provides a compound of Formula I, wherein $R^2$ is —C(=O)O$R^{2'}$, $R^{2'}$ is lower alkyl, X is $CH_2$, $R^3$ is H, and n is 1.

The application provides a compound of Formula I, wherein $R^1$ is lower alkyl or cycloalkyl.

The application provides a compound of Formula I, wherein $R^1$ is cyclohexyl.

The application provides a compound of Formula I, wherein $R^1$ is lower alkyl or cycloalkyl, $R^2$ is —C(=O)O$R^{2'}$, $R^{2'}$ is lower alkyl, X is $CH_2$, $R^3$ is H, and n is 1.

The application provides a compound of Formula I, wherein $R^1$ is cyclohexyl, $R^2$ is —C(=O)O$R^{2'}$, $R^{2'}$ is lower alkyl, X is $CH_2$, $R^3$ is H, and n is 1.

The application provides a compound selected from the group consisting of (2S,4S)-1-Cyclohexylmethyl-4-[(1-hydroxy-naphthalene-2-carbonyl)-amino]-pyrrolidine-2-carboxylic acid tert-butyl ester;

(2S,4S)-1-(3,3-Dimethyl-butyl)-4-[(1-hydroxy-naphthalene-2-carbonyl)-amino]-pyrrolidine-2-carboxylic acid methyl ester;

(2S,4R)-1-Cyclohexylmethyl-4-[(1-hydroxy-naphthalene-2-carbonyl)-amino]-piperidine-2-carboxylic acid ethyl ester;

(2S,4S)-1-Cyclohexylmethyl-4-[(1-hydroxy-naphthalene-2-carbonyl)-amino]-pyrrolidine-2-carboxylic acid ethyl ester;

1-Hydroxy-naphthalene-2-carboxylic acid ((3S,5S)-5-benzooxazol-2-yl-1-cyclohexylmethyl-pyrrolidin-3-yl)-amide;

(2S,4R)-1-Cyclohexylmethyl-4-[(1-hydroxy-naphthalene-2-carbonyl)-amino]-piperidine-2-carboxylic acid methyl ester;

1-Hydroxy-naphthalene-2-carboxylic acid [(3S,5S)-1-cyclohexylmethyl-5-(5-methyl-oxazol-2-yl)-pyrrolidin-3-yl]-amide;

1-Hydroxy-naphthalene-2-carboxylic acid [(3S,5S)-1-cyclohexylmethyl-5-(5-phenyl-oxazol-2-yl)-pyrrolidin-3-yl]-amide;

1-Hydroxy-naphthalene-2-carboxylic acid ((3S,5S)-1-cyclohexylmethyl-5-oxazol-2-yl-pyrrolidin-3-yl)-amide;

(2S,4S)-1-Cyclohexylmethyl-4-[(1-hydroxy-naphthalene-2-carbonyl)-amino]-pyrrolidine-2-carboxylic acid methyl ester;

(2S,4S)-1-Benzyl-4-[(1-hydroxy-naphthalene-2-carbonyl)-amino]-pyrrolidine-2-carboxylic acid methyl ester;

(2S,4S)-1-Cyclopentylmethyl-4-[(1-hydroxy-naphthalene-2-carbonyl)-amino]-pyrrolidine-2-carboxylic acid ethyl ester;

(2S,4S)-1-Cyclohexylmethyl-4-[(1-hydroxy-naphthalene-2-carbonyl)-amino]pyrrolidine-2-carboxylic acid benzylamide;

(2S,4S)-1-Cyclohexanecarbonyl-4-[(1-hydroxy-naphthalene-2-carbonyl)-amino]-pyrrolidine-2-carboxylic acid ethyl ester;

(2S,4S)-1-Cyclohexylmethyl-4-[(1-hydroxy-naphthalene-2-carbonyl)-amino]-pyrrolidine-2-carboxylic acid isopropylamide;

(2S,4S)-1-Cyclohexylmethyl-4-[(1-hydroxy-naphthalene-2-carbonyl)-amino]-pyrrolidine-2-carboxylic acid propylamide;
(2S,4S)-1-Cyclobutylmethyl-4-[(1-hydroxy-naphthalene-2-carbonyl)-amino]-pyrrolidine-2-carboxylic acid ethyl ester;
(2S,4S)-1-Cyclohexylmethyl-4-[(1-hydroxy-naphthalene-2-carbonyl)-amino]-pyrrolidine-2-carboxylic acid ethylamide;
(2S,4R)-1-Cyclohexylmethyl-4-[(1-hydroxy-naphthalene-2-carbonyl)-amino]-piperidine-2-carboxylic acid ethylamide;
(2R,4S)-1-Cyclohexylmethyl-4-[(1-hydroxy-naphthalene-2-carbonyl)-amino]-pyrrolidine-2-carboxylic acid methyl ester;
(2S,4S)-1-Cyclohexylmethyl-4-[(1-hydroxy-naphthalene-2-carbonyl)-amino]-2-methyl-pyrrolidine-2-carboxylic acid methyl ester;
(2S,4S)-4-[(1-Hydroxy-naphthalene-2-carbonyl)-amino]-1-isobutyl-pyrrolidine-2-carboxylic acid ethyl ester;
(2S,4S)-4-[(1-Amino-naphthalene-2-carbonyl)-amino]-1-cyclohexylmethyl-pyrrolidine-2-carboxylic acid methyl ester;
(2S,4S)-1-Cyclohexylmethyl-4-[(8-hydroxy-quinoline-7-carbonyl)-amino]-pyrrolidine-2-carboxylic acid ethyl ester;
(2S,4S)-1-Cyclohexylmethyl-4-[(1-hydroxy-naphthalene-2-carbonyl)-amino]-pyrrolidine-2-carboxylic acid amide;
1-Hydroxy-naphthalene-2-carboxylic acid [(3S,5S)-1-cyclohexylmethyl-5-(pyrrolidine-1-carbonyl)-pyrrolidin-3-yl]-amide;
(2S,4R)-1-Benzyl-4-[(1-hydroxy-naphthalene-2-carbonyl)-amino]-pyrrolidine-2-carboxylic acid ethyl ester;
(2S,4R)-1-Cyclohexylmethyl-4-[(1-hydroxy-naphthalene-2-carbonyl)-amino]-pyrrolidine-2-carboxylic acid methyl ester; and
1-Hydroxy-naphthalene-2-carboxylic acid [(3S,5S)-5-(azetidine-1-carbonyl)-1-cyclohexylmethyl-pyrrolidin-3-yl]-amide.

The application provides a method for treating a Hepatitis C Virus (HCV) infection comprising administering to a patient in need thereof a therapeutically effective amount of a compound of Formula I.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

The application provides a method for inhibiting replication of HCV in a cell comprising administering a compound of any one of Formula I.

The application provides a composition comprising a compound of Formula I and a pharmaceutically acceptable excipient.

The application provides a use of the compound of Formula I in the manufacture of a medicament for the treatment of HCV.

The application provides a compound, composition, or method as described herein.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I.

TABLE I

| # | Structure | Nomenclature | Example # |
| --- | --- | --- | --- |
| I-1 | 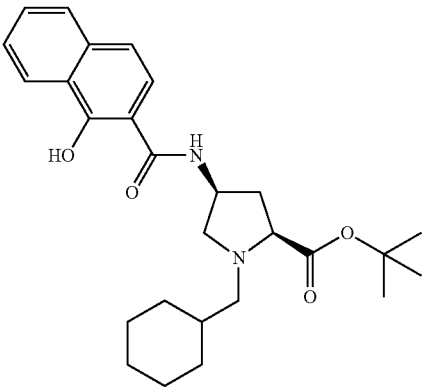 [SMILES: CC(C)(C)OC(=O)[C@@H]1C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-pyrrolidine-2-carboxylic acid tert-butyl ester | 9 |

TABLE I-continued

| # | Structure | Nomenclature | Example # |
|---|---|---|---|
| I-2 | 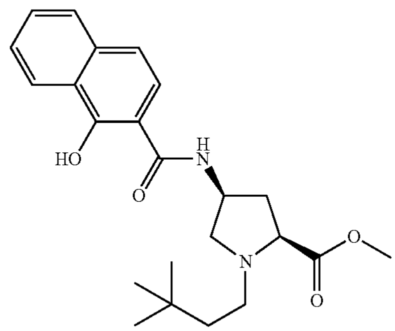 [SMILES: COC(=O)[C@@H]1C[C@H](NC(=O)c2ccc3ccccc3c2O)CN1CCC(C)(C)C] | (2S,4S)-1-(3,3-Dimethyl-butyl)-4-[(1-hydroxy-naphthalene-2-carbonyl)-amino]-pyrrolidine-2-carboxylic acid methyl ester | 3 |
| I-3 | 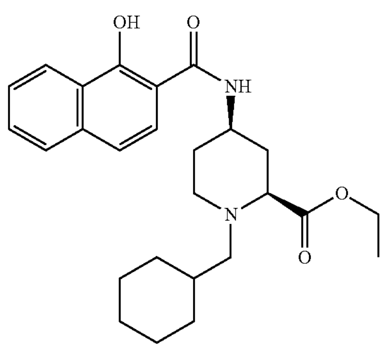 [SMILES: CCOC(=O)[C@@H]1C[C@H](NC(=O)c2ccc3ccccc3c2O)CCN1CC1CCCCC1] | (2S,4R)-1-Cyclohexylmethyl-4-[(1-hydroxy-naphthalene-2-carbonyl)-amino]-piperidine-2-carboxylic acid ethyl ester | 24 |
| I-4 | 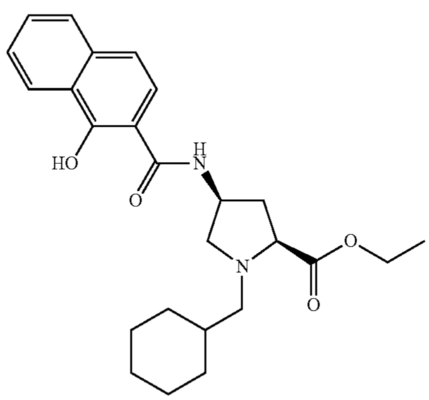 [SMILES: CCOC(=O)[C@@H]1C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-pyrrolidine-2-carboxylic acid ethyl ester | 8 |
| I-5 | 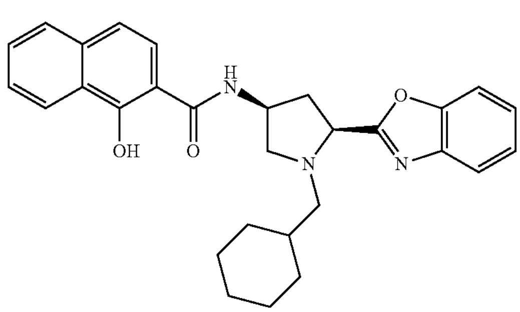 [SMILES: O=C(N[C@H]1C[C@@H](c2nc3ccccc3o2)N(CC2CCCCC2)C1)c1ccc2ccccc2c1O] | 1-Hydroxy-naphthalene-2-carboxylic acid ((3S,5S)-5-benzooxazol-2-yl-1-cyclohexylmethyl-pyrrolidin-3-yl)-amide | 29 |

TABLE I-continued

| # | Structure | Nomenclature | Example # |
|---|---|---|---|
| I-6 | 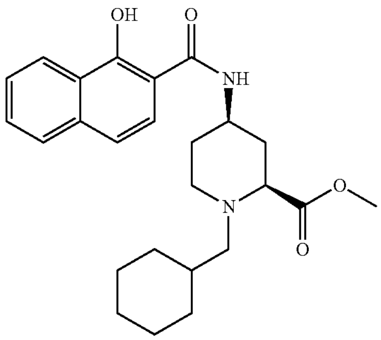 [SMILES: COC(=O)[C@@H]1C[C@H](NC(=O)c2ccc3ccccc3c2O)CCN1CC1CCCCC1] | (2S,4R)-1-Cyclohexylmethyl-4-[(1-hydroxy-naphthalene-2-carbonyl)-amino]-piperidine-2-carboxylic acid methyl ester | 23 |
| I-7 | 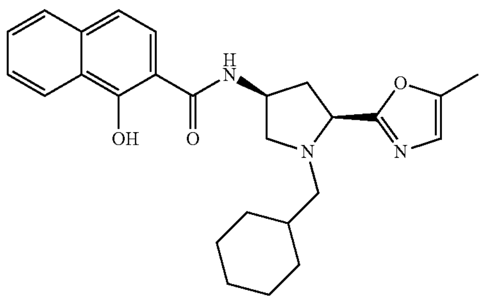 [SMILES: Cc1cnc([C@@H]2C[C@H](NC(=O)c3ccc4ccccc4c3O)CN2CC2CCCCC2)o1] | 1-Hydroxy-naphthalene-2-carboxylic acid [(3S,5S)-1-cyclohexylmethyl-5-(5-methyl-oxazol-2-yl)-pyrrolidin-3-yl]-amide | 27 |
| I-8 | 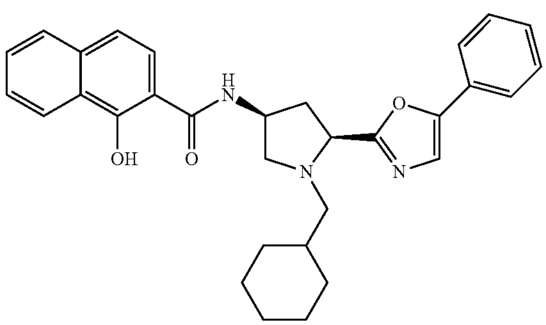 [SMILES: O=C(N[C@H]1C[C@@H](c2ncc(-c3ccccc3)o2)N(CC2CCCCC2)C1)c1ccc2ccccc2c1O] | 1-Hydroxy-naphthalene-2-carboxylic acid [(3S,5S)-1-cyclohexylmethyl-5-(5-phenyl-oxazol-2-yl)-pyrrolidin-3-yl]-amide | 28 |
| I-9 | 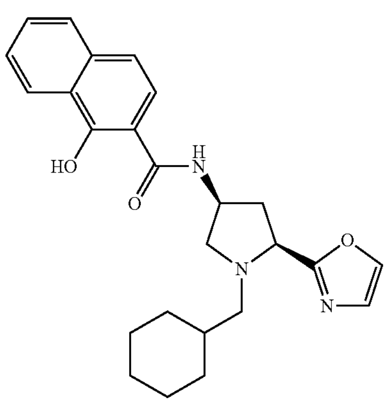 [SMILES: O=C(N[C@H]1C[C@@H](c2ncco2)N(CC2CCCCC2)C1)c1ccc2ccccc2c1O] | 1-Hydroxy-naphthalene-2-carboxylic acid ((3S,5S)-1-cyclohexylmethyl-5-oxazol-2-yl-pyrrolidin-3-yl)-amide | 26 |

TABLE I-continued

| # | Structure | Nomenclature | Example # |
|---|---|---|---|
| I-10 | 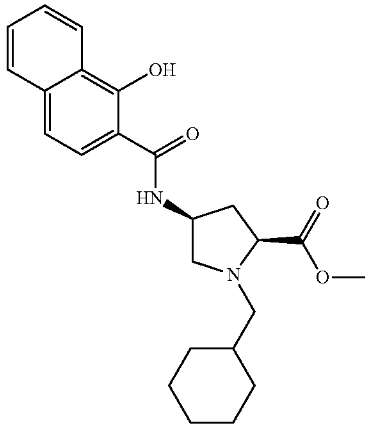 [SMILES: COC(=O)[C@@H]1C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-pyrrolidine-2-carboxylic acid methyl ester | 1 |
| I-11 | 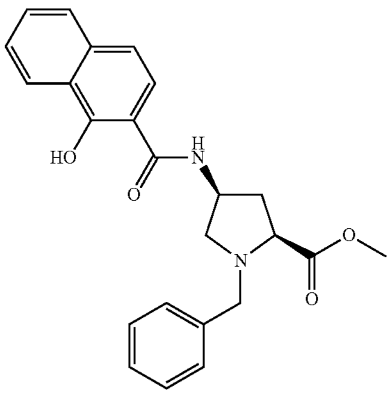 [SMILES: COC(=O)[C@@H]1C[C@H](NC(=O)c2ccc3ccccc3c2O)CN1Cc1ccccc1] | (2S,4S)-1-Benzyl-4-[(1-hydroxy-naphthalene-2-carbonyl)-amino]-pyrrolidine-2-carboxylic acid methyl ester | 2 |
| I-12 | 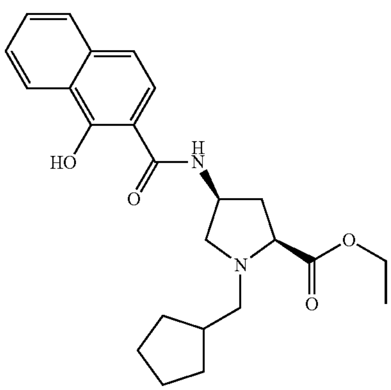 [SMILES: CCOC(=O)[C@@H]1C[C@H](NC(=O)c2ccc3ccccc3c2O)CN1CC1CCCC1] | (2S,4S)-1-Cyclopentylmethyl-4-[(1-hydroxy-naphthalene-2-carbonyl)-amino]-pyrrolidine-2-carboxylic acid ethyl ester | 4 |
| I-13 | 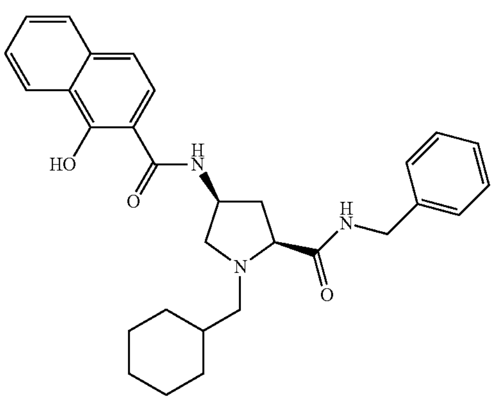 [SMILES: O=C(N[C@H]1C[C@@H](C(=O)NCc2ccccc2)N(CC2CCCCC2)C1)c1ccc2ccccc2c1O] | (2S,4S)-1-Cyclohexylmethyl-4-[(1-hydroxy-naphthalene-2-carbonyl)-amino]-pyrrolidine-2-carboxylic acid benzylamide | 14 |

TABLE I-continued

| # | Structure | Nomenclature | Example # |
|---|---|---|---|
| I-14 | 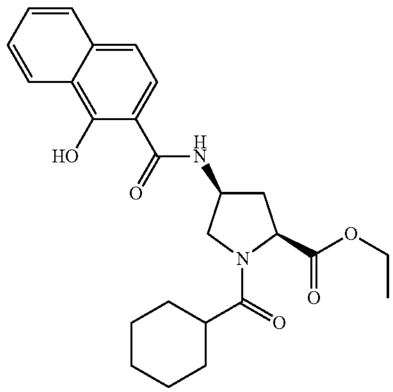 [SMILES: CCOC(=O)[C@@H]1C[C@H](NC(=O)c2ccc3ccccc3c2O)CN1C(=O)C1CCCCC1] | (2S,4S)-1-Cyclohexanecarbonyl-4-[(1-hydroxy-naphthalene-2-carbonyl)-amino]-pyrrolidine-2-carboxylic acid ethyl ester | 7 |
| I-15 | 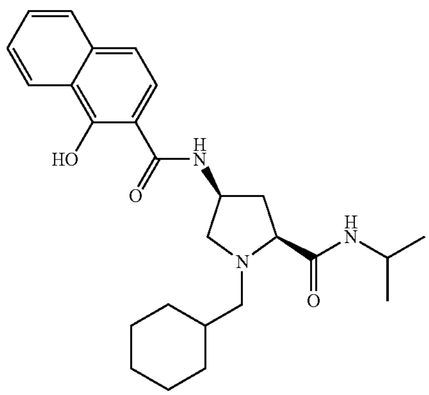 [SMILES: CC(C)NC(=O)[C@@H]1C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-pyrrolidine-2-carboxylic acid isopropylamide | 13 |
| I-16 | 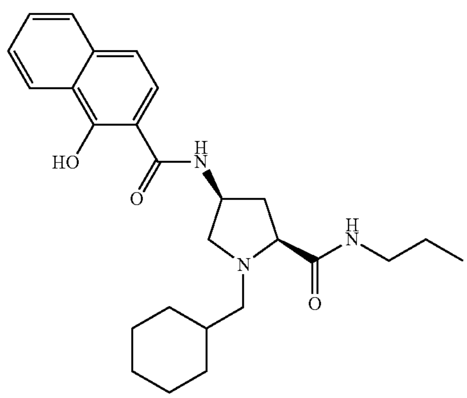 [SMILES: CCCNC(=O)[C@@H]1C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-pyrrolidine-2-carboxylic acid propylamide | 12 |
| I-17 | 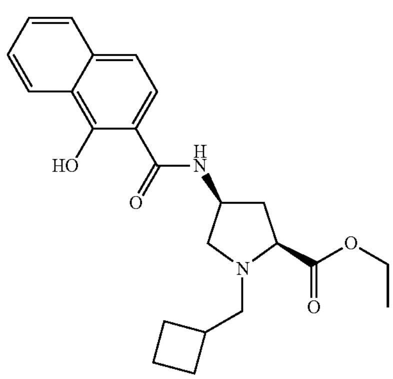 [SMILES: CCOC(=O)[C@@H]1C[C@H](NC(=O)c2ccc3ccccc3c2O)CN1CC1CCC1] | (2S,4S)-1-Cyclobutylmethyl-4-[(1-hydroxy-naphthalene-2-carbonyl)-amino]-pyrrolidine-2-carboxylic acid ethyl ester | 5 |

TABLE I-continued

| # | Structure | Nomenclature | Example # |
|---|---|---|---|
| I-18 | 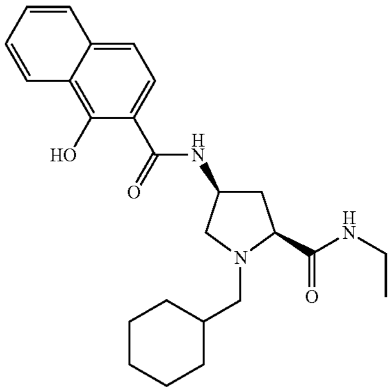 [SMILES: CCNC(=O)[C@@H]1C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-pyrrolidine-2-carboxylic acid ethylamide | 10 |
| I-19 | 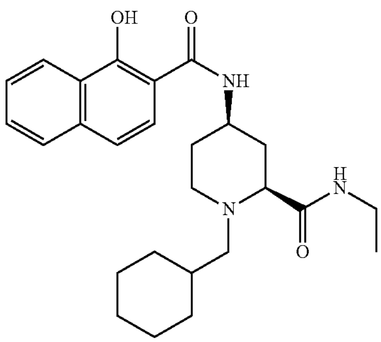 [SMILES: CCNC(=O)[C@@H]1C[C@H](NC(=O)c2ccc3ccccc3c2O)CCN1CC1CCCCC1] | (2S,4R)-1-Cyclohexylmethyl-4-[(1-hydroxy-naphthalene-2-carbonyl)-amino]-piperidine-2-carboxylic acid ethylamide | 25 |
| I-20 | 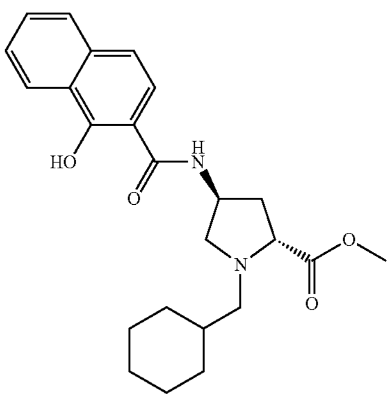 [SMILES: COC(=O)[C@H]1C[C@H](NC(=O)c2ccc3ccccc3c2O)CN1CC1CCCCC1] | (2R,4S)-1-Cyclohexylmethyl-4-[(1-hydroxy-naphthalene-2-carbonyl)-amino]-pyrrolidine-2-carboxylic acid methyl ester | 18 |
| I-21 | 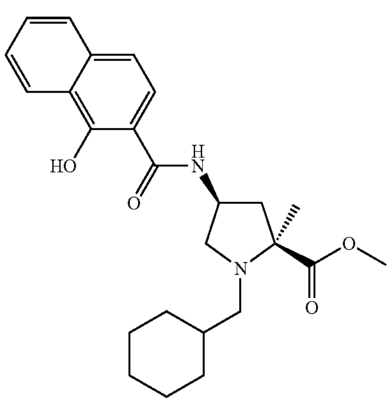 [SMILES: COC(=O)[C@]1(C)C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-2-methyl-pyrrolidine-2-carboxylic acid methyl ester | 17 |

TABLE I-continued

| # | Structure | Nomenclature | Example # |
|---|---|---|---|
| I-22 | 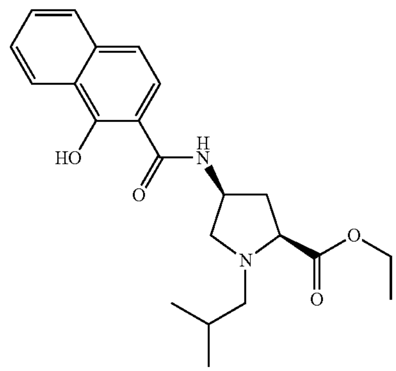 [SMILES: CCOC(=O)[C@@H]1C[C@H](NC(=O)c2ccc3ccccc3c2O)CN1CC(C)C] | (2S,4S)-4-[(1-Hydroxy-naphthalene-2-carbonyl)-amino]-1-isobutyl-pyrrolidine-2-carboxylic acid ethyl ester | 6 |
| I-23 | 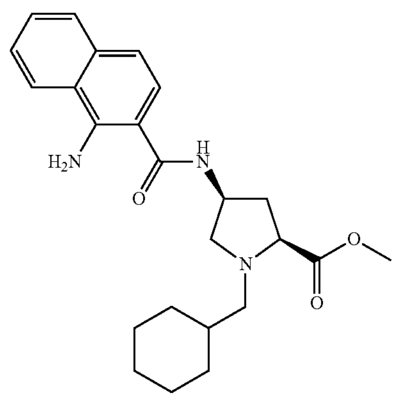 [SMILES: COC(=O)[C@@H]1C[C@H](NC(=O)c2ccc3ccccc3c2N)CN1CC1CCCCC1] | (2S,4S)-4-[(1-Amino-naphthalene-2-carbonyl)-amino]-1-cyclohexylmethyl-pyrrolidine-2-carboxylic acid methyl ester | 21 |
| I-24 | 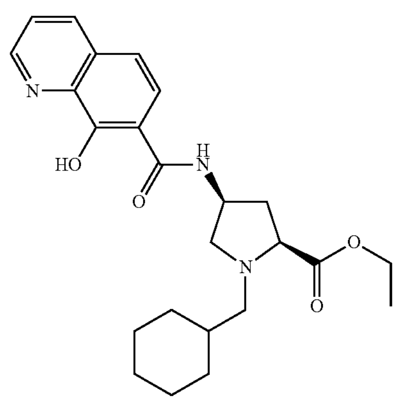 [SMILES: CCOC(=O)[C@@H]1C[C@H](NC(=O)c2ccc3cccnc3c2O)CN1CC1CCCCC1] | (2S,4S)-1-Cyclohexylmethyl-4-[(8-hydroxy-quinoline-7-carbonyl)-amino]-pyrrolidine-2-carboxylic acid ethyl ester | 22 |
| I-25 | 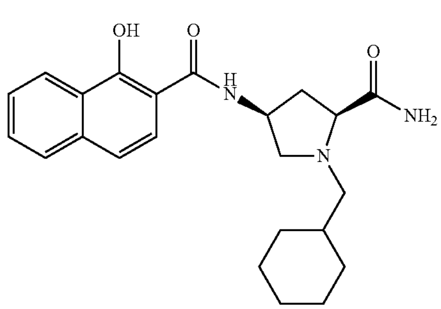 [SMILES: NC(=O)[C@@H]1C[C@H](NC(=O)c2ccc3ccccc3c2O)CN1CC1CCCCC1] | (2S,4S)-1-Cyclohexylmethyl-4-[(1-hydroxy-naphthalene-2-carbonyl)-amino]-pyrrolidine-2-carboxylic acid amide | 16 |

TABLE I-continued

| # | Structure | Nomenclature | Example # |
|---|---|---|---|
| I-26 | 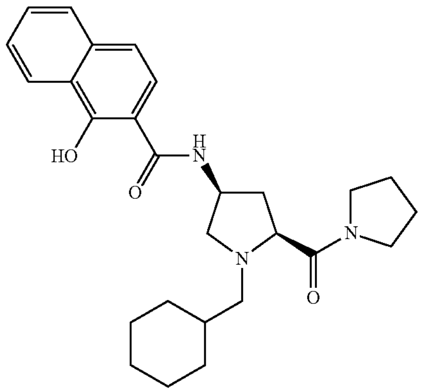 [SMILES: O=C(N[C@H]1C[C@@H](C(=O)N2CCCC2)N(CC2CCCCC2)C1)c1ccc2ccccc2c1O] | 1-Hydroxy-naphthalene-2-carboxylic acid [(3S,5S)-1-cyclohexylmethyl-5-(pyrrolidine-1-carbonyl)-pyrrolidin-3-yl]-amide | 15 |
| I-27 | 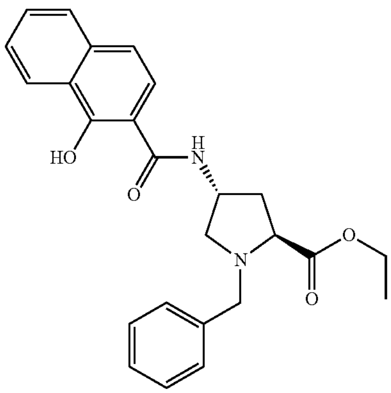 [SMILES: CCOC(=O)[C@@H]1C[C@@H](NC(=O)c2ccc3ccccc3c2O)CN1Cc1ccccc1] | (2S,4R)-1-Benzyl-4-[(1-hydroxy-naphthalene-2-carbonyl)-amino]-pyrrolidine-2-carboxylic acid ethyl ester | 20 |
| I-28 | 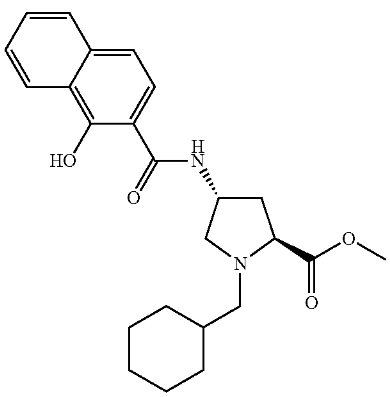 [SMILES: COC(=O)[C@@H]1C[C@@H](NC(=O)c2ccc3ccccc3c2O)CN1CC1CCCCC1] | (2S,4R)-1-Cyclohexylmethyl-4-[(1-hydroxy-naphthalene-2-carbonyl)-amino]-pyrrolidine-2-carboxylic acid methyl ester | 19 |
| I-29 | 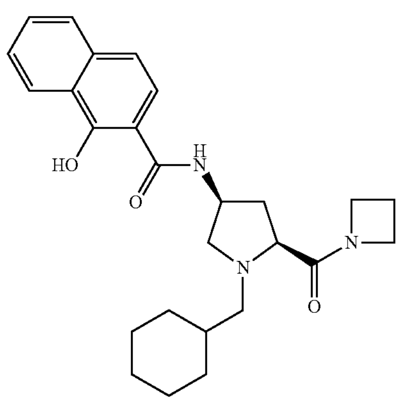 [SMILES: O=C(N[C@H]1C[C@@H](C(=O)N2CCC2)N(CC2CCCCC2)C1)c1ccc2ccccc2c1O] | 1-Hydroxy-naphthalene-2-carboxylic acid [(3S,5S)-5-(azetidine-1-carbonyl)-1-cyclohexylmethyl-pyrrolidin-3-yl]-amide | 11 |

Synthesis

General Schemes

Synthesis

General Reaction Schemes

SCHEME 1

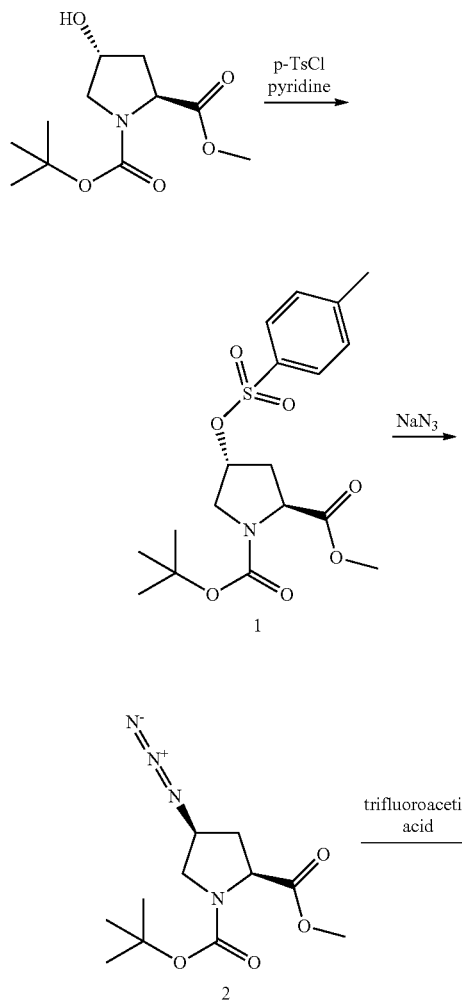

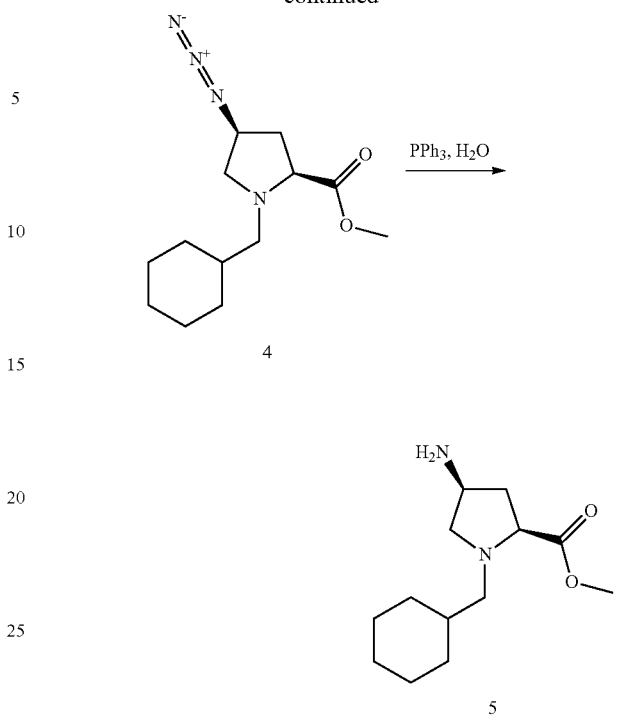

Compound 5 can be synthesized following the reactions outlined in Scheme 1. Commercially available (2S,4R)-4-hydroxy-pyrrolidine-1,2-dicarboxylic acid 1-tert-butyl ester 2-methyl ester can be treated with p-toluenesulfonyl chloride under standard conditions to provide compound 1 (see for example, PCT WO2008/148689). Compound 1 can be treated with sodium azide under standard conditions to form compound 2 (see for example, PCT WO2008/148689). Compound 2 can be treated with trifluoroacetic acid under standard Boc-group deprotection conditions to provide compound 3 (see for example, PCT WO2008/148689). Compound 3 can be treated with cyclohexanecarbaldehyde and sodium triacetoxyborohydride under standard reductive amination conditions to provide compound 4 (see for example, PCT WO2008/148689). Compound 4 can be treated under standard azide reduction conditions to provide compound 5 (see for example, PCT WO2008/148689).

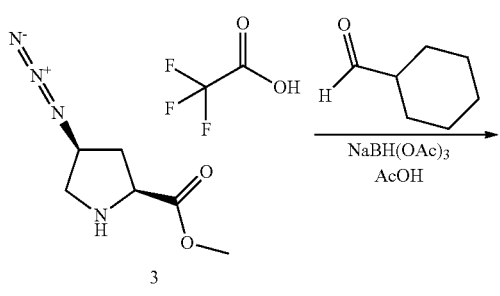

SCHEME 2

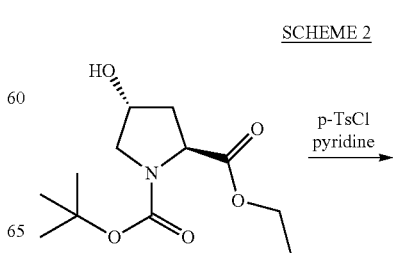

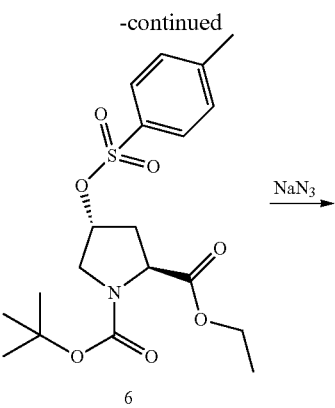

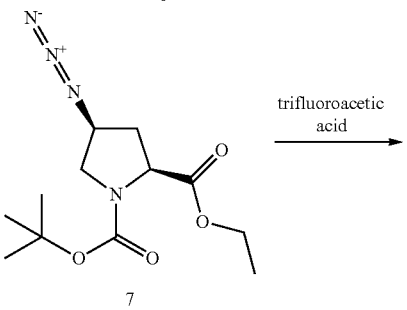

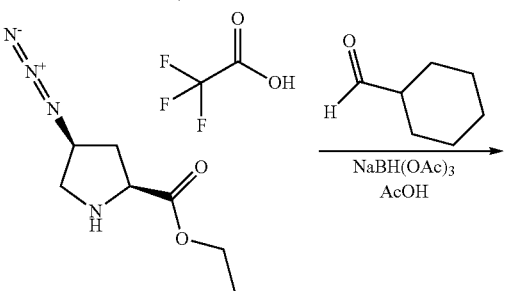

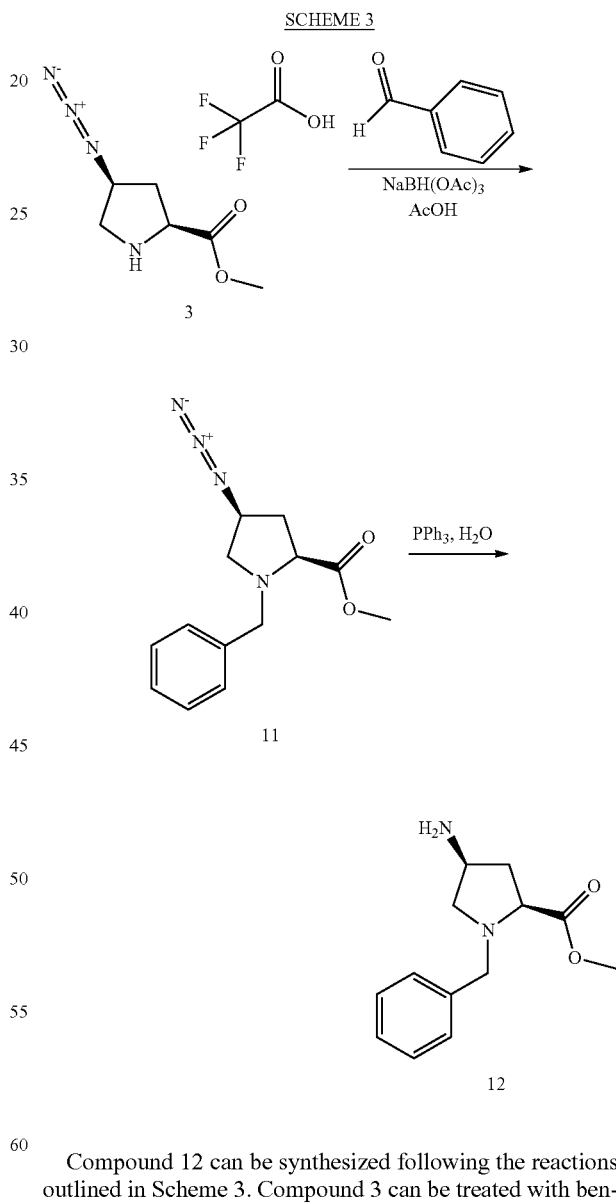

2-ethyl ester can be treated with p-toluenesulfonyl chloride under standard conditions to provide compound 6 (see for example, PCT WO2008/148689). Compound 6 can be treated with sodium azide under standard conditions to form compound 7 (see for example, PCT WO2008/148689). Compound 7 can be treated with trifluoroacetic acid under standard Boc-group deprotection conditions to provide compound 8 (see for example, PCT WO2008/148689). Compound 8 can be treated with cyclohexanecarbaldehyde and sodium triacetoxyborohydride under standard reductive amination conditions to provide compound 9 (see for example, PCT WO2008/148689). Compound 9 can be treated under standard azide reduction conditions to provide compound 10 (see for example, PCT WO2008/148689).

Compound 10 can be synthesized following the reactions outlined in Scheme 2. Commercially available (2S,4R)-4-hydroxy-pyrrolidine-1,2-dicarboxylic acid 1-tert-butyl ester Compound 12 can be synthesized following the reactions outlined in Scheme 3. Compound 3 can be treated with benzaldehyde and sodium triacetoxyborohydride under standard reductive amination conditions to provide compound 11 (see for example, PCT WO2008/148689). Compound 11 can be treated under standard azide reduction conditions to provide compound 12 (see for example, PCT WO2008/148689).

SCHEME 4

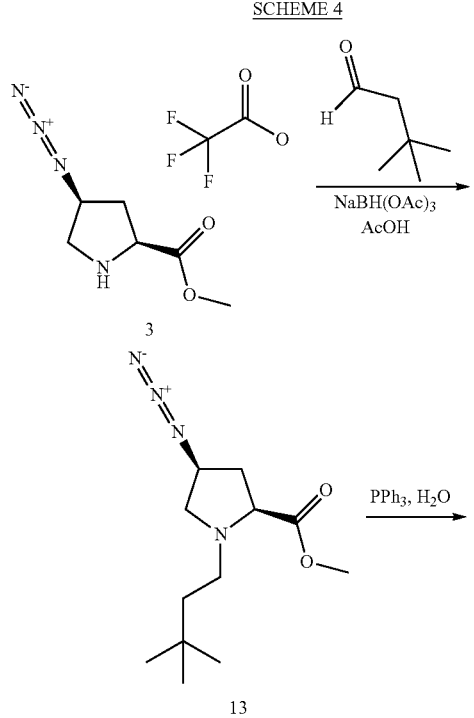

Compound 14 can be synthesized following the reactions outlined in Scheme 4. Compound 3 can be treated with 3,3-dimethyl-butyraldehyde and sodium triacetoxyborohydride under standard reductive amination conditions to provide compound 13 (see for example, PCT WO2008/148689). Compound 13 can be treated under standard azide reduction conditions to provide compound 14 (see for example, PCT WO2008/148689).

SCHEME 5

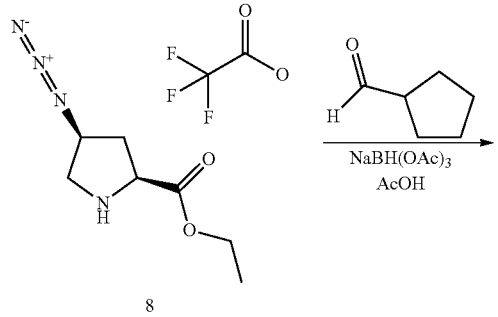

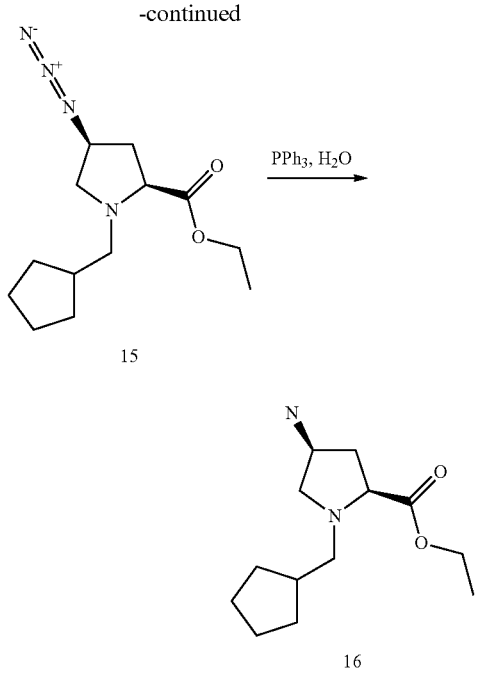

Compound 16 can be synthesized following the reactions outlined in Scheme 5. Compound 8 can be treated with cyclopentanecarbaldehyde and sodium triacetoxyborohydride under standard reductive amination conditions to provide compound 15 (see for example, PCT WO2008/148689). Compound 15 can be treated under standard azide reduction conditions to provide compound 16 (see for example, PCT WO2008/148689).

SCHEME 6

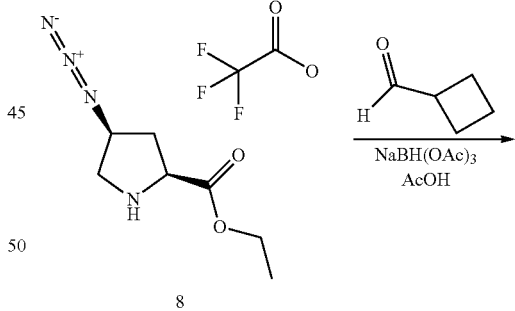

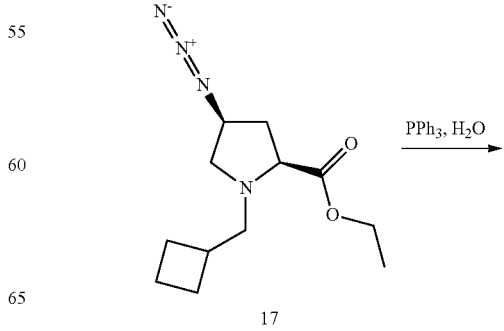

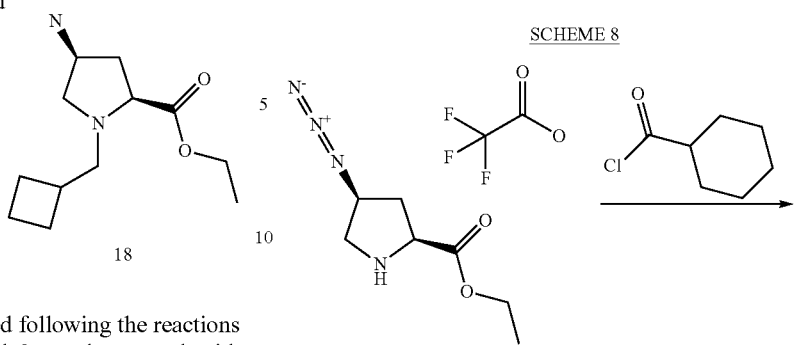

Compound 18 can be synthesized following the reactions outlined in Scheme 6. Compound 8 can be treated with cyclobutanecarbaldehyde and sodium triacetoxyborohydride under standard reductive amination conditions to provide compound 17 (see for example, PCT WO2008/148689). Compound 17 can be treated under standard azide reduction conditions to provide compound 18 (see for example, PCT WO2008/148689).

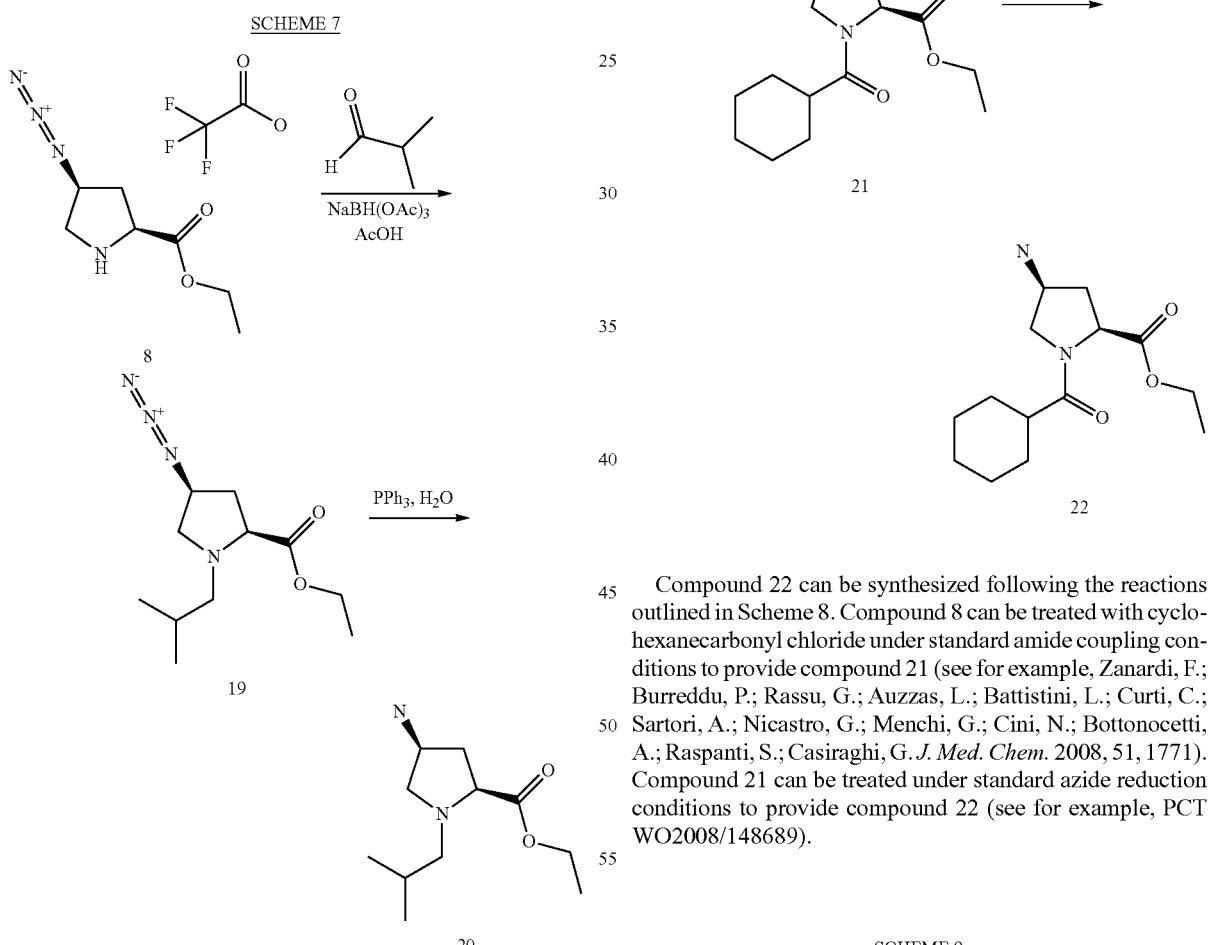

Compound 20 can be synthesized following the reactions outlined in Scheme 7. Compound 8 can be treated with isobutyraldehyde and sodium triacetoxyborohydride under standard reductive amination conditions to provide compound 19 (see for example, PCT WO2008/148689). Compound 19 can be treated under standard azide reduction conditions to provide compound 20 (see for example, PCT WO2008/148689).

Compound 22 can be synthesized following the reactions outlined in Scheme 8. Compound 8 can be treated with cyclohexanecarbonyl chloride under standard amide coupling conditions to provide compound 21 (see for example, Zanardi, F.; Burreddu, P.; Rassu, G.; Auzzas, L.; Battistini, L.; Curti, C.; Sartori, A.; Nicastro, G.; Menchi, G.; Cini, N.; Bottonocetti, A.; Raspanti, S.; Casiraghi, G. *J. Med. Chem.* 2008, 51, 1771). Compound 21 can be treated under standard azide reduction conditions to provide compound 22 (see for example, PCT WO2008/148689).

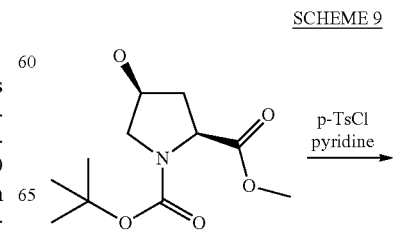

Compound 27 can be synthesized following the reactions outlined in Scheme 9. Commercially available (2S,4S)-4-hydroxy-pyrrolidine-1,2-dicarboxylic acid 1-tert-butyl ester 2-methyl ester can be treated with p-toluenesulfonyl chloride under standard conditions to provide compound 23 (see for example, PCT WO2008/148689). Compound 23 can be treated with sodium azide under standard conditions to form compound 24 (see for example, PCT WO2008/148689). Compound 24 can be treated with trifluoroacetic acid under standard Boc-group deprotection conditions to provide compound 25 (see for example, PCT WO2008/148689). Compound 25 can be treated with cyclohexanecarbaldehyde and sodium triacetoxyborohydride under standard reductive amination conditions to provide compound 26 (see for example, PCT WO2008/148689). Compound 26 can be treated under standard azide reduction conditions to provide compound 27 (see for example, PCT WO2008/148689).

SCHEME 10

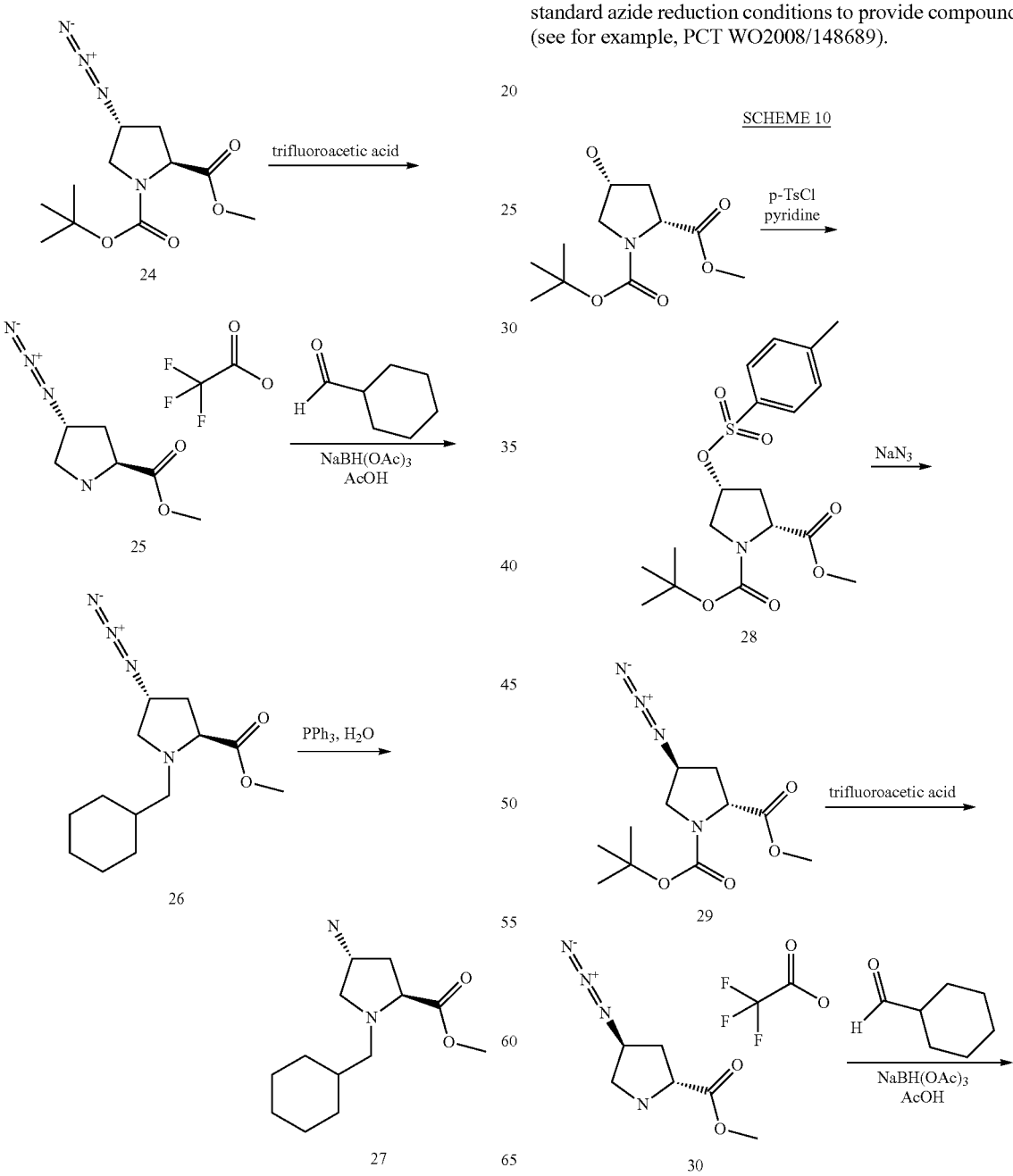

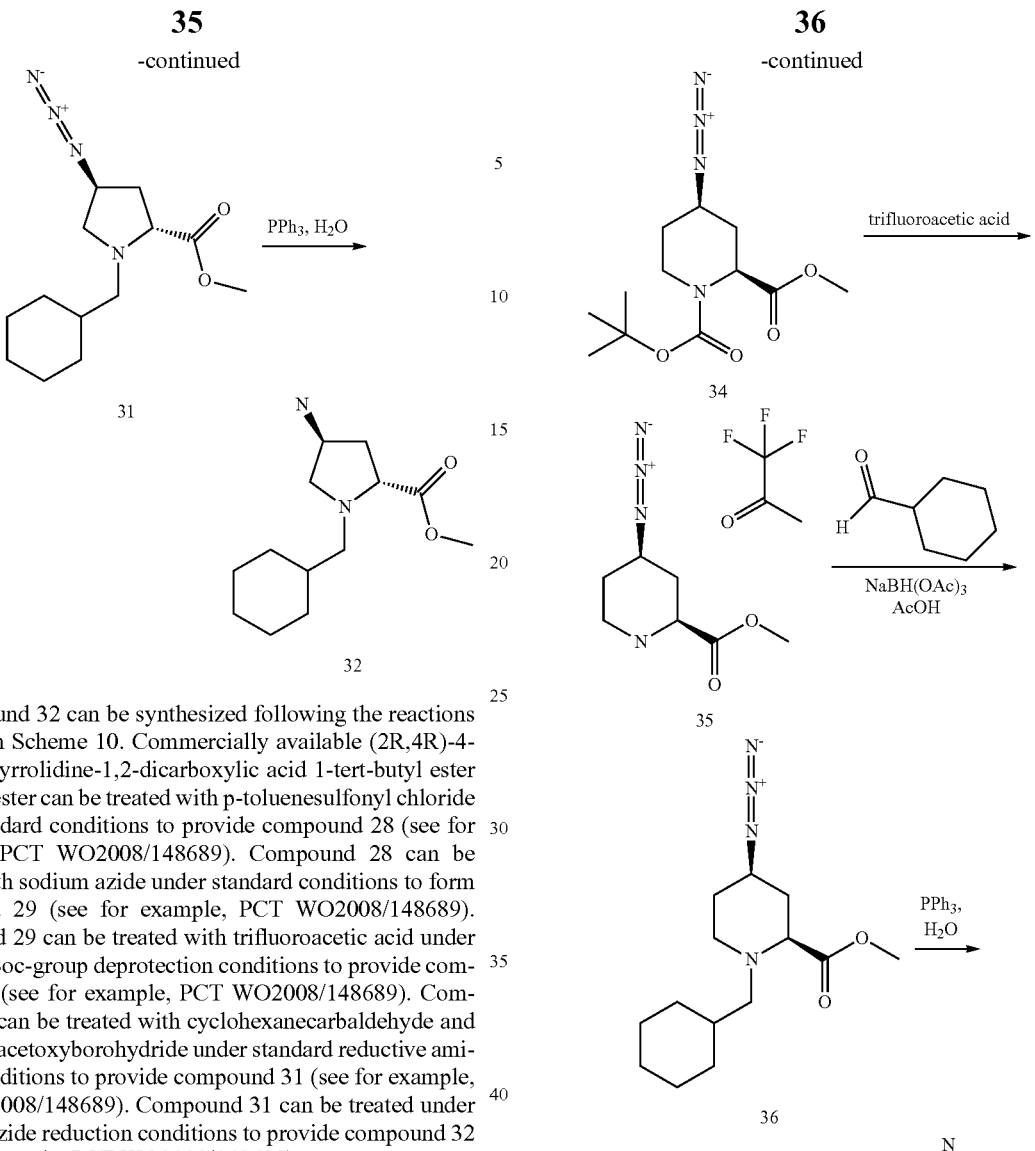

Compound 32 can be synthesized following the reactions outlined in Scheme 10. Commercially available (2R,4R)-4-hydroxy-pyrrolidine-1,2-dicarboxylic acid 1-tert-butyl ester 2-methyl ester can be treated with p-toluenesulfonyl chloride under standard conditions to provide compound 28 (see for example, PCT WO2008/148689). Compound 28 can be treated with sodium azide under standard conditions to form compound 29 (see for example, PCT WO2008/148689). Compound 29 can be treated with trifluoroacetic acid under standard Boc-group deprotection conditions to provide compound 30 (see for example, PCT WO2008/148689). Compound 30 can be treated with cyclohexanecarbaldehyde and sodium triacetoxyborohydride under standard reductive amination conditions to provide compound 31 (see for example, PCT WO2008/148689). Compound 31 can be treated under standard azide reduction conditions to provide compound 32 (see for example, PCT WO2008/148689).

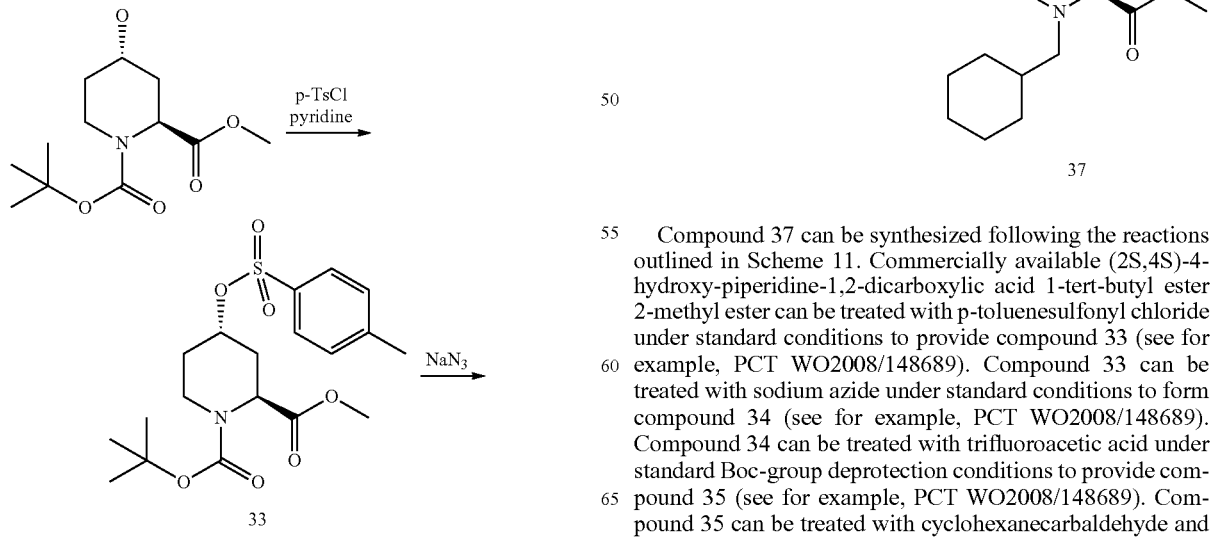

SCHEME 11

Compound 37 can be synthesized following the reactions outlined in Scheme 11. Commercially available (2S,4S)-4-hydroxy-piperidine-1,2-dicarboxylic acid 1-tert-butyl ester 2-methyl ester can be treated with p-toluenesulfonyl chloride under standard conditions to provide compound 33 (see for example, PCT WO2008/148689). Compound 33 can be treated with sodium azide under standard conditions to form compound 34 (see for example, PCT WO2008/148689). Compound 34 can be treated with trifluoroacetic acid under standard Boc-group deprotection conditions to provide compound 35 (see for example, PCT WO2008/148689). Compound 35 can be treated with cyclohexanecarbaldehyde and sodium triacetoxyborohydride under standard reductive amination conditions to provide compound 36 (see for example, PCT WO2008/148689). Compound 36 can be treated under standard azide reduction conditions to provide compound 37 (see for example, PCT WO2008/148689).

SCHEME 12

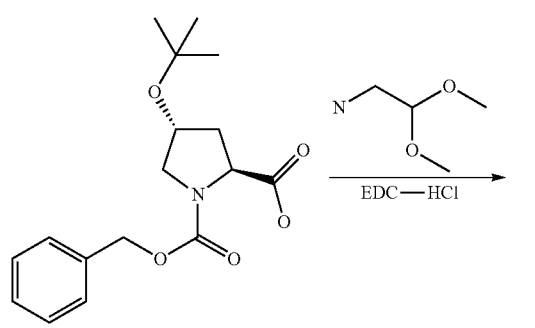

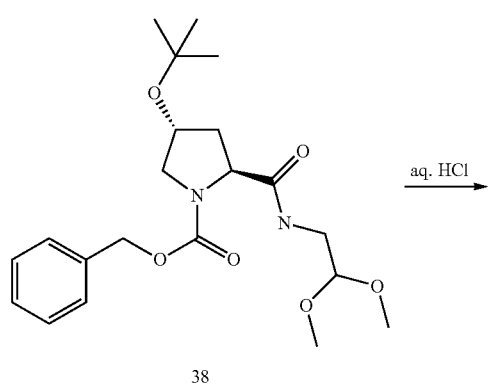

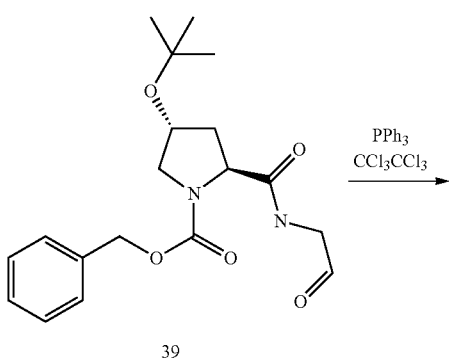

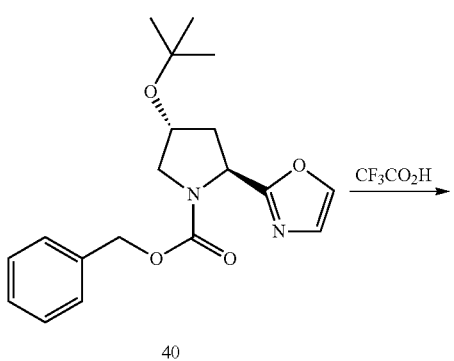

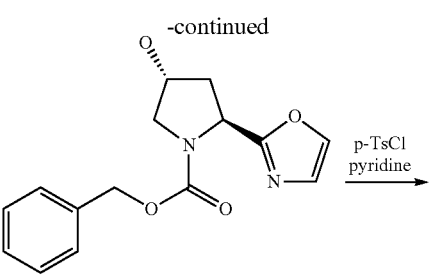

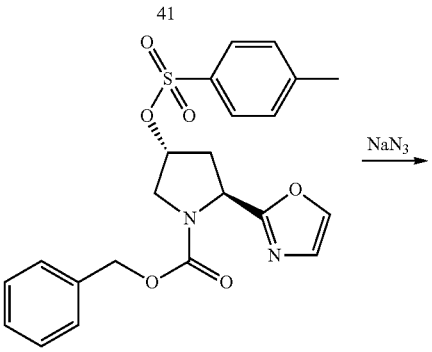

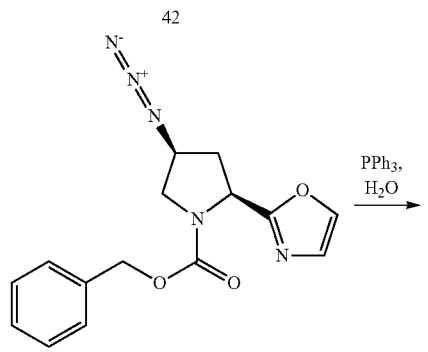

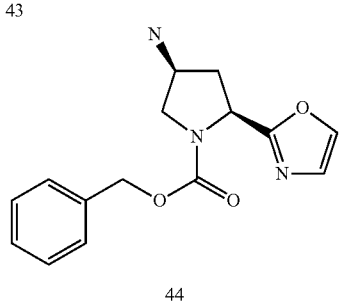

Compound 44 can be synthesized following the reactions outlined in Scheme 12. Commercially available (2S,4R)-4-tert-butoxy-pyrrolidine-1,2-dicarboxylic acid 1-benzyl ester can be coupled to 2,2-dimethoxy-ethylamine under standard amide coupling conditions to provide compound 38 (see for example, US 2007/0167426). Compound 38 can be treated with hydrochloric acid under standard conditions to form compound 39 (see for example, PCT WO2004/113353). Compound 39 can be treated with hexachloroethane and triphenylphosphine under standard conditions to provide compound 40 (see for example, PCT WO2007/077004). Compound 40 can be treated with trifluoroacetic acid under standard conditions to form compound 41 (see for example, PCT WO2007/106670). Compound 41 can be treated with p-toluenesulfonyl chloride under standard conditions to provide compound 42 (see for example, PCT WO2008/148689).

Compound 42 can be treated with sodium azide under standard conditions to form compound 43 (see for example, PCT WO2008/148689). Compound 43 can be treated under standard azide reduction conditions to provide compound 44 (see for example, PCT WO2008/148689).

SCHEME 13

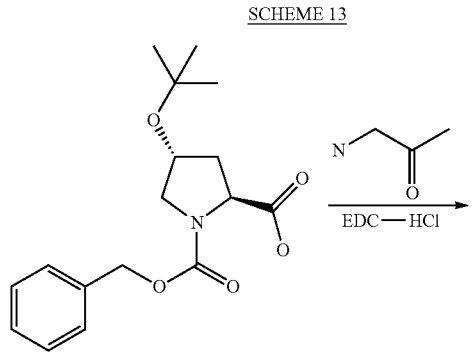

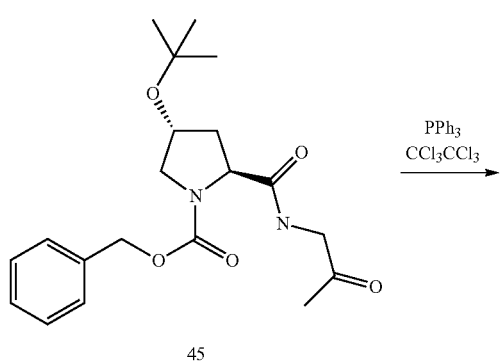

45

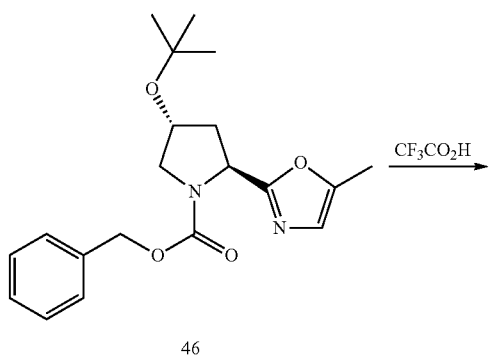

46

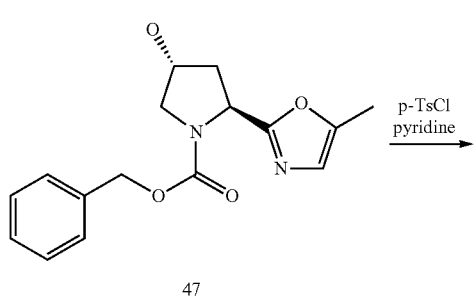

47

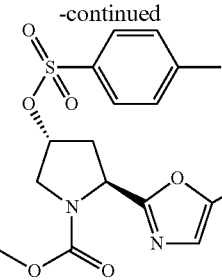

48

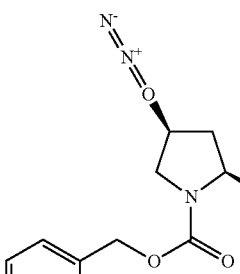

49

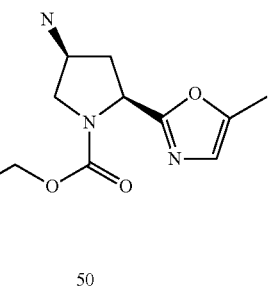

50

Compound 50 can be synthesized following the reactions outlined in Scheme 13. Commercially available (2S,4R)-4-tert-butoxy-pyrrolidine-1,2-dicarboxylic acid 1-benzyl ester can be coupled to 1-amino-propan-2-one under standard amide coupling conditions to provide compound 45 (see for example, US 2007/0167426). Compound 45 can be treated with hexachloroethane and triphenylphosphine under standard conditions to provide compound 46 (see for example, PCT WO2007/077004). Compound 46 can be treated with trifluoroacetic acid under standard conditions to form compound 47 (see for example, PCT WO2007/106670). Compound 47 can be treated with p-toluenesulfonyl chloride under standard conditions to provide compound 48 (see for example, PCT WO2008/148689). Compound 48 can be treated with sodium azide under standard conditions to form compound 49 (see for example, PCT WO2008/148689). Compound 49 can be treated under standard azide reduction conditions to provide compound 50 (see for example, PCT WO2008/148689).

SCHEME 14

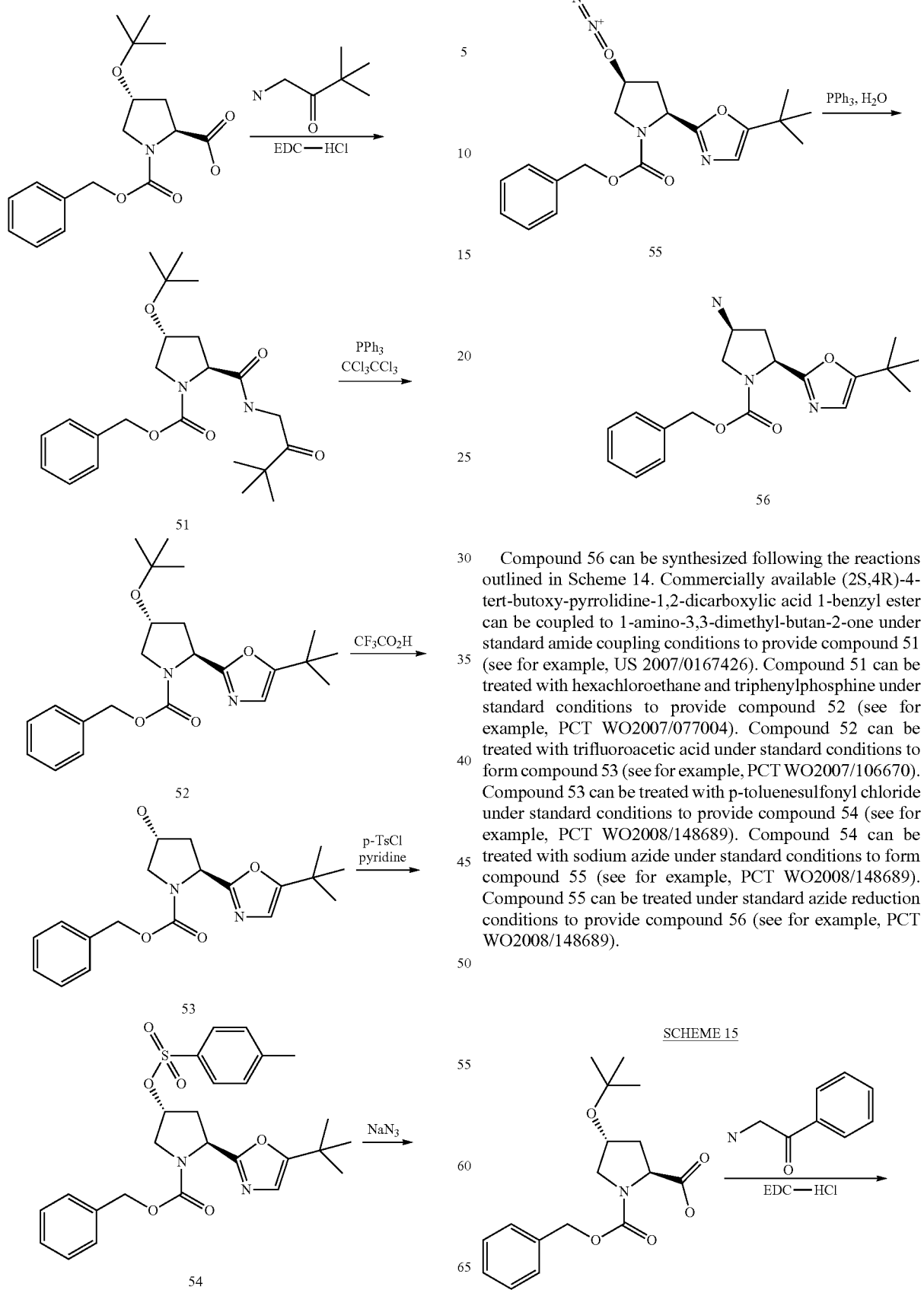

Compound 56 can be synthesized following the reactions outlined in Scheme 14. Commercially available (2S,4R)-4-tert-butoxy-pyrrolidine-1,2-dicarboxylic acid 1-benzyl ester can be coupled to 1-amino-3,3-dimethyl-butan-2-one under standard amide coupling conditions to provide compound 51 (see for example, US 2007/0167426). Compound 51 can be treated with hexachloroethane and triphenylphosphine under standard conditions to provide compound 52 (see for example, PCT WO2007/077004). Compound 52 can be treated with trifluoroacetic acid under standard conditions to form compound 53 (see for example, PCT WO2007/106670). Compound 53 can be treated with p-toluenesulfonyl chloride under standard conditions to provide compound 54 (see for example, PCT WO2008/148689). Compound 54 can be treated with sodium azide under standard conditions to form compound 55 (see for example, PCT WO2008/148689). Compound 55 can be treated under standard azide reduction conditions to provide compound 56 (see for example, PCT WO2008/148689).

SCHEME 15

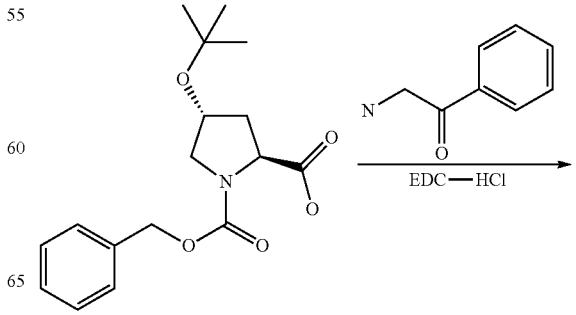

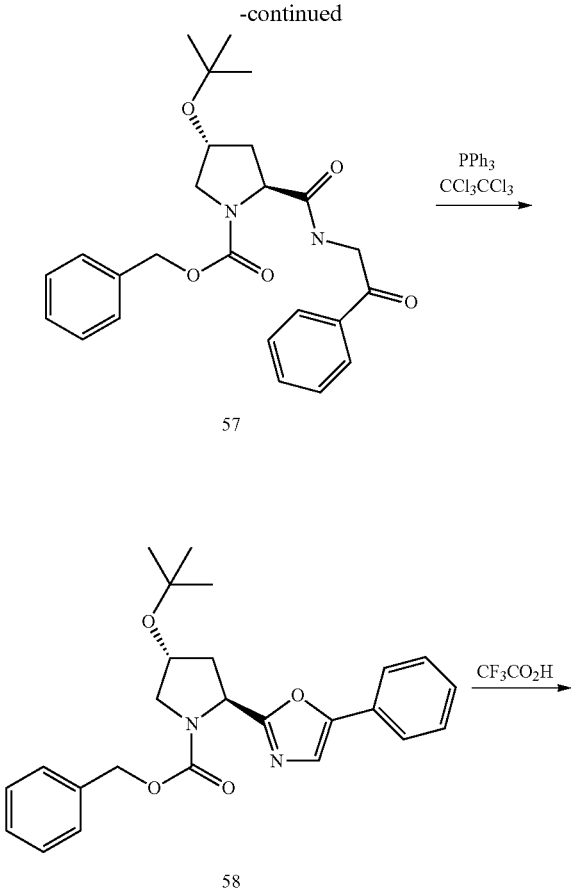

57

58

59

60

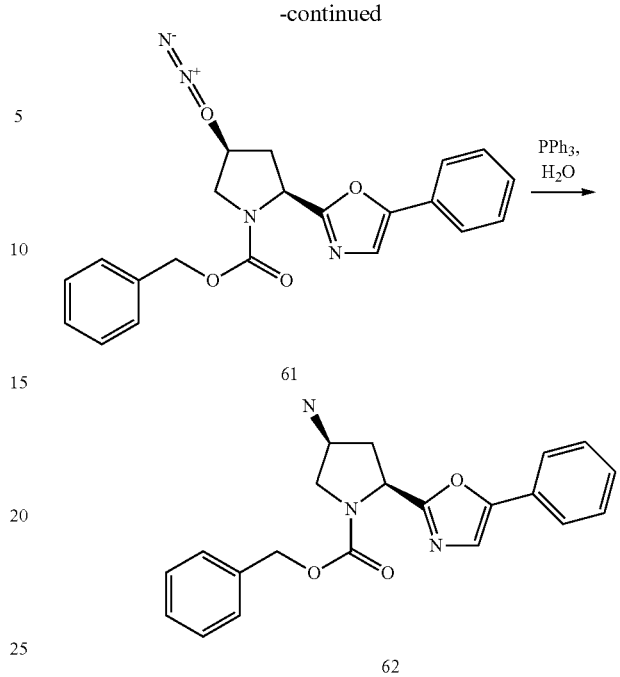

61

62

Compound 62 can be synthesized following the reactions outlined in Scheme 15. Commercially available (2S,4R)-4-tert-butoxy-pyrrolidine-1,2-dicarboxylic acid 1-benzyl ester can be coupled to 2-amino-1-phenyl-ethanone under standard amide coupling conditions to provide compound 57 (see for example, US 2007/0167426). Compound 57 can be treated with hexachloroethane and triphenylphosphine under standard conditions to provide compound 58 (see for example, PCT WO2007/077004). Compound 58 can be treated with trifluoroacetic acid under standard conditions to form compound 59 (see for example, PCT WO2007/106670). Compound 59 can be treated with p-toluenesulfonyl chloride under standard conditions to provide compound 60 (see for example, PCT WO2008/148689). Compound 60 can be treated with sodium azide under standard conditions to form compound 61 (see for example, PCT WO2008/148689). Compound 61 can be treated under standard azide reduction conditions to provide compound 62 (see for example, PCT WO2008/148689).

SCHEME 16

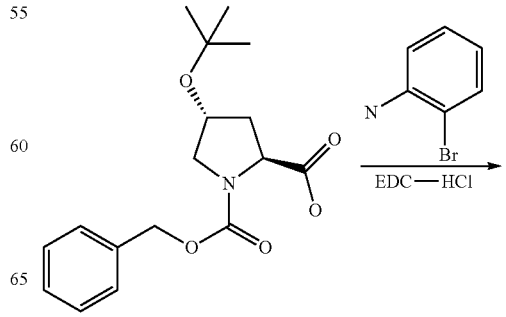

-continued

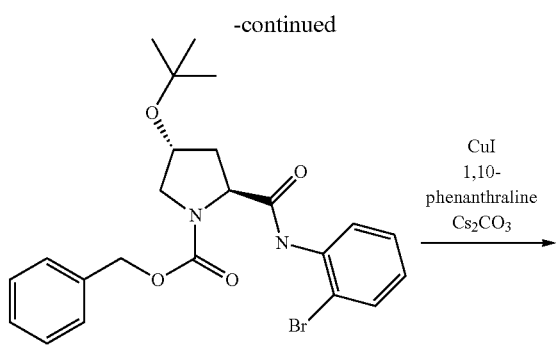

63

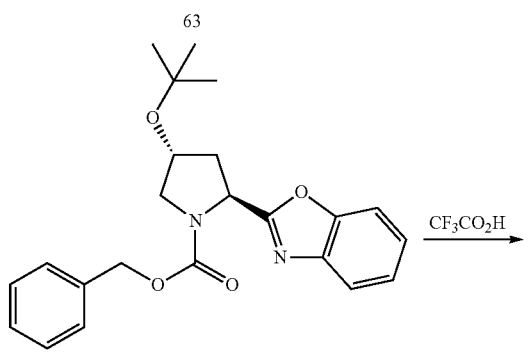

64

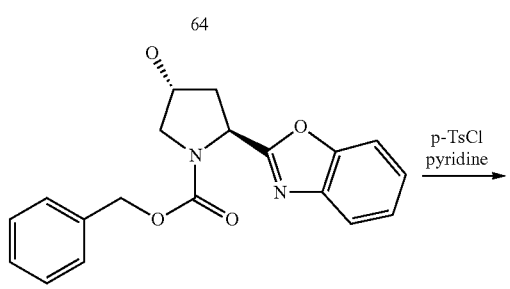

65

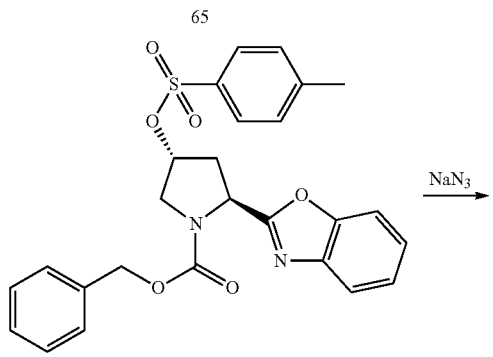

66

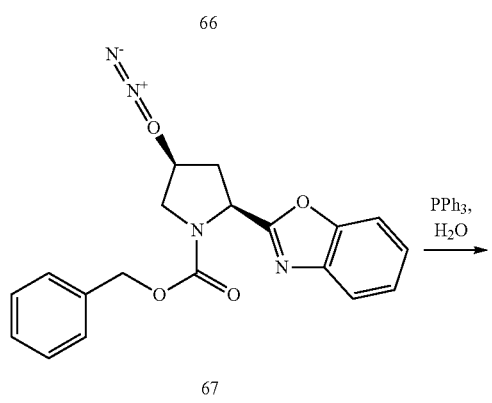

67

-continued

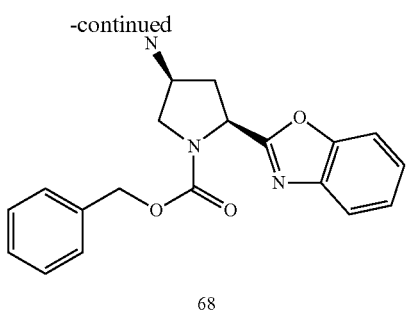

68

Compound 68 can be synthesized following the reactions outlined in Scheme 16. Commercially available (2S,4R)-4-tert-butoxy-pyrrolidine-1,2-dicarboxylic acid 1-benzyl ester can be coupled to 2-bromo-phenylamine under standard amide coupling conditions to provide compound 63 (see for example, US 2007/0167426). Compound 63 can be treated with copper (I) iodide and 1,10-phenanthraline to provide compound 64 (see for example, Evindar, G.; Batey, R. A. *J. Org. Chem.* 2006, 71, 1802). Compound 64 can be treated with trifluoroacetic acid under standard conditions to form compound 65 (see for example, PCT WO2007/106670). Compound 65 can be treated with p-toluenesulfonyl chloride under standard conditions to provide compound 66 (see for example, PCT WO2008/148689). Compound 66 can be treated with sodium azide under standard conditions to form compound 67 (see for example, PCT WO2008/148689). Compound 67 can be treated under standard azide reduction conditions to provide compound 68 (see for example, PCT WO2008/148689).

SCHEME 17

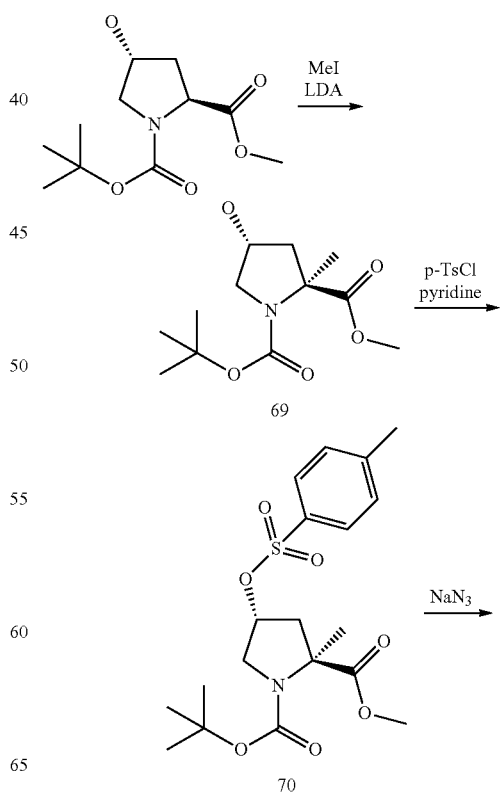

69

70

-continued

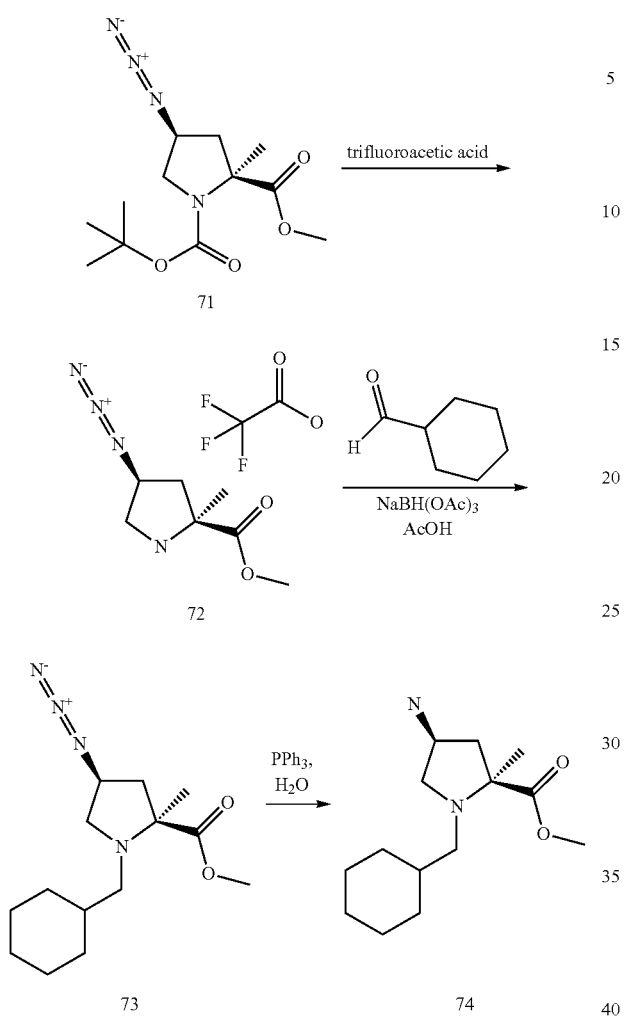

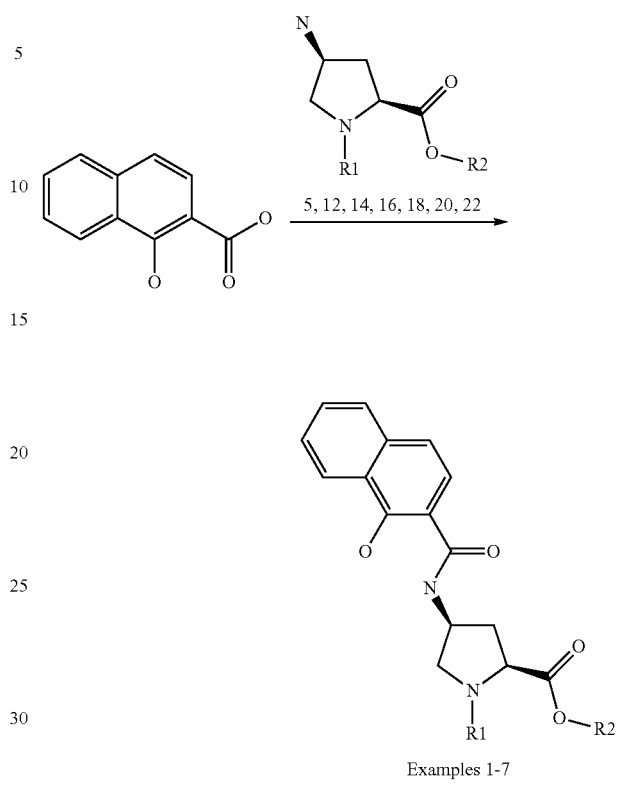

Examples 1-7 can be synthesized following the reactions outlined in Scheme 18. Commercially available 1-hydroxy-naphthalene-2-carboxylic acid can be treated with different amines (e.g. 5, 12, 14, 16, 18, 20 and 22) under standard amide coupling conditions (e.g. HATU, HBTU) to afford examples 1-7 (see for example, PCT WO2010/009196).

Compound 74 can be synthesized following the reactions outlined in Scheme 17. Commercially available (2S,4R)-4-hydroxy-pyrrolidine-1,2-dicarboxylic acid 1-tert-butyl ester 2-methyl ester can be treated with lithium diisopropylamide and iodomethane to provide compound 69 (see for example, Noe, C. R.; Knollmueller, M.; Voellenkle, H.; Noe-Letsching, M.; Weigand, A.; Muehl, *J. Pharmazie,* 1996, 51, 800). Compound 69 can be treated with p-toluenesulfonyl chloride under standard conditions to provide compound 70 (see for example, PCT WO2008/148689). Compound 70 can be treated with sodium azide under standard conditions to form compound 71 (see for example, PCT WO2008/148689). Compound 71 can be treated with trifluoroacetic acid under standard Boc-group deprotection conditions to provide compound 72 (see for example, PCT WO2008/148689). Compound 72 can be treated with cyclohexanecarbaldehyde and sodium triacetoxyborohydride under standard reductive amination conditions to provide compound 73 (see for example, PCT WO2008/148689). Compound 73 can be treated under standard azide reduction conditions to provide compound 74 (see for example, PCT WO2008/148689).

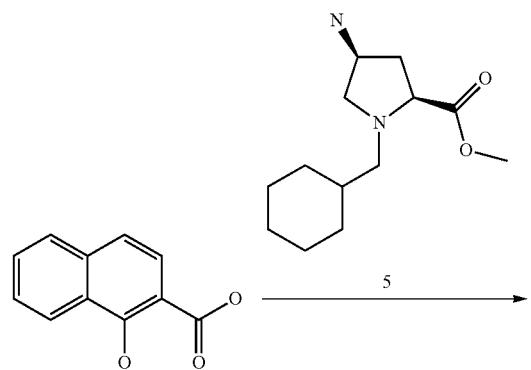

-continued

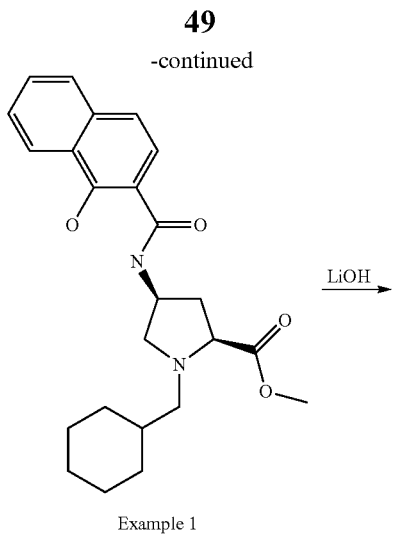

Example 1

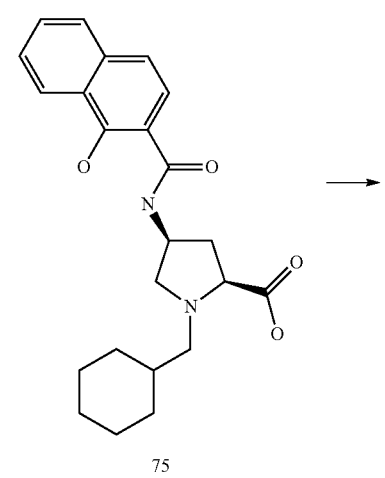

75

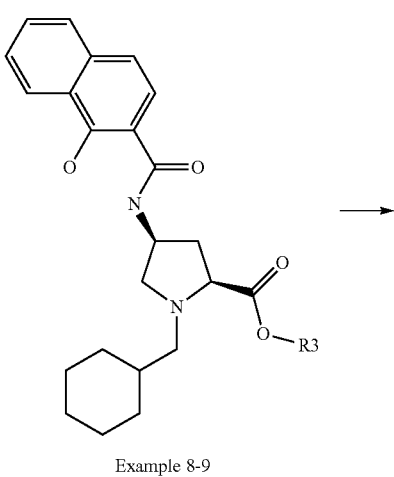

Example 8-9

-continued

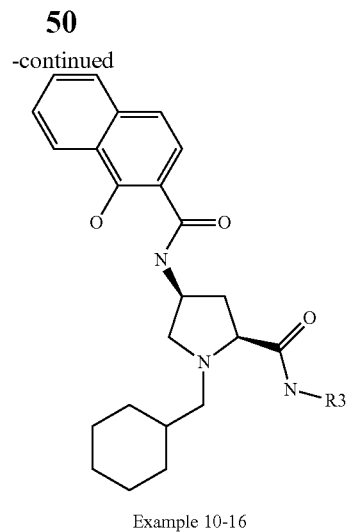

Example 10-16

Examples 8-16 can be synthesized following the reactions outlined in Scheme 19. Commercially available 1-hydroxy-naphthalene-2-carboxylic acid can be treated with (2S,4S)-4-amino-1-cyclohexylmethyl-pyrrolidine-2-carboxylic acid methyl ester (compound 5) under standard amide coupling conditions (e.g. HATU, HBTU) to afford example 1 (see for example, PCT WO2010/009196). Example 1 can be treated with lithium hydroxide under standard ester hydrolysis conditions to afford compound 75 (see for example, WO2008/046527). Compound 75 can be treated under standard esterification conditions to afford examples 8-9 (see for example, Bellis, E.; Kokotos, G. *Tetrahedron* 2005, 61, 8669). Compound 75 can be treated under standard amide coupling conditions (e.g. HATU, HBTU, see for example PCT WO2010/009196) to afford examples 10-16.

SCHEME 20

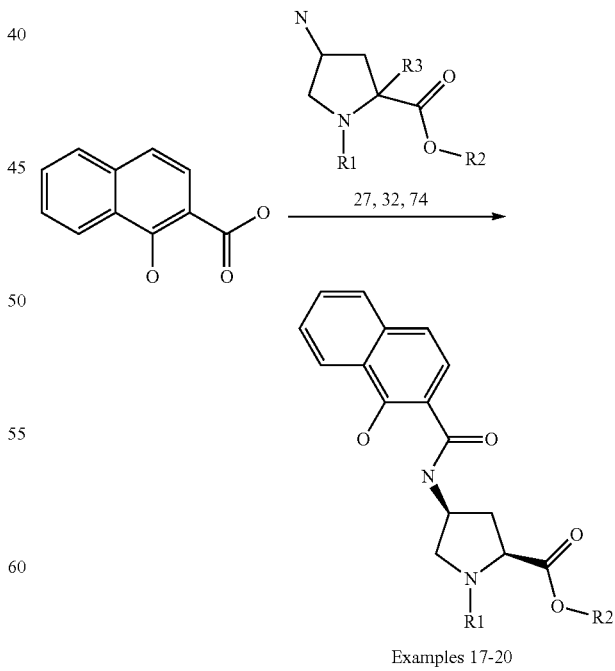

Examples 17-20

Examples 17-20 can be synthesized following the reactions outlined in Scheme 20. Commercially available 1-hydroxy-naphthalene-2-carboxylic acid can be treated with different amines (e.g. 27, 32 and 74) under standard amide coupling conditions (e.g. HATU, HBTU) to afford examples 17-20 (see for example, PCT WO2010/009196).

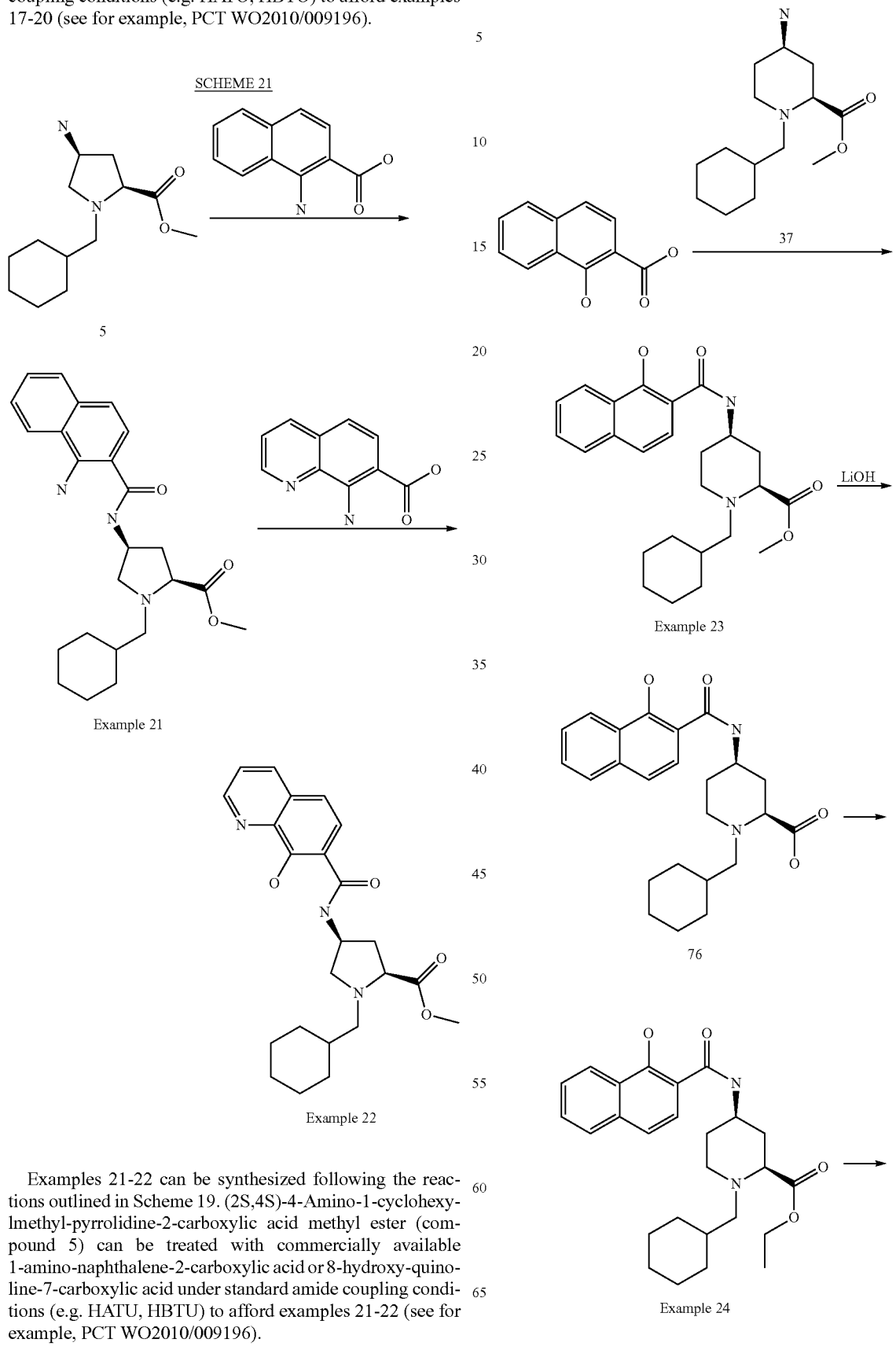

SCHEME 21

Example 21

Example 22

Examples 21-22 can be synthesized following the reactions outlined in Scheme 19. (2S,4S)-4-Amino-1-cyclohexylmethyl-pyrrolidine-2-carboxylic acid methyl ester (compound 5) can be treated with commercially available 1-amino-naphthalene-2-carboxylic acid or 8-hydroxy-quinoline-7-carboxylic acid under standard amide coupling conditions (e.g. HATU, HBTU) to afford examples 21-22 (see for example, PCT WO2010/009196).

SCHEME 22

Example 23

Example 24

Example 25

Examples 23-25 can be synthesized following the reactions outlined in Scheme 22. Commercially available 1-hydroxy-naphthalene-2-carboxylic acid can be treated with (2S,4R)-4-amino-1-cyclohexylmethyl-piperidine-2-carboxylic acid methyl ester (compound 37) under standard amide coupling conditions (e.g. HATU, HBTU) to afford example 23 (see for example, PCT WO2010/009196). Example 23 can be treated with lithium hydroxide under standard ester hydrolysis conditions to afford compound 76 (see for example, PCT WO2008/046527). Compound 76 can be treated under standard esterification conditions to afford example 24 (see for example, Bellis, E.; Kokotos, G. *Tetrahedron* 2005, 61, 8669). Compound 76 can be treated under standard amide coupling conditions (e.g. HATU, HBTU, see for example PCT WO2010/009196) to afford example 25.

SCHEME 23

44, 50, 56, 62, 68

77

78

Examples 26-29

Examples 26-29 can be synthesized following the reactions outlined in Scheme 23. Commercially available 1-hydroxy-naphthalene-2-carboxylic acid can be treated with different amines (e.g. compounds 44, 50, 56, 62 and 68) under standard amide coupling conditions (e.g. HATU, HBTU) to afford compound 77 (see for example, PCT WO2010/009196). Compound 77 can be treated with hydrogen under standard metal catalyzed deprotection conditions to afford compound 78 (see for example, Chang, D.; Heringa, M. F.; Witholt, B.; Li, Z. *J. Org. Chem.* 2003, 68, 8599). Compound 78 can be treated with cyclohexanecarbaldehyde and sodium triacetoxyborohydride under standard reductive amination conditions to provide Examples 26-29 (see for example, PCT WO2008/148689).

Pharmaceutical Compositions and Administration

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Dosage and Administration:

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Indications and Method of Treatment
Indications

The compounds of the invention and their isomeric forms and pharmaceutically acceptable salts thereof are useful in treating and preventing HCV infection.

The application provides a method for treating a Hepatitis C Virus (HCV) infection comprising administering to a patient in need thereof a therapeutically effective amount of a compound of Formula I.

The application provides a method for inhibiting replication of HCV in a cell comprising administering a compound of Formula I.

Combination Therapy

The compounds of the invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention include, without limitation, all classes of HCV antivirals.

For combination therapies, mechanistic classes of agents that can be useful when combined with the compounds of the invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-9005 18), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-8 13, PHX-1766, PHX2054, IDX-136, IDX-3 16, ABT-450 EP-0 13420 (and congeners) and VBY-376; the Nucleosidic HCV polymerase (replicase) inhibitors useful in the invention include, but are not limited to, R7128, PSI-785 1, IDX-184, IDX-102, R1479, UNX-08 189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nucleosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, compounds of the invention can be used in combination with cyclophyllin and immunophyllin antagonists (e.g., without limitation, DEBIO compounds, NM-811 as well as cyclosporine and its derivatives), kinase inhibitors, inhibitors of heat shock proteins (e.g., HSP90 and HSP70), other immunomodulatory agents that can include, without limitation, interferons (-alpha, -beta, -omega, -gamma, -lambda or synthetic) such as Intron A, Roferon-A, Canferon-A300, Advaferon, Infergen, Hunioferon, Sumiferon MP, Alfaferone, IFN-β, Feron and the like; polyethylene glycol derivatized (pegylated) interferon compounds, such as PEG interferon-α-2a (Pegasys), PEG interferon-α-2b (PEGIntron), pegylated IFN-α-con1 and the like; long acting formulations and derivatizations of interferon compounds such as the albumin-fused interferon, Albuferon, Locteron, and the like; interferons with various types of controlled delivery systems (e.g., ITCA-638, omega-interferon delivered by the DUROS subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL, REMICADE, and HUMIRA.

In addition, compounds of the invention can be used in combination with antiprotozoans and other antivirals thought to be effective in the treatment of HCV infection such as, without limitation, the prodrug nitazoxanide. Nitazoxanide can be used as an agent in combination with the compounds disclosed in this invention as well as in combination with other agents useful in treating HCV infection such as peginterferon α-2a and ribavirin.

Compounds of the invention can also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A. Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. Nos. 5,807,876; 6,498,178; 6,344,465; and 6,054,472; PCT Patent Application Publication Nos. WO97/40028; WO98/4038 1; WO00/56331, WO02/04425; WO03/007945; WO03/010141; WO03/000254; WO01/32153; WO00/06529; WO00/18231; WO00/10573; WO00/13708; WO01/85172; WO03/037893; WO03/037894; WO03/037895; WO02/100851; WO02/100846; WO99/01582; WO00/09543; WO02/18369; WO98/17679, WO00/056331; WO98/22496; WO99/07734; WO05/073216, WO05/073195 and WO08/021927.

Additionally, combinations of, for example, ribavirin and interferon, may be administered as multiple combination therapy with at least one of the compounds of the invention. The present invention is not limited to the aforementioned classes or compounds and contemplates known and new compounds and combinations of biologically active agents. It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the judgment of the one skilled in the art administering or supervising the administration of the combination therapy.

The application provides a method for treating a Hepatitis C Virus (HCV) infection comprising administering to a patient in need thereof a therapeutically effective amount of a compound of any one of Formulae I-IIII.

The application provides the above method, further comprising administering an immune system modulator or an antiviral agent that inhibits replication of HCV, or a combination thereof.

The application provides the above method, wherein the immune system modulator is an interferon or chemically derivatized interferon.

The application provides the above methods, wherein the antiviral agent is selected from the group consisting of a HCV protease inhibitor, a HCV polymerase inhibitor, a HCV helicase inhibitor, a HCV primase inhibitor, a HCV fusion inhibitor, and a combination thereof.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bisdiphenylphosphino)ferrocenyl) palladium(II) (Pd(dppf)Cl₂), palladium(II) acetate (Pd(OAc)₂), tris(dibenzylideneacetone)dipalladium(0) (Pd₂(dba)₃), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe₂Si (TBDMS), tetra-n-butylammonium fluoride (TBAF), triethylamine (TEA or Et₃N), 2,2,6,6-tetramethylpiperidine 1-oxyl (TEMPO), triflate or CF₃SO₂— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me₃Si (TMS), p-toluenesulfonic acid monohydrate (TsOH or pTsOH), 4-Me-C₆H₄SO₂— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Compounds of the invention can be made by a variety of methods depicted in the illustrative synthetic reactions described below in the Examples section.

The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, 1991, Volumes 1-15; Rodd's *Chemistry of Carbon Compounds*, Elsevier Science Publishers, 1989, Volumes 1-5 and Supplementals; and *Organic Reactions*, Wiley & Sons: New York, 1991, Volumes 1-40. It should be appreciated that the synthetic reaction schemes shown in the Examples section are merely illustrative of some methods by which the compounds of the invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein are typically conducted under an inert atmosphere at atmospheric pressure at a reaction temperature range of from about −78° C. to about 150° C., often from about 0° C. to about 125° C., and more often and conveniently at about room (or ambient) temperature, e.g., about 20° C.

Various substituents on the compounds of the invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups is known in the art, and can be employed. Examples of many of the possible groups can be found in "*Protective Groups in Organic Synthesis*" by Green et al., John Wiley and Sons, 1999. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Preparative Examples

Preparation of (2S,4S)-4-amino-1-cyclohexylmethyl-pyrrolidine-2-carboxylic acid methyl ester

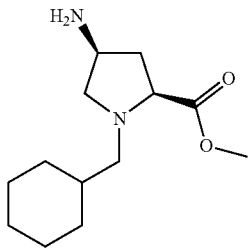 [SMILES: COC(=O)[C@@H]1C[C@H](N)CN1CC1CCCCC1]

Step 1: Preparation of (2S,4R)-4-(toluene-4-sulfonyloxy)-pyrrolidine-1,2-dicarboxylic acid 1-tert-butyl ester 2-methyl ester

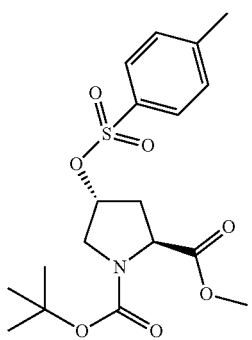 [SMILES: COC(=O)[C@@H]1C[C@@H](OS(=O)(=O)c2ccc(C)cc2)CN1C(=O)OC(C)(C)C]

To a solution of (2S,4R)-4-hydroxy-pyrrolidine-1,2-dicarboxylic acid 1-tert-butyl ester 2-methyl ester (10 g, 40.77 mmol) in methylene chloride (56 mL) at 0° C. was added pyridine (30 mL), followed by dropwise addition of a solution of p-toluenesulfonyl chloride (9.4 g, 49.30 mmol) in methylene chloride. The reaction mixture was warmed to room temperature and then refluxed for 16 h. The reaction mixture was concentrated, re-dissolved in methylene chloride, and washed with water and brine. The organic layer was dried over anhydrous sodium sulfate, filtered and concentrated to give (2S,4R)-4-(toluene-4-sulfonyloxy)-pyrrolidine-1,2-dicarboxylic acid 1-tert-butyl ester 2-methyl ester (14.4 g, 88.4% yield) as a light yellow sticky solid. The crude was used in the next step without further purification. MS calcd. for $C_{18}H_{26}NO_7S$ [(M+H)$^+$] 400.0, obsd. 400.0.

Step 2: Preparation of (2S,4S)-4-azido-pyrrolidine-1,2-dicarboxylic acid 1-tert-butyl ester 2-methyl ester

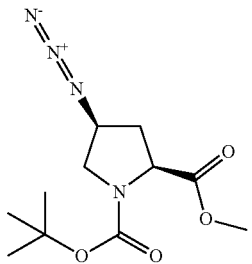 [SMILES: COC(=O)[C@@H]1C[C@H](N=[N+]=[N-])CN1C(=O)OC(C)(C)C]

To a solution of (2S,4R)-4-(toluene-4-sulfonyloxy)-pyrrolidine-1,2-dicarboxylic acid 1-tert-butyl ester 2-methyl ester (14.4 g, 36.09 mmol) in dry N,N-dimethylformamide (50 mL) was added sodium azide (4.7 g, 72.18 mmol) and the reaction mixture was stirred at 60° C. for 16 h. The reaction mixture was diluted with ethyl acetate, washed with water, brine, and dried over anhydrous sodium sulfate. Filtration and concentration gave a crude which was purified by column chromatography (15% ethyl acetate in hexane as eluent) to give (2S,4S)-4-azido-pyrrolidine-1,2-dicarboxylic acid 1-tert-butyl ester 2-methyl ester (7.8 g, 80% yield) as a light brown liquid. MS calcd. for $C_{11}H_{19}N_4O_4$ [(M+H)$^+$] 271.0, obsd. 271.0.

Step 3: Preparation of (2S,4S)-4-azido-pyrrolidine-2-carboxylic acid methyl ester trifluoroacetate salt

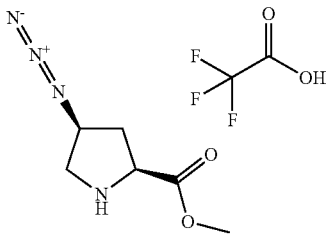

To a solution of (2S,4S)-4-azido-pyrrolidine-1,2-dicarboxylic acid 1-tert-butyl ester 2-methyl ester (7.8 g, 28.8 mmol) in methylene chloride (30 mL) was added a mixture of trifluoroacetic acid and methylene chloride (1:5, 20 mL) and the reaction mixture was stirred at room temp. for 16 h. The reaction mixture was concentrated under reduced pressure to give (2S,4S)-4-azido-pyrrolidine-2-carboxylic acid methyl ester trifluoroacetate salt (9.6 g, crude) as a light brown oil.

The compound was used in the next step without further purification. MS calcd. for $C_6H_{11}N_4O_2$ [(M+H)$^+$] 171.0, obsd. 171.2.

Step 4: Preparation of (2S,4S)-4-azido-1-cyclohexylmethyl-pyrrolidine-2-carboxylic acid methyl ester

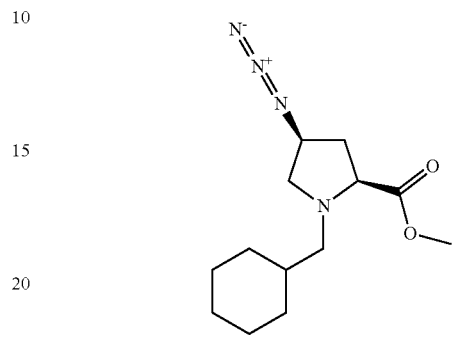

To a solution of (2S,4S)-4-azido-pyrrolidine-2-carboxylic acid methyl ester trifluoroacetate salt (9.6 g, 33.08 mmol) in 60 mL dichloromethane were added cyclohexanecarbaldehyde (2.6 g, 23.66 mmol), acetic acid (2.5 mL) and sodium triacetoxyborohydride (14.2 g, 66.16 mmol) and the reaction mixture was stirred at room temp. for 20 h. The reaction mixture was diluted with dichloromethane, washed with water, dried over anhydrous sodium sulfate and concentrated to give (2S,4S)-4-azido-1-cyclohexylmethyl-pyrrolidine-2-carboxylic acid methyl ester (11.2 g, crude) as a light brown liquid. The compound was used in the next step without further purification. MS calcd. for $C_{13}H_{23}N_4O_2$ [(M+H)$^+$] 267.0, obsd. 267.2.

Step 5: Preparation of (2S,4S)-4-amino-1-cyclohexylmethyl-pyrrolidine-2-carboxylic acid methyl ester

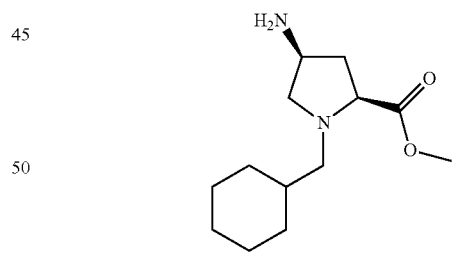

To a solution of (2S,4S)-4-azido-1-cyclohexylmethyl-pyrrolidine-2-carboxylic acid methyl ester (11.2 g, 42.1 mmol) in tetrahydrofuran (140 mL) were added triphenyl phosphine (22 g, 83.87 mmol) and water (1.9 mL) and the reaction mixture was refluxed at 75° C. for 6 h. The reaction mixture was diluted with ether, quenched with HCl (0.15 N), stirred for 5 min and extracted with ether. The aqueous layer was treated with sodium bicarbonate solution until pH~10 and then extracted with dichloromethane. The combined organic layers were dried over anhydrous sodium sulfate and concentrated to give (2S,4S)-4-amino-1-cyclohexylmethyl-pyrrolidine-2-carboxylic acid methyl ester (3 g, 29.6% yield) as a light yellow oil. The compound was used in the next step without further purification. MS calcd. for $C_{13}H_{25}N_2O_2$ [(M+H)$^+$] 241.0, obsd. 240.8.

Preparation of (2S,4S)-4-amino-1-cyclohexylmethyl-pyrrolidine-2-carboxylic acid ethyl ester

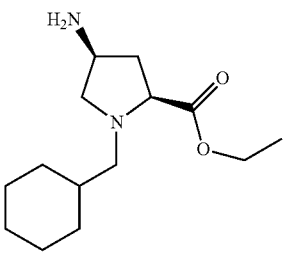 [SMILES: CCOC(=O)[C@@H]1C[C@H](N)CN1CC1CCCCC1]

(2S,4S)-4-Amino-1-cyclohexylmethyl-pyrrolidine-2-carboxylic acid ethyl ester was prepared from (2S,4S)-4-azido-pyrrolidine-2-carboxylic acid ethyl ester trifluoroacetate salt in a similar reaction sequence used in the preparation of (2S,4S)-4-amino-1-cyclohexylmethyl-pyrrolidine-2-carboxylic acid methyl ester. MS calcd. for $C_{14}H_{27}N_2O_2$ [(M+H)$^+$] 255, obsd. 255.

Preparation of (2S,4S)-4-amino-1-benzyl-pyrrolidine-2-carboxylic acid methyl ester

(2S,4S)-4-Amino-1-benzyl-pyrrolidine-2-carboxylic acid methyl ester was prepared from (2S,4S)-4-azido-pyrrolidine-2-carboxylic acid methyl ester trifluoroacetate salt in a similar reaction sequence used in the preparation of (2S,4S)-4-amino-1-cyclohexylmethyl-pyrrolidine-2-carboxylic acid methyl ester. MS calcd. for $C_{13}H_{19}N_2O_2$ [(M+H)$^+$] 235, obsd. 235.

Preparation of (2S,4S)-4-amino-1-(3,3-dimethyl-butyl)-pyrrolidine-2-carboxylic acid methyl ester

(2S,4S)-4-Amino-1-(3,3-dimethyl-butyl)-pyrrolidine-2-carboxylic acid methyl ester was prepared from (2S,4S)-4-azido-pyrrolidine-2-carboxylic acid methyl ester trifluoroacetate salt in a similar reaction sequence used in the preparation of (2S,4S)-4-amino-1-cyclohexylmethyl-pyrrolidine-2-carboxylic acid methyl ester. MS calcd. for $C_{12}H_{25}N_2O_2$ [(M+H)$^+$] 229, obsd. 229.

Preparation of (2S,4S)-4-amino-1-cyclopentylmethyl-pyrrolidine-2-carboxylic acid ethyl ester

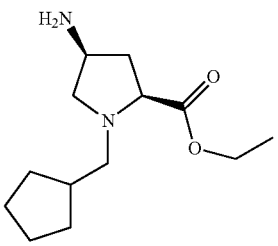 [SMILES: CCOC(=O)[C@@H]1C[C@H](N)CN1CC1CCCC1]

(2S,4S)-4-Amino-1-cyclopentylmethyl-pyrrolidine-2-carboxylic acid methyl ester was prepared from (2S,4S)-4-azido-pyrrolidine-2-carboxylic acid ethyl ester trifluoroacetate salt in a similar reaction sequence used in the preparation of (2S,4S)-4-amino-1-cyclohexylmethyl-pyrrolidine-2-carboxylic acid methyl ester. MS calcd. for $C_{13}H_{25}N_2O_2$ [(M+H)$^+$] 241, obsd. 241.

Preparation of (2S,4S)-4-amino-1-cyclobutylmethyl-pyrrolidine-2-carboxylic acid ethyl ester

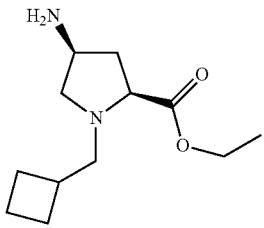 [SMILES: CCOC(=O)[C@@H]1C[C@H](N)CN1CC1CCC1]

(2S,4S)-4-Amino-1-cyclobutylmethyl-pyrrolidine-2-carboxylic acid ethyl ester was prepared from (2S,4S)-4-azido-pyrrolidine-2-carboxylic acid ethyl ester trifluoroacetate salt in a similar reaction sequence used in the preparation of (2S,4S)-4-amino-1-cyclohexylmethyl-pyrrolidine-2-carboxylic acid methyl ester. MS calcd. for $C_{12}H_{23}N_2O_2$ [(M+H)$^+$] 227, obsd. 227.

Preparation of (2S,4S)-4-amino-1-isobutyl-pyrrolidine-2-carboxylic acid ethyl ester

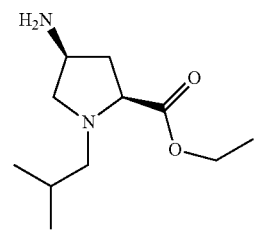

(2S,4S)-4-Amino-1-isobutyl-pyrrolidine-2-carboxylic acid ethyl ester was prepared from (2S,4S)-4-azido-pyrrolidine-2-carboxylic acid ethyl ester trifluoroacetate salt in a similar reaction sequence used in the preparation of (2S,4S)-

4-amino-1-cyclohexylmethyl-pyrrolidine-2-carboxylic acid methyl ester. MS calcd. for $C_{11}H_{23}N_2O_2$ [(M+H)$^+$] 215, obsd. 215.

Preparation of (2S,4S)-4-amino-1-cyclohexanecarbonyl-pyrrolidine-2-carboxylic acid ethyl ester

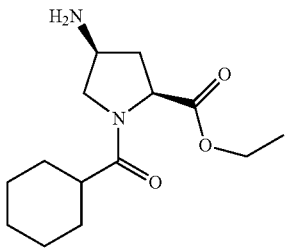 [SMILES: CCOC(=O)[C@@H]1C[C@H](N)CN1C(=O)C1CCCCC1]

(2S,4S)-4-Amino-1-cyclohexanecarbonyl-pyrrolidine-2-carboxylic acid ethyl ester was prepared from (2S,4S)-4-azido-pyrrolidine-2-carboxylic acid methyl ester trifluoroacetate salt in a similar reaction sequence used in the preparation of (2S,4S)-4-amino-1-cyclohexylmethyl-pyrrolidine-2-carboxylic acid methyl ester. MS calcd. for $C_{14}H_{25}N_2O_3$ [(M+H)$^+$] 269, obsd. 269.

Preparation of (2S,4R)-4-amino-1-cyclohexylmethyl-pyrrolidine-2-carboxylic acid methyl ester

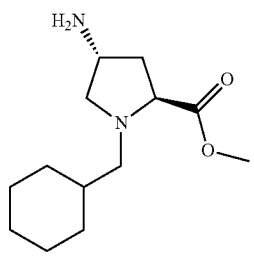 [SMILES: COC(=O)[C@@H]1C[C@@H](N)CN1CC1CCCCC1]

(2S,4R)-4-Amino-1-cyclohexylmethyl-pyrrolidine-2-carboxylic acid methyl ester was prepared from (2S,4S)-4-hydroxy-pyrrolidine-1,2-dicarboxylic acid 1-tert-butyl ester 2-methyl ester in a similar reaction sequence used in the preparation of (2S,4S)-4-amino-1-cyclohexylmethyl-pyrrolidine-2-carboxylic acid methyl ester. MS calcd. for $C_{13}H_{25}N_2O_2$ [(M+H)$^+$] 241, obsd. 241.

Preparation of (2R,4S)-4-amino-1-cyclohexylmethyl-pyrrolidine-2-carboxylic acid methyl ester

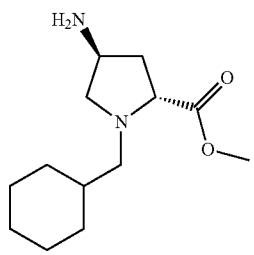 [SMILES: COC(=O)[C@H]1C[C@H](N)CN1CC1CCCCC1]

(2R,4S)-4-Amino-1-cyclohexylmethyl-pyrrolidine-2-carboxylic acid methyl ester was prepared from (2R,4R)-4-hydroxy-pyrrolidine-1,2-dicarboxylic acid 1-tert-butyl ester 2-methyl ester in a similar reaction sequence used in the preparation of (2S,4S)-4-amino-1-cyclohexylmethyl-pyrrolidine-2-carboxylic acid methyl ester. MS calcd. for $C_{13}H_{25}N_2O_2$ [(M+H)$^+$] 241, obsd. 241.

Preparation of (2S,4R)-4-amino-1-cyclohexylmethyl-piperidine-2-carboxylic acid methyl ester

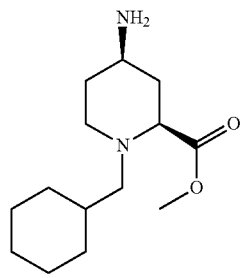 [SMILES: COC(=O)[C@@H]1C[C@H](N)CCN1CC1CCCCC1]

(2S,4R)-4-amino-1-cyclohexylmethyl-piperidine-2-carboxylic acid methyl ester was prepared from (2S,4S)-4-hydroxy-piperidine-1,2-dicarboxylic acid 1-tert-butyl ester 2-methyl ester in a similar reaction sequence used in the preparation of (2S,4S)-4-amino-1-cyclohexylmethyl-pyrrolidine-2-carboxylic acid methyl ester. MS calcd. for $C_{14}H_{27}N_2O_2$ [(M+H)$^+$] 255, obsd. 255.

Preparation of (2S,4S)-4-amino-2-oxazol-2-yl-pyrrolidine-1-carboxylic acid benzyl ester

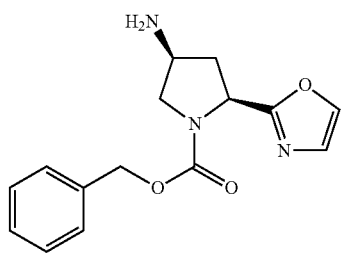 [SMILES: N[C@H]1C[C@@H](c2ncco2)N(C(=O)OCc2ccccc2)C1]

Step 1: Preparation of (2S,4R)-4-tert-butoxy-2-(2,2-dimethoxy-ethylcarbamoyl)-pyrrolidine-1-carboxylic acid benzyl ester

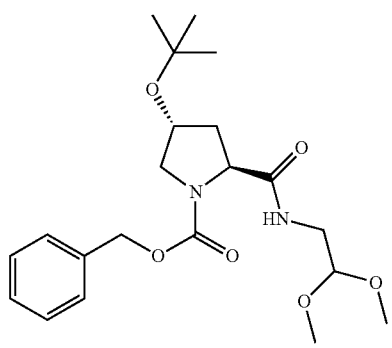 [SMILES: COC(CNC(=O)[C@@H]1C[C@@H](OC(C)(C)C)CN1C(=O)OCc1ccccc1)OC]

To a stirred solution of (2S,4R)-4-tert-butoxy-pyrrolidine-1,2-dicarboxylic acid 1-benzyl ester (500 mg, 1.56 mmol) and 2,2-dimethoxy-ethylamine (163 mg, 1.56 mmol) in dichloromethane (5 mL) were added EDC·HCl (298 mg, 1.56 mmol), HOBt (210 mg, 1.56 mmol) and triethylamine (157 mg, 1.56 mmol). The mixture was stirred at room temp. for 24 h, diluted with water, extracted with ethyl acetate and washed with water and brine. The organic layer was dried over anhydrous sodium sulfate, filtered, concentrated and purified by column chromatography (using 15% EtOAc in hexane as eluent) to give (2S,4R)-4-tert-butoxy-2-(2,2-dimethoxy-ethylcarbamoyl)-pyrrolidine-1-carboxylic acid benzyl ester (200 mg, 31.6% yield) as a light brown liquid. MS calcd. for $C_{21}H_{33}N_2O_6$ [(M+H)$^+$] 409.0, obsd. 409.0.

Step 2: Preparation of (2S,4R)-4-tert-butoxy-2-(2-oxo-ethylcarbamoyl)-pyrrolidine-1-carboxylic acid benzyl ester

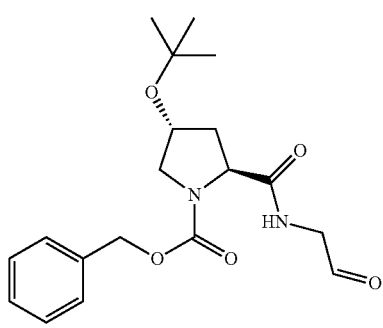 [SMILES: CC(C)(C)O[C@@H]1C[C@@H](C(=O)NCC=O)N(C(=O)OCc2ccccc2)C1]

A mixture of (2S,4R)-4-tert-butoxy-2-(2,2-dimethoxy-ethylcarbamoyl)-pyrrolidine-1-carboxylic acid benzyl ester (1.8 g, 4.41 mmol) and HCl (1M, 30 mL) in acetone (30 mL) was stirred at room temp. for 8 h. The reaction mixture was then extracted with ethyl acetate and washed with water and brine. The organic layer was dried over anhydrous sodium sulfate, filtered and concentrated to give (2S,4R)-4-tert-butoxy-2-(2-oxo-ethylcarbamoyl)-pyrrolidine-1-carboxylic acid benzyl ester (1.4 g, crude) as a sticky liquid. The compound was used in the next step without further purification. MS calcd. for $C_{19}H_{27}N_2O_5$ [(M+H)$^+$]363.0, obsd. 363.2.

Step 3: Preparation of (2S,4R)-4-tert-butoxy-2-oxazol-2-yl-pyrrolidine-1-carboxylic acid benzyl ester

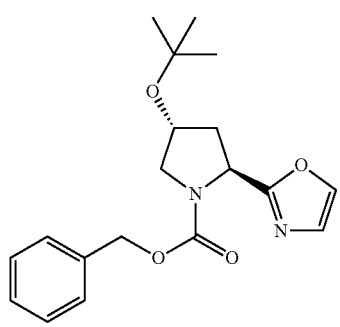 [SMILES: CC(C)(C)O[C@@H]1C[C@@H](c2ncco2)N(C(=O)OCc2ccccc2)C1]

To a stirred solution of (2S,4R)-4-tert-butoxy-2-(2-oxo-ethylcarbamoyl)-pyrrolidine-1-carboxylic acid benzyl ester (4.5 g, 12.43 mmol) and hexachloroethane (5.88 g, 24.86 mmol) in dichloromethane (30 mL) was added triphenyl phosphine (6.52 g, 24.86 mmol) The mixture was stirred at 0° C. for 15 min, triethylamine (2.5 g, 24.86 mmol) was then added and the mixture was stirred at room temp. for 14 h. The reaction mixture was then extracted with dichloromethane and washed with water and brine. The organic layer was dried over anhydrous sodium sulfate and concentrated. The residue was purified by column chromatography (using 15% EtOAc in hexane as eluent) to give (2S,4R)-4-tert-butoxy-2-oxazol-2-yl-pyrrolidine-1-carboxylic acid benzyl ester (2 g, 46.6% yield) as a yellow liquid. MS calcd. for $C_{19}H_{25}N_2O_4$ [(M+H)$^+$] 345.0, obsd. 345.2.

Step 4-7: Preparation of (2S,4S)-4-amino-2-oxazol-2-yl-pyrrolidine-1-carboxylic acid benzyl ester

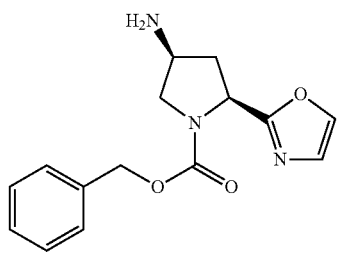 [SMILES: N[C@H]1C[C@@H](c2ncco2)N(C(=O)OCc2ccccc2)C1]

(2S,4S)-4-Amino-2-oxazol-2-yl-pyrrolidine-1-carboxylic acid benzyl ester was prepared from (2S,4R)-4-tert-butoxy-2-oxazol-2-yl-pyrrolidine-1-carboxylic acid benzyl ester in a similar reaction sequence used in the preparation of (2S,4S)-4-amino-1-cyclohexylmethyl-pyrrolidine-2-carboxylic acid methyl ester. MS calcd. for $C_{15}H_{18}N_3O_3$ [(M+H)$^+$] 288, obsd. 288.

Preparation of (2S,4S)-4-amino-2-(5-methyl-oxazol-2-yl)-pyrrolidine-1-carboxylic acid benzyl ester

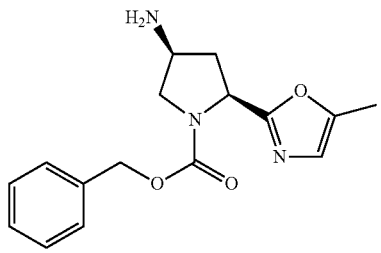 [SMILES: Cc1cnc([C@@H]2C[C@H](N)CN2C(=O)OCc2ccccc2)o1]

Step 1: Preparation of (2S,4R)-4-tert-butoxy-2-(2-oxo-propylcarbamoyl)-pyrrolidine-1-carboxylic acid benzyl ester

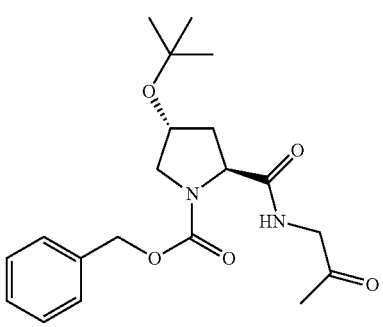 [SMILES: CC(=O)CNC(=O)[C@@H]1C[C@@H](OC(C)(C)C)CN1C(=O)OCc1ccccc1]

To a stirred solution of (2S,4R)-4-tert-butoxy-pyrrolidine-1,2-dicarboxylic acid 1-benzyl ester (10.78 g, 33.54 mmol) and 1-amino-propan-2-one (2.45 g, crude, 33.54 mmol) in dichlormethane (56 mL) were added EDC.HCl (6.405 g, 33.54 mmol), HOBt (5.128 g, 33.54 mmol) and triethylamine (12.67 mL, 100.62 mmol). The mixture was stirred at room temp. for 24 h. The reaction mixture was then diluted with water, extracted with dichloromethane and washed with water and brine. The organic layer was dried over anhydrous sodium sulfate, filtered and concentrated. The crude was then purified by column chromatography to give (2S,4R)-4-tert-butoxy-2-(2-oxo-propylcarbamoyl)-pyrrolidine-1-carboxylic acid benzyl ester (7 g, 55.4% yield) as a light brown liquid. MS calcd. for $C_{20}H_{29}N_2O_5$ [(M+H)$^+$] 377.0, obsd. 377.4.

Step 2: Preparation of (2S,4R)-4-tert-butoxy-2-(5-methyl-oxazol-2-yl)-pyrrolidine-1-carboxylic acid benzyl ester

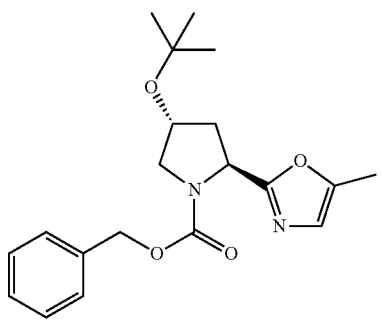 [SMILES: Cc1cnc([C@@H]2C[C@@H](OC(C)(C)C)CN2C(=O)OCc2ccccc2)o1]

To a stirred solution of (2S,4R)-4-tert-butoxy-2-(2-oxo-propylcarbamoyl)-pyrrolidine-1-carboxylic acid benzyl ester (2.5 g, 6.65 mmol) and hexachloroethane (3.148 g, 13.3 mmol) in dichloromethane (16 mL) was added triphenyl phosphine (3.458 g, 13.3 mmol). The mixture was stirred at 0° C. for 20 min. Then triethylamine (1.36 mL, 13.3 mmol) was added and the reaction mixture was stirred at room temp. for 14 h. Water was then added to the reaction mixture, extracted with dichloromethane and the combined organic layer was washed with water and brine. The organic layer was dried over anhydrous sodium sulfate and concentrated. The crude was then purified by column chromatography to give (2S,4R)-4-tert-butoxy-2-(5-methyl-oxazol-2-yl)-pyrrolidine-1-carboxylic acid benzyl ester (1 g, 42% yield) as an off-white solid. MS calcd. for $C_{20}H_{27}N_2O_4$ [(M+H)$^+$] 359.0, obsd. 359.0.

Step 3: Preparation of (2S,4R)-4-hydroxy-2-(5-methyl-oxazol-2-yl)-pyrrolidine-1-carboxylic acid benzyl ester

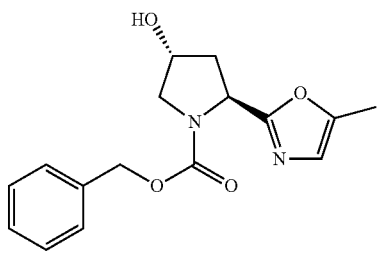 [SMILES: Cc1cnc([C@@H]2C[C@@H](O)CN2C(=O)OCc2ccccc2)o1]

To a stirred solution of (2S,4R)-4-tert-butoxy-2-(5-methyl-oxazol-2-yl)-pyrrolidine-1-carboxylic acid benzyl ester (2 g, 5.59 mmol) in dichloromethane (15 mL) was added trifluoroacetic acid (1.57 mL) in dichloromethane (1:5) at 0° C. and the mixture was then stirred at room temp. for 16 h. The reaction mixture was neutralized with saturated sodium bicarbonate solution and extracted with dichloromethane. The organic layer was washed with brine, dried over anhydrous sodium sulfate and concentrated under reduced pressure. The crude was then purified by column chromatography to give (2S,4R)-4-hydroxy-2-(5-methyl-oxazol-2-yl)-pyrrolidine-1-carboxylic acid benzyl ester (1.1 g, 65.1% yield) as an off white solid. MS calcd. for $C_{16}H_{19}N_2O_4$ [(M+H)$^+$] 303.0, obsd. 303.4.

Step 4-6: Preparation of (2S,4S)-4-amino-2-(5-methyl-oxazol-2-yl)-pyrrolidine-1-carboxylic acid benzyl ester

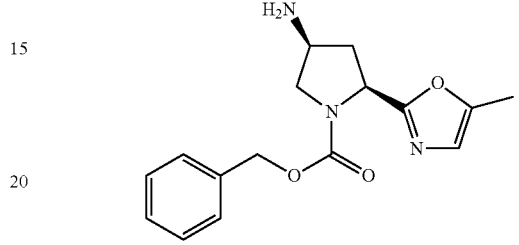

(2S,4S)-4-Amino-2-(5-methyl-oxazol-2-yl)-pyrrolidine-1-carboxylic acid benzyl ester was prepared from (2S,4R)-4-hydroxy-2-(5-methyl-oxazol-2-yl)-pyrrolidine-1-carboxylic acid benzyl ester in a similar reaction sequence used in the preparation of (2S,4S)-4-amino-2-oxazol-2-yl-pyrrolidine-1-carboxylic acid benzyl ester. MS calcd. for $C_{16}H_{20}N_3O_3$ [(M+H)$^+$] 302, obsd. 302.

Preparation of (2S,4S)-4-amino-2-(5-tert-butyl-oxazol-2-yl)-pyrrolidine-1-carboxylic acid benzyl ester

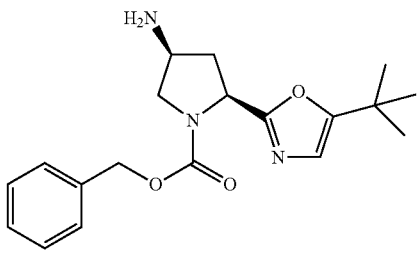 [SMILES: CC(C)(C)c1cnc([C@@H]2C[C@H](N)CN2C(=O)OCc2ccccc2)o1]

(2S,4S)-4-Amino-2-(5-tert-butyl-oxazol-2-yl)-pyrrolidine-1-carboxylic acid benzyl ester was prepared from (2S,4R)-4-tert-butoxy-pyrrolidine-1,2-dicarboxylic acid 1-benzyl ester in a similar reaction sequence used in the preparation of (2S,4S)-4-amino-2-oxazol-2-yl-pyrrolidine-1-carboxylic acid benzyl ester. MS calcd. for $C_{19}H_{26}N_3O_3$ [(M+H)$^+$] 344, obsd. 344.

Preparation of (2S,4S)-4-amino-2-(5-phenyl-oxazol-2-yl)-pyrrolidine-1-carboxylic acid benzyl ester

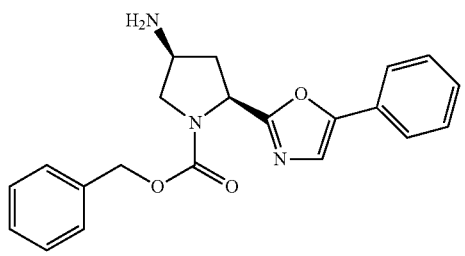 [SMILES: N[C@H]1C[C@@H](c2ncc(-c3ccccc3)o2)N(C(=O)OCc2ccccc2)C1]

(2S,4S)-4-amino-2-(5-phenyl-oxazol-2-yl)-pyrrolidine-1-carboxylic acid benzyl ester was prepared from (2S,4R)-4-tert-butoxy-pyrrolidine-1,2-dicarboxylic acid 1-benzyl ester in a similar reaction sequence used in the preparation of (2S,4S)-4-amino-2-oxazol-2-yl-pyrrolidine-1-carboxylic acid benzyl ester. MS calcd. for $C_{21}H_{22}N_3O_3$ [(M+H)$^+$] 364, obsd. 364.

Preparation of (2S,4S)-4-amino-2-benzooxazol-2-yl-pyrrolidine-1-carboxylic acid benzyl ester

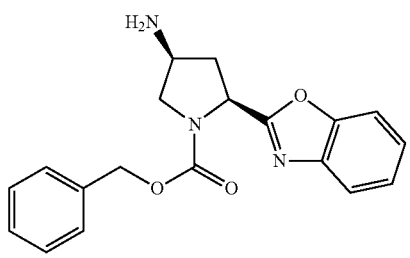 [SMILES: N[C@H]1C[C@@H](c2nc3ccccc3o2)N(C(=O)OCc2ccccc2)C1]

Step 1: Preparation of (2S,4R)-2-(2-bromo-phenyl-carbamoyl)-4-tert-butoxy-pyrrolidine-1-carboxylic acid benzyl ester

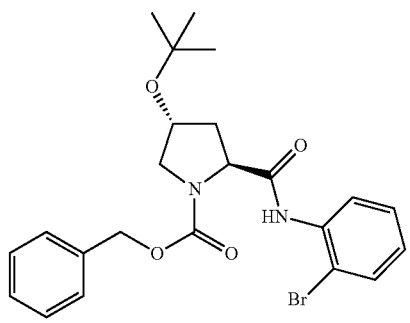 [SMILES: CC(C)(C)O[C@@H]1C[C@@H](C(=O)Nc2ccccc2Br)N(C(=O)OCc2ccccc2)C1]

(2S,4R)-2-(2-Bromo-phenylcarbamoyl)-4-tert-butoxy-pyrrolidine-1-carboxylic acid benzyl ester (290 mg, 19.6% purity) was synthesized from 1 g of (2S,4R)-4-tert-butoxy-pyrrolidine-1,2-dicarboxylic acid 1-benzyl ester following the procedures described for (2S,4R)-4-tert-butoxy-2-(2-oxo-propylcarbamoyl)-pyrrolidine-1-carboxylic acid benzyl ester.

Step 2: Preparation of (2S,4R)-2-benzooxazol-2-yl-4-tert-butoxy-pyrrolidine-1-carboxylic acid benzyl ester

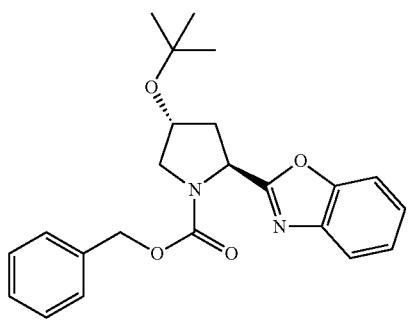 [SMILES: CC(C)(C)O[C@@H]1C[C@@H](c2nc3ccccc3o2)N(C(=O)OCc2ccccc2)C1]

To a stirred solution of (2S,4R)-2-(2-bromo-phenylcarbamoyl)-4-tert-butoxy-pyrrolidine-1-carboxylic acid benzyl ester (900 mg, 1.89 mmol) in DME (20 mL) at 25° C. in a sealed tube were added CuI (36 mg, 0.19 mmol), 1,10-phenanthraline (68 mg, 0.38 mmol), and $Cs_2CO_3$ (1.847 g, 5.68 mmol). The reaction mixture was refluxed for 14 h. After completion of reaction, water was added, and the mixture was then extracted with dichloromethane. The organic layer was washed with brine, dried over anhydrous sodium sulfate, filtered and concentrated under reduced pressure. The crude was then purified by column chromatography to give (2S,4R)-2-benzooxazol-2-yl-4-tert-butoxy-pyrrolidine-1-carboxylic acid benzyl ester (430 mg, 57.5% yield) as a yellowish liquid. MS calcd. for $C_{23}H_{27}N_2O_4$ [(M+H)$^+$] 395, obsd. 395.

Step 3-6: Preparation of (2S,4S)-4-amino-2-benzooxazol-2-yl-pyrrolidine-1-carboxylic acid benzyl ester

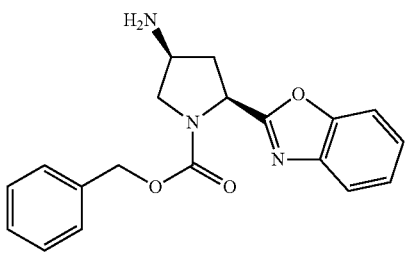 [SMILES: N[C@H]1C[C@@H](c2nc3ccccc3o2)N(C(=O)OCc2ccccc2)C1]

(2S,4S)-4-amino-2-benzooxazol-2-yl-pyrrolidine-1-carboxylic acid benzyl ester was prepared from (2S,4R)-2-benzooxazol-2-yl-4-tert-butoxy-pyrrolidine-1-carboxylic acid benzyl ester in a similar reaction sequence used in the preparation of (2S,4S)-4-amino-2-oxazol-2-yl-pyrrolidine-1-carboxylic acid benzyl ester. MS calcd. for $C_{19}H_{20}N_3O_3$ [(M+H)$^+$] 338, obsd. 338.

Preparation of (2S,4S)-4-amino-1-cyclohexylmethyl-2-methyl-pyrrolidine-2-carboxylic acid methyl ester

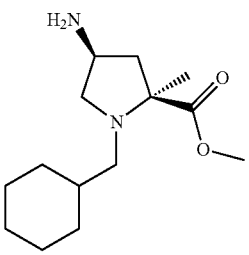 [SMILES: COC(=O)[C@]1(C)C[C@H](N)CN1CC1CCCCC1]

Step 1: Preparation of (2S,4R)-4-hydroxy-2-methyl-pyrrolidine-1,2-dicarboxylic acid 1-tert-butyl ester 2-methyl ester

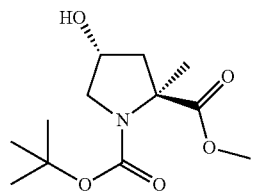 [SMILES: COC(=O)[C@]1(C)C[C@@H](O)CN1C(=O)OC(C)(C)C]

To a solution of (2S,4R)-4-hydroxy-pyrrolidine-1,2-dicarboxylic acid 1-tert-butyl ester 2-methyl ester (500 mg, 2.04 mmol) and MeI (1.2 g, 8.45 mmol) in tetrahydrofuran at −40° C. was added a solution of lithium diisopropylamide in tetrahydrofuran (1.5M solution, 5 mL, 7.47 mmol). The reaction mixture was warmed to room temp. and stirred for 4 h. After completion of reaction, the mixture was re-cooled to −30° C. and quenched with saturated aqueous ammonium chloride. The reaction mixture was then extracted with ethyl acetate and washed with water and brine. The organic layer was dried over anhydrous sodium sulfate, filtered and concentrated. The crude was purified by preparative HPLC to give two stereoisomers; (2S,4R)-4-hydroxy-2-methyl-pyrrolidine-1,2-dicarboxylic acid 1-tert-butyl ester 2-methyl ester (200 mg, 37.7% yield) and (2R,4R)-4-hydroxy-2-methyl-pyrrolidine-1,2-dicarboxylic acid 1-tert-butyl ester 2-methyl ester (100 mg, 18.9% yield). MS calcd. for $C_{12}H_{22}NO_5$ [(M+H)$^+$] 260, obsd. 260.

Steps 2-5: Preparation of (2S,4S)-4-amino-1-cyclohexylmethyl-2-methyl-pyrrolidine-2-carboxylic acid methyl ester

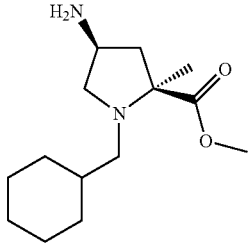 [SMILES: COC(=O)[C@]1(C)C[C@H](N)CN1CC1CCCCC1]

(2S,4S)-4-Amino-1-cyclohexylmethyl-2-methyl-pyrrolidine-2-carboxylic acid methyl ester was prepared from (2S,4R)-4-hydroxy-2-methyl-pyrrolidine-1,2-dicarboxylic acid 1-tert-butyl ester 2-methyl ester in a similar reaction sequence used in the preparation of (2S,4S)-4-amino-1-cyclohexylmethyl-pyrrolidine-2-carboxylic acid methyl ester.

Example 1

(2S,4S)-1-Cyclohexylmethyl-4-[(1-hydroxy-naphthalene-2-carbonyl)-amino]-pyrrolidine-2-carboxylic acid methyl ester

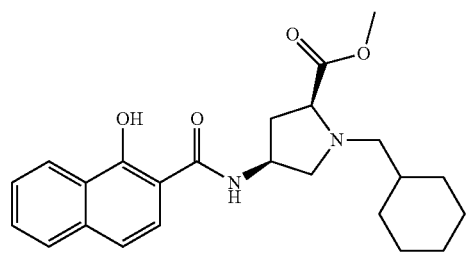

To a stirred solution of (2S,4S)-4-amino-1-cyclohexylmethyl-pyrrolidine-2-carboxylic acid methyl ester (150 mg, 0.62 mmol) and 1-hydroxy-naphthalene-2-carboxylic acid (90 mg, 0.75 mmol) in DMF (2 mL) were added HATU (285 mg, 0.75 mmol) and N,N-diisopropylethylamine (96 mg, 0.75 mmol). The mixture was stirred at room temp. for 24 h. The reaction mixture was then extracted with ethyl acetate and washed with water and brine. The organic layer was then dried over anhydrous sodium sulfate, concentrated and purified by column chromatography to give (2S,4S)-1-cyclohexylmethyl-4-[(1-hydroxy-naphthalene-2-carbonyl)-amino]-pyrrolidine-2-carboxylic acid methyl ester. MS calcd. for $C_{24}H_{31}N_2O_4$ [(M+H)$^+$] 411.0, obsd. 411.0.

Example 2

(2S,4S)-1-Benzyl-4-[(1-hydroxy-naphthalene-2-carbonyl)-amino]-pyrrolidine-2-carboxylic acid methyl ester

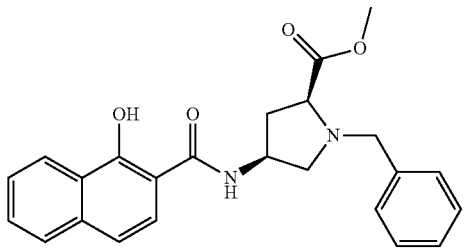 [SMILES: COC(=O)[C@@H]1C[C@H](NC(=O)c2ccc3ccccc3c2O)CN1Cc1ccccc1]

(2S,4S)-1-Benzyl-4-[(1-hydroxy-naphthalene-2-carbonyl)-amino]-pyrrolidine-2-carboxylic acid methyl ester was prepared from (2S,4S)-4-amino-1-benzyl-pyrrolidine-2-carboxylic acid methyl ester and 1-hydroxy-naphthalene-2-carboxylic acid in an analogous manner to example 1. MS calcd. for $C_{24}H_{25}N_2O_4$ [(M+H)$^+$] 405.0, obsd. 405.0.

Example 3

(2S,4S)-1-(3,3-Dimethyl-butyl)-4-[(1-hydroxy-naphthalene-2-carbonyl)-amino]-pyrrolidine-2-carboxylic acid methyl ester

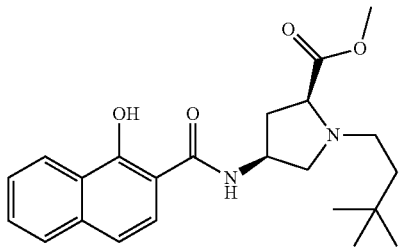 [SMILES: COC(=O)[C@@H]1C[C@H](NC(=O)c2ccc3ccccc3c2O)CN1CCC(C)(C)C]

(2S,4S)-1-(3,3-Dimethyl-butyl)-4-[(1-hydroxy-naphthalene-2-carbonyl)-amino]-pyrrolidine-2-carboxylic acid methyl ester was prepared from (2S,4S)-4-amino-1-(3,3-dimethyl-butyl)-pyrrolidine-2-carboxylic acid methyl ester and 1-hydroxy-naphthalene-2-carboxylic acid in an analogous manner to example 1. MS calcd. for $C_{23}H_{31}N_2O_4$ [(M+H)$^+$] 399.0, obsd. 399.0.

Example 4

(2S,4S)-1-Cyclopentylmethyl-4-[(1-hydroxy-naphthalene-2-carbonyl)-amino]-pyrrolidine-2-carboxylic acid ethyl ester

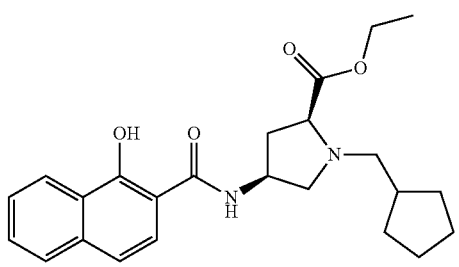 [SMILES: CCOC(=O)[C@@H]1C[C@H](NC(=O)c2ccc3ccccc3c2O)CN1CC1CCCC1]

(2S,4S)-1-Cyclopentylmethyl-4-[(1-hydroxy-naphthalene-2-carbonyl)-amino]-pyrrolidine-2-carboxylic acid ethyl ester was prepared from (2S,4S)-4-amino-1-cyclopentylmethyl-pyrrolidine-2-carboxylic acid ethyl ester and 1-hydroxy-naphthalene-2-carboxylic acid in an analogous manner to example 1. MS calcd. for $C_{24}H_{31}N_2O_4$ [(M+H)$^+$] 411.0, obsd. 411.2.

Example 5

(2S,4S)-1-Cyclobutylmethyl-4-[(1-hydroxy-naphthalene-2-carbonyl)-amino]-pyrrolidine-2-carboxylic acid ethyl ester

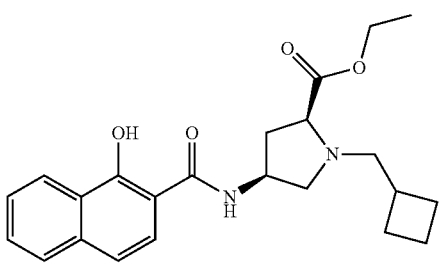 [SMILES: CCOC(=O)[C@@H]1C[C@H](NC(=O)c2ccc3ccccc3c2O)CN1CC1CCC1]

(2S,4S)-1-Cyclobutylmethyl-4-[(1-hydroxy-naphthalene-2-carbonyl)-amino]-pyrrolidine-2-carboxylic acid ethyl ester was prepared from (2S,4S)-4-amino-1-cyclobutylmethyl-pyrrolidine-2-carboxylic acid ethyl ester and 1-hydroxy-naphthalene-2-carboxylic acid in an analogous manner to example 1. MS calcd. for $C_{23}H_{29}N_2O_4$ [(M+H)$^+$] 397.0, obsd. 397.2.

Example 6

(2S,4S)-4-[(1-Hydroxy-naphthalene-2-carbonyl)-amino]-1-isobutyl-pyrrolidine-2-carboxylic acid ethyl ester

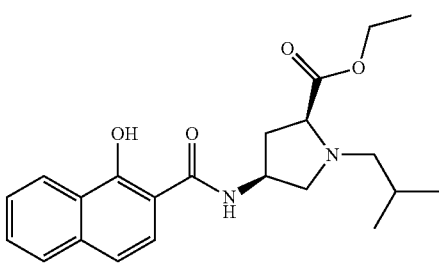 [SMILES: CCOC(=O)[C@@H]1C[C@H](NC(=O)c2ccc3ccccc3c2O)CN1CC(C)C]

(2S,4S)-4-[(1-Hydroxy-naphthalene-2-carbonyl)-amino]-1-isobutyl-pyrrolidine-2-carboxylic acid ethyl ester was prepared from (2S,4S)-4-amino-1-isobutyl-pyrrolidine-2-carboxylic acid ethyl ester and 1-hydroxy-naphthalene-2-carboxylic acid in an analogous manner to example 1. MS calcd. for $C_{22}H_{29}N_2O_4$ [(M+H)$^+$] 385.0, obsd. 385.4.

Example 7

(2S,4S)-1-Cyclohexanecarbonyl-4-[(1-hydroxy-naphthalene-2-carbonyl)-amino]-pyrrolidine-2-carboxylic acid ethyl ester

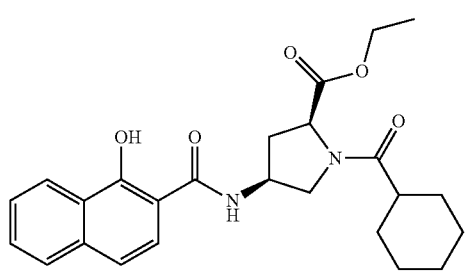 [SMILES: CCOC(=O)[C@@H]1C[C@H](NC(=O)c2ccc3ccccc3c2O)CN1C(=O)C1CCCCC1]

(2S,4S)-1-Cyclohexanecarbonyl-4-[(1-hydroxy-naphthalene-2-carbonyl)-amino]pyrrolidine-2-carboxylic acid ethyl ester was prepared (2S,4S)-4-amino-1-cyclohexanecarbonyl-pyrrolidine-2-carboxylic acid ethyl ester and 1-hydroxy-naphthalene-2-carboxylic acid in an analogous manner to example 1. MS calcd. for $C_{25}H_{31}N_2O_5$ [(M+H)$^+$] 439.0, obsd. 439.4.

Example 8

(2S,4S)-1-Cyclohexylmethyl-4-[(1-hydroxy-naphthalene-2-carbonyl)-amino]-pyrrolidine-2-carboxylic acid ethyl ester

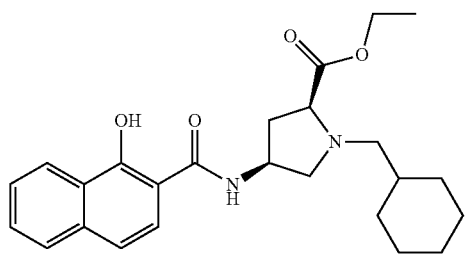

Step 1: Preparation of (2S,4S)-1-cyclohexylmethyl-4-[(1-hydroxy-naphthalene-2-carbonyl)-amino]-pyrrolidine-2-carboxylic acid

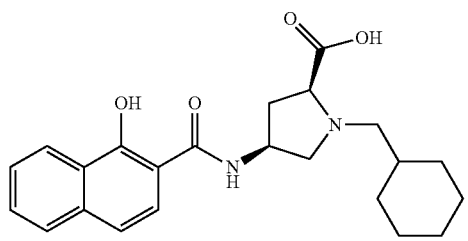

To a stirred solution of (2S,4S)-1-cyclohexylmethyl-4-[(1-hydroxy-naphthalene-2-carbonyl)-amino]-pyrrolidine-2-carboxylic acid methyl ester (350 mg, 0.85 mmol) in methanol (8 mL) was added lithium hydroxide (204 mg, 8.53 mmol) and the mixture was stirred at room temp. for 24 h. The reaction mixture was then acidified with dilute hydrochloric acid, extracted with ethyl acetate and washed with water and brine. The organic layer was dried over anhydrous sodium sulfate, filtered, concentrated and purified by column chromatography (using 15% EtOAc in hexane as eluent) to give (2S,4S)-1-cyclohexylmethyl-4-[(1-hydroxy-naphthalene-2-carbonyl)-amino]pyrrolidine-2-carboxylic acid (250 mg, 74.0% yield) as a white solid. MS calcd. for $C_{23}H_{29}N_2O_4$ [(M+H)$^+$] 397.0, obsd. 397.6.

Step 2: (2S,4S)-1-Cyclohexylmethyl-4-[(1-hydroxy-naphthalene-2-carbonyl)-amino]-pyrrolidine-2-carboxylic acid ethyl ester

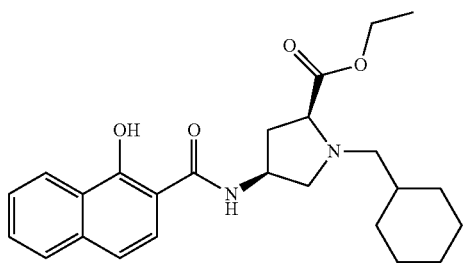 [SMILES: CCOC(=O)[C@@H]1C[C@H](NC(=O)c2ccc3ccccc3c2O)CN1CC1CCCCC1]

To a stirred solution of (2S,4S)-1-cyclohexylmethyl-4-[(1-hydroxy-naphthalene-2-carbonyl)-amino]-pyrrolidine-2-carboxylic acid (50 mg, 0.13 mmol) in ethanol (3 mL) was added conc. sulfuric acid (0.1 mL) and the reaction mixture was stirred at 95° C. for 14 h. The reaction mixture was then concentrated under vacuum, diluted with water, extracted with ethyl acetate and washed with water and brine. The organic layer was dried over anhydrous sodium sulfate, filtered, concentrated and purified by column chromatography (using 5% EtOAc in hexane as eluent) to give (2S,4S)-1-cyclohexylmethyl-4-[(1-hydroxy-naphthalene-2-carbonyl)-amino]-pyrrolidine-2-carboxylic acid ethyl ester (28 mg, 52.3% yield) as a blue sticky liquid. MS calcd. for $C_{25}H_{33}N_2O_4$ [(M+H)$^+$] 425.0, obsd. 425.2.

Example 9

(2S,4S)-1-Cyclohexylmethyl-4-[(1-hydroxy-naphthalene-2-carbonyl)-amino]-pyrrolidine-2-carboxylic acid tert-butyl ester

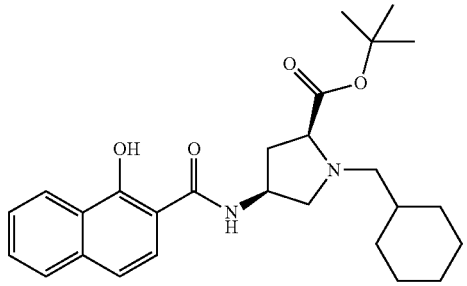 [SMILES: CC(C)(C)OC(=O)[C@@H]1C[C@H](NC(=O)c2ccc3ccccc3c2O)CN1CC1CCCCC1]

A mixture of (2S,4S)-1-cyclohexylmethyl-4-[(1-hydroxy-naphthalene-2-carbonyl)-amino]-pyrrolidine-2-carboxylic acid (50 mg, 0.13 mmol) and 2,2,2-trichloro-acetimidic acid tert-butyl ester (70 mg, 0.33 mmol) in THF (1 mL) was stirred at 0° C. for several minutes. Then BF$_3$.OEt$_2$ (20 mg, 0.13 mmol) was added dropwise at 0° C. and the reaction mixture was warmed to room temp. and stirred for 2 h. The reaction mixture was then quenched with brine solution, extracted with ethyl acetate and washed with water and brine. The organic layer was dried over anhydrous sodium sulfate, concentrated and purified by column chromatography (using 5% EtOAc in hexane as eluent) to give (2S,4S)-1-cyclohexylmethyl-4-[(1-hydroxy-naphthalene-2-carbonyl)-amino]-pyrrolidine-2-carboxylic acid tert-butyl ester (20 mg, 35.0% yield) as a bluish sticky liquid. MS calcd. for $C_{27}H_{37}N_2O_4$ [(M+H)$^+$] 453.0, obsd. 453.2.

Example 10

(2S,4S)-1-Cyclohexylmethyl-4-[(1-hydroxy-naphthalene-2-carbonyl)-amino]-pyrrolidine-2-carboxylic acid ethylamide

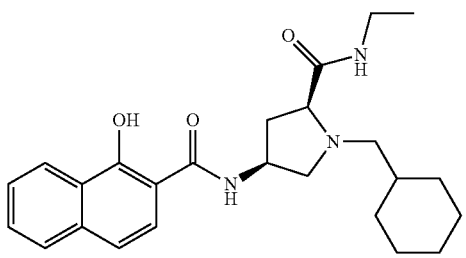 [SMILES: CCNC(=O)[C@@H]1C[C@H](NC(=O)c2ccc3ccccc3c2O)CN1CC1CCCCC1]

(2S,4S)-1-Cyclohexylmethyl-4-[(1-hydroxy-naphthalene-2-carbonyl)-amino]-pyrrolidine-2-carboxylic acid ethylamide was prepared from (2S,4S)-1-cyclohexylmethyl-4-[(1-hydroxy-naphthalene-2-carbonyl)-amino]-pyrrolidine-2-carboxylic acid and ethylamine in an analogous manner to example 1. MS calcd. for $C_{25}H_{34}N_3O_3$ [(M+H)$^+$] 424.0, obsd. 424.0.

Example 11

1-Hydroxy-naphthalene-2-carboxylic acid [(3S,5S)-5-(azetidine-1-carbonyl)-1-cyclohexylmethyl-pyrrolidin-3-yl]-amide

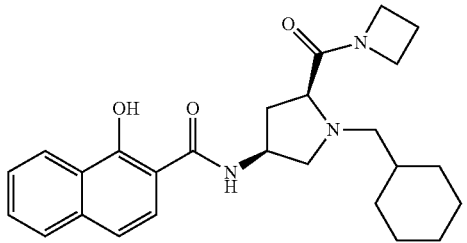 [SMILES: O=C(N[C@H]1C[C@@H](C(=O)N2CCC2)N(CC2CCCCC2)C1)c1ccc2ccccc2c1O]

Hydroxy-naphthalene-2-carboxylic acid [(3S,5S)-5-(azetidine-1-carbonyl)-1-cyclohexylmethyl-pyrrolidin-3-yl]-amide was prepared from (2S,4S)-1-cyclohexylmethyl-4-[(1-hydroxy-naphthalene-2-carbonyl)-amino]-pyrrolidine- 2-carboxylic acid and azetidine in an analogous manner to example 1. MS calcd for $C_{26}H_{34}N_3O_3$ [(M+H)$^+$] 436.0, obsd. 436.0.

Example 12

(2S,4S)-1-Cyclohexylmethyl-4-[(1-hydroxy-naphthalene-2-carbonyl)-amino]-pyrrolidine-2-carboxylic acid propylamide

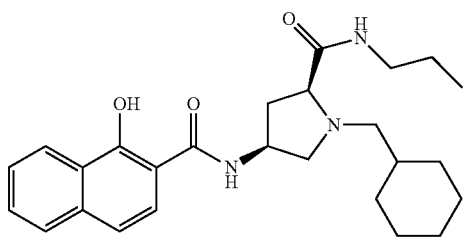 [SMILES: CCCNC(=O)[C@@H]1C[C@H](NC(=O)c2ccc3ccccc3c2O)CN1CC1CCCCC1]

To a mixture of (2S,4S)-1-cyclohexylmethyl-4-[(1-hydroxy-naphthalene-2-carbonyl)-amino]-pyrrolidine-2-carboxylic acid methyl ester (150 mg, 0.37 mmol) and 44 mg of n-propyl amine was added Me$_3$Al (catalytic amount, 2M in toluene) under an argon atmosphere in a seal tube and the mixture was heated at 100° C. for 16 hr. The reaction mixture was then quenched with water and extracted with ethyl acetate. The organic layer was dried over anhydrous sodium sulfate and concentrated. The crude was then purified by silica gel column chromatography to give (2S,4S)-1-cyclohexylmethyl-4-[(1-hydroxy-naphthalene-2-carbonyl)-amino]-pyrrolidine-2-carboxylic acid propylamide (30 mg, 18.7% yield) as a white solid. MS calcd. for $C_{26}H_{36}N_3O_3$ [(M+H)$^+$] 438.0, obsd. 438.2.

Example 13

(2S,4S)-1-Cyclohexylmethyl-4-[(1-hydroxy-naphthalene-2-carbonyl)-amino]-pyrrolidine-2-carboxylic acid isopropylamide

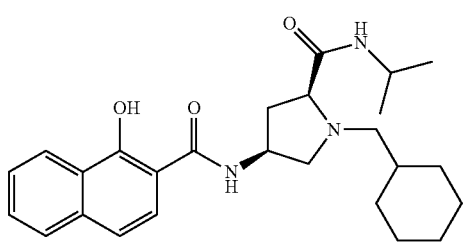 [SMILES: CC(C)NC(=O)[C@@H]1C[C@H](NC(=O)c2ccc3ccccc3c2O)CN1CC1CCCCC1]

(2S,4S)-1-Cyclohexylmethyl-4-[(1-hydroxy-naphthalene-2-carbonyl)-amino]-pyrrolidine-2-carboxylic acid isopropylamide was prepared from (2S,4S)-1-cyclohexylmethyl-4-[(1-hydroxy-naphthalene-2-carbonyl)-amino]-pyrrolidine-2-carboxylic acid methyl ester and isopropylamine in an analogous manner to example 12. MS calcd. for $C_{26}H_{36}N_3O_3$ [(M+H)$^+$] 438.0, obsd. 437.8.

Example 14

(2S,4S)-1-Cyclohexylmethyl-4-[(1-hydroxy-naphthalene-2-carbonyl)-amino]-pyrrolidine-2-carboxylic acid benzylamide

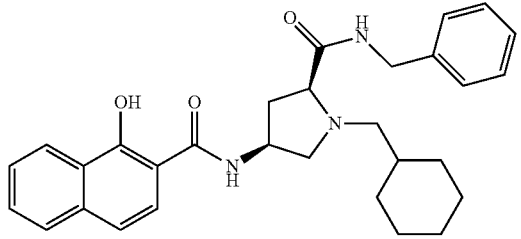 [SMILES: O=C(N[C@H]1C[C@@H](C(=O)NCc2ccccc2)N(CC2CCCCC2)C1)c1ccc2ccccc2c1O]

(2S,4S)-1-Cyclohexylmethyl-4-[(1-hydroxy-naphthalene-2-carbonyl)-amino]-pyrrolidine-2-carboxylic acid benzylamide was prepared from (2S,4S)-1-cyclohexylmethyl-4-[(1-hydroxy-naphthalene-2-carbonyl)-amino]-pyrrolidine-2-carboxylic acid methyl ester and benzylamine in an analogous manner to example 12. MS calcd. for $C_{30}H_{36}N_3O_3$ [(M+H)$^+$] 486.0, obsd. 486.4.

Example 15

1-Hydroxy-naphthalene-2-carboxylic acid [(3S,5S)-1-cyclohexylmethyl-5-(pyrrolidine-1-carbonyl)-pyrrolidin-3-yl]-amide

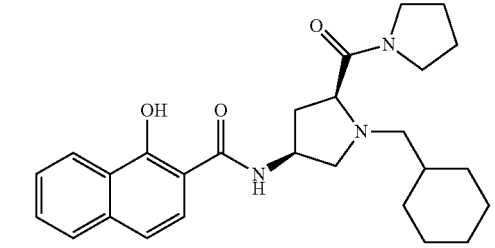 [SMILES: O=C(N[C@H]1C[C@@H](C(=O)N2CCCC2)N(CC2CCCCC2)C1)c1ccc2ccccc2c1O]

Hydroxy-naphthalene-2-carboxylic acid [(3S,5S)-1-cyclohexylmethyl-5-(pyrrolidine-1-carbonyl)-pyrrolidin-3-yl]-amide was prepared from (2S,4S)-1-cyclohexylmethyl-4-[(1-hydroxy-naphthalene-2-carbonyl)-amino]-pyrrolidine-2-carboxylic acid methyl ester and pyrrolidine in an analogous manner to example 12. MS calcd. for $C_{27}H_{36}N_3O_3$ [(M+H)$^4$] 450.0, obsd. 450.2.

Example 16

(2S,4S)-1-Cyclohexylmethyl-4-[(1-hydroxy-naphthalene-2-carbonyl)-amino]-pyrrolidine-2-carboxylic acid amide

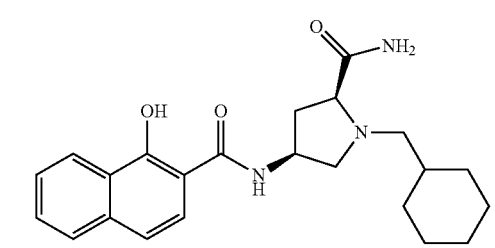 [SMILES: NC(=O)[C@@H]1C[C@H](NC(=O)c2ccc3ccccc3c2O)CN1CC1CCCCC1]

To a solution of (2S,4S)-1-cyclohexylmethyl-4-[(1-hydroxy-naphthalene-2-carbonyl)-amino]-pyrrolidine-2-carboxylic acid methyl ester (50 mg) in tetrahydrofuran (7 mL), aq. ammonium hydroxide (15 mL) was added in a seal tube and the mixture was heated for 24 hrs at 95° C. The reaction mixture was concentrated and the aqueous layer was extracted with diethyl ether, washed with brine, dried, concentrated and was purified by column chromatography to obtain (2S,4S)-1-cyclohexylmethyl-4-[(1-hydroxy-naphthalene-2-carbonyl)-amino]-pyrrolidine-2-carboxylic acid amide (8 mg, 16% yield) as a light brown solid. MS calcd. for $C_{23}H_{30}N_3O_3$ [(M+H)$^+$] 396, obsd. 396.

Example 17

(2S,4S)-1-Cyclohexylmethyl-4-[(1-hydroxy-naphthalene-2-carbonyl)-amino]-2-methyl-pyrrolidine-2-carboxylic acid methyl ester

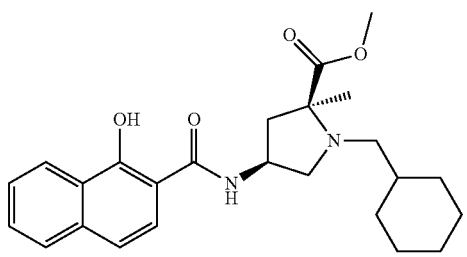 [SMILES: COC(=O)[C@]1(C)C[C@H](NC(=O)c2ccc3ccccc3c2O)CN1CC1CCCCC1]

(2S,4S)-1-Cyclohexylmethyl-4-[(1-hydroxy-naphthalene-2-carbonyl)-amino]-2-methyl-pyrrolidine-2-carboxylic acid methyl ester was prepared from (2S,4S)-4-amino-1-cyclohexylmethyl-2-methyl-pyrrolidine-2-carboxylic acid methyl ester and 1-hydroxy-naphthalene-2-carboxylic acid in an analogous manner to example 1. MS calcd. for $C_{25}H_{33}N_2O_4$ [(M+H)$^+$] 425, obsd. 425.

Example 18

(2R,4S)-1-Cyclohexylmethyl-4-[(1-hydroxy-naphthalene-2-carbonyl)-amino]-2-methyl-pyrrolidine-2-carboxylic acid methyl ester

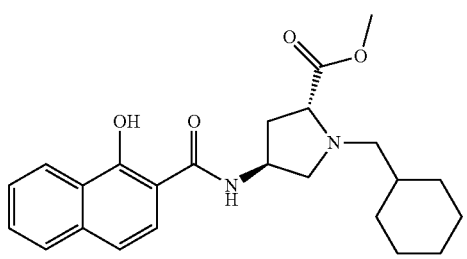 [SMILES: COC(=O)[C@H]1C[C@H](NC(=O)c2ccc3ccccc3c2O)CN1CC1CCCCC1]

(2R,4S)-1-Cyclohexylmethyl-4-[(1-hydroxy-naphthalene-2-carbonyl)-amino]-2-methyl-pyrrolidine-2-carboxylic acid methyl ester was prepared from (2R,4S)-4-amino-1-cyclohexylmethyl-pyrrolidine-2-carboxylic acid methyl ester and 1-hydroxy-naphthalene-2-carboxylic acid in an analogous manner to example 1. MS calcd. for $C_{24}H_{31}N_2O_4$ [(M+H)$^+$] 411, obsd. 411.

Example 19

(2S,4R)-1-Cyclohexylmethyl-4-[(1-hydroxy-naphthalene-2-carbonyl)-amino]-2-methyl-pyrrolidine-2-carboxylic acid methyl ester

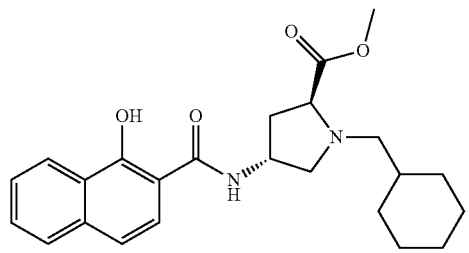 [SMILES: COC(=O)[C@@H]1C[C@@H](NC(=O)c2ccc3ccccc3c2O)CN1CC1CCCCC1]

(2S,4R)-1-Cyclohexylmethyl-4-[(1-hydroxy-naphthalene-2-carbonyl)-amino]-2-methyl-pyrrolidine-2-carboxylic acid methyl ester was prepared from (2S,4R)-4-amino-1-cyclohexylmethyl-pyrrolidine-2-carboxylic acid methyl ester and 1-hydroxy-naphthalene-2-carboxylic acid in an analogous manner to example 1. MS calcd. for $C_{24}H_{31}N_2O_4$ [(M+H)$^+$] 411, obsd. 411.

Example 20

(2S,4R)-1-Cyclohexylmethyl-4-[(1-hydroxy-naphthalene-2-carbonyl)-amino]-2-methyl-pyrrolidine-2-carboxylic acid ethyl ester

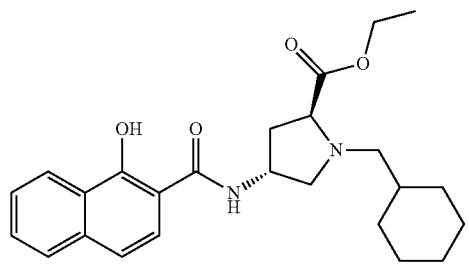 [SMILES: CCOC(=O)[C@@H]1C[C@@H](NC(=O)c2ccc3ccccc3c2O)CN1CC1CCCCC1]

(2S,4R)-1-Cyclohexylmethyl-4-[(1-hydroxy-naphthalene-2-carbonyl)-amino]-2-methyl-pyrrolidine-2-carboxylic acid ethyl ester was prepared from (2S,4R)-4-amino-1-cyclohexylmethyl-2-methyl-pyrrolidine-2-carboxylic acid methyl ester in an analogous manner to example 8. MS calcd. for $C_{25}H_{33}N_2O_4$ [(M+H)$^+$] 425, obsd. 425.

Example 21

(2S,4S)-4-[(1-Amino-naphthalene-2-carbonyl)-amino]-1-cyclohexylmethyl-pyrrolidine-2-carboxylic acid methyl ester

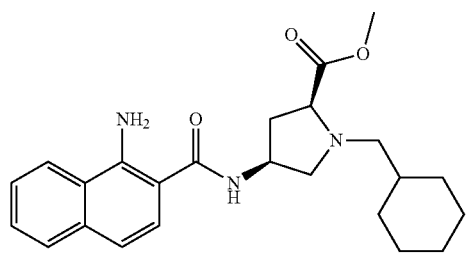 [SMILES: COC(=O)[C@@H]1C[C@H](NC(=O)c2ccc3ccccc3c2N)CN1CC1CCCCC1]

(2S,4S)-4-[(1-Amino-naphthalene-2-carbonyl)-amino]-1-cyclohexylmethyl-pyrrolidine-2-carboxylic acid methyl ester was prepared from (2S,4S)-4-amino-1-cyclohexylmethyl-pyrrolidine-2-carboxylic acid methyl ester and 1-amino-naphthalene-2-carboxylic acid in an analogous manner to example 1. MS calcd. for $C_{24}H_{32}N_3O_3$ [(M+H)$^+$] 410, obsd. 410.

Example 22

(2S,4S)-1-Cyclohexylmethyl-4-[(8-hydroxy-quinoline-7-carbonyl)-amino]-pyrrolidine-2-carboxylic acid ethyl ester

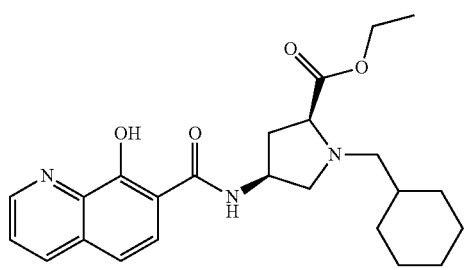 [SMILES: CCOC(=O)[C@@H]1C[C@H](NC(=O)c2ccc3cccnc3c2O)CN1CC1CCCCC1]

(2S,4S)-1-Cyclohexylmethyl-4-[(8-hydroxy-quinoline-7-carbonyl)-amino]-pyrrolidine-2-carboxylic acid ethyl ester was prepared from (2S,4S)-4-amino-1-cyclohexylmethyl-pyrrolidine-2-carboxylic acid methyl ester and 8-hydroxy-quinoline-7-carboxylic acid in an analogous manner to example 1. MS calcd. for $C_{24}H_{32}N_1O_4$ [(M+H)$^+$] 426, obsd. 426.

Example 23

(2S,4R)-1-Cyclohexylmethyl-4-[(1-hydroxy-naphthalene-2-carbonyl)-amino]-piperidine-2-carboxylic acid methyl ester

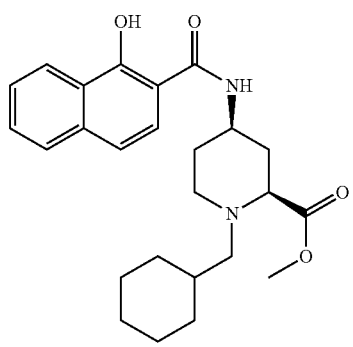 [SMILES: COC(=O)[C@@H]1C[C@H](NC(=O)c2ccc3ccccc3c2O)CCN1CC1CCCCC1]

(2S,4R)-1-Cyclohexylmethyl-4-[(1-hydroxy-naphthalene-2-carbonyl)-amino]piperidine-2-carboxylic acid methyl ester was prepared from (2S,4R)-4-amino-1-cyclohexylmethyl-piperidine-2-carboxylic acid methyl ester and 1-hydroxy-naphthalene-2-carboxylic acid in an analogous manner to example 1. MS calcd. for $C_{25}H_{33}N_2O_4$ [(M+H)$^+$] 425, obsd. 425.

Example 24

(2S,4R)-1-Cyclohexylmethyl-4-[(1-hydroxy-naphthalene-2-carbonyl)-amino]-piperidine-2-carboxylic acid ethyl ester

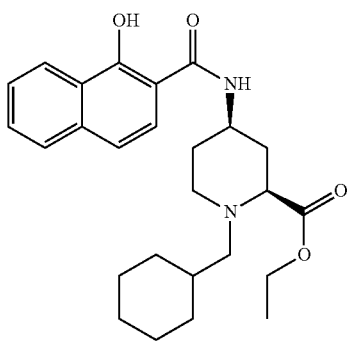 [SMILES: CCOC(=O)[C@@H]1C[C@H](NC(=O)c2ccc3ccccc3c2O)CCN1CC1CCCCC1]

(2S,4R)-1-Cyclohexylmethyl-4-[(1-hydroxy-naphthalene-2-carbonyl)-amino]piperidine-2-carboxylic acid ethyl ester was prepared from (2S,4R)-1-Cyclohexylmethyl-4-[(1-hydroxy-naphthalene-2-carbonyl)-amino]-piperidine-2-carboxylic acid methyl ester in an analogous manner to example 8. MS calcd. for $C_{26}H_{35}N_2O_4$ [(M+H)$^+$] 439, obsd. 439.

Example 25

(2S,4R)-1-Cyclohexylmethyl-4-[(1-hydroxy-naphthalene-2-carbonyl)-amino]-piperidine-2-carboxylic acid ethylamide

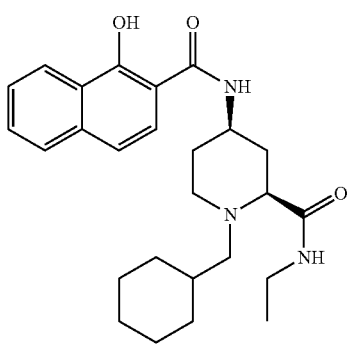 [SMILES: CCNC(=O)[C@@H]1C[C@H](NC(=O)c2ccc3ccccc3c2O)CCN1CC1CCCCC1]

(2S,4R)-1-Cyclohexylmethyl-4-[(1-hydroxy-naphthalene-2-carbonyl)-amino]-piperidine-2-carboxylic acid ethyl ester was prepared from (2S,4R)-1-Cyclohexylmethyl-4-[(1-hydroxy-naphthalene-2-carbonyl)-amino]-piperidine-2-carboxylic acid methyl ester in an analogous manner to example 10. MS calcd. for $C_{26}H_{36}N_3O_3$ [(1\441)$^\pm$] 438, obsd. 438.

Example 26

1-Hydroxy-naphthalene-2-carboxylic acid ((3S,5S)-1-cyclohexylmethyl-5-oxazol-2-yl-pyrrolidin-3-yl)-amide

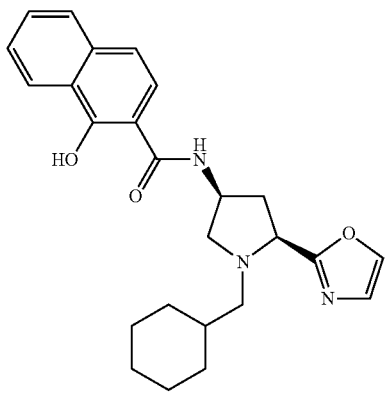 [SMILES: O=C(N[C@H]1C[C@@H](c2ncco2)N(CC2CCCCC2)C1)c1ccc2ccccc2c1O]

Step 1: Preparation of (2S,4S)-4-[(1-hydroxy-naphthalene-2-carbonyl)-amino]-2-oxazol-2-yl-pyrrolidine-1-carboxylic acid benzyl ester

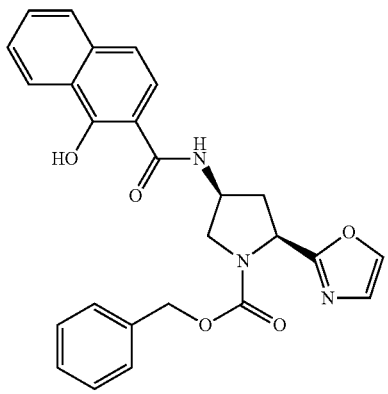 [SMILES: O=C(N[C@H]1C[C@@H](c2ncco2)N(C(=O)OCc2ccccc2)C1)c1ccc2ccccc2c1O]

(2S,4S)-4-[(1-hydroxy-naphthalene-2-carbonyl)-amino]-2-oxazol-2-yl-pyrrolidine-1-carboxylic acid benzyl ester was prepared from (2S,4S)-4-amino-2-oxazol-2-yl-pyrrolidine-1-carboxylic acid benzyl ester and 1-hydroxy-naphthalene-2-carboxylic acid in an analogous manner to example 1. MS calcd. for $C_{26}H_{24}N_3O_5$ [(M+H)$^+$] 458, obsd. 458.

Step 2: Preparation of 1-hydroxy-naphthalene-2-carboxylic acid ((3S,5S)-5-oxazol-2-yl-pyrrolidin-3-yl)-amide

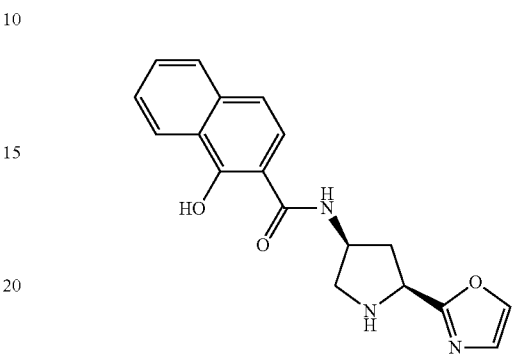

To a solution of (2S,4S)-4-[(1-hydroxy-naphthalene-2-carbonyl)-amino]-2-oxazol-2-yl-pyrrolidine-1-carboxylic acid benzyl ester (30 mg, 0.06 mmol) in methanol (2 mL) was added 20% Pd(OH)$_2$ (20 mg) and the mixture was stirred at room temp. for 16 h. with a balloon containing H$_2$ gas. The reaction mixture was then filtered and concentrated under reduced pressure to give 1-hydroxy-naphthalene-2-carboxylic acid ((3S,5S)-5-oxazol-2-yl-pyrrolidin-3-yl)-amide (15 mg) as a light brown liquid. MS calcd. for $C_{18}H_{18}N_3O_3$[(M+H)$^+$] 324, obsd. 324.

Step 3: Preparation of 1-hydroxy-naphthalene-2-carboxylic acid ((3S,5S)-1-cyclohexylmethyl-5-oxazol-2-yl-pyrrolidin-3-yl)-amide

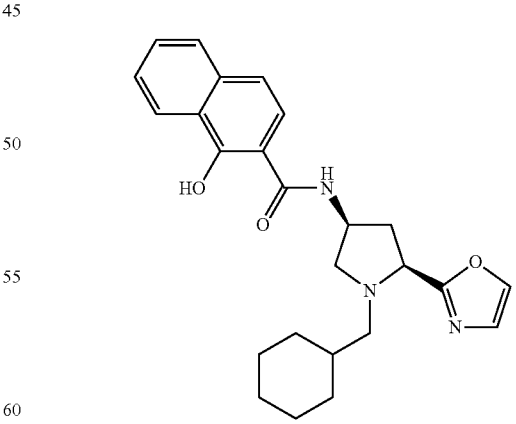

Hydroxy-naphthalene-2-carboxylic acid ((3S,5S)-1-cyclohexylmethyl-5-oxazol-2-yl-pyrrolidin-3-yl)-amide was prepared from 1-hydroxy-naphthalene-2-carboxylic acid ((3S,5S)-5-oxazol-2-yl-pyrrolidin-3-yl)-amide and cyclohexanecarbaldehyde in a similar fashion as the synthesis of (2S,4S)-4-azido-1-cyclohexylmethyl-pyrrolidine-2-carboxylic acid methyl ester. MS calcd. for $C_{25}H_{30}N_3O_3[(M+H)^+]$ 420, obsd. 419.8.

Example 27

1-Hydroxy-naphthalene-2-carboxylic acid [(3S,5S)-1-cyclohexylmethyl-5-(5-methyl-oxazol-2-yl)-pyrrolidin-3-yl]-amide

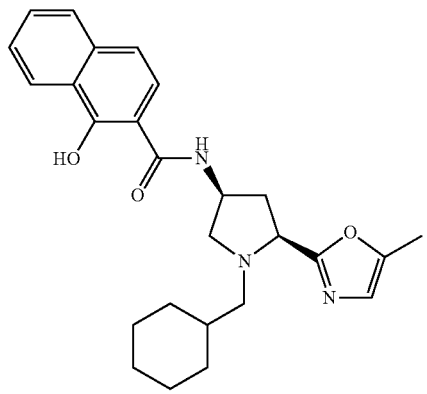 [SMILES: Cc1cnc([C@@H]2C[C@H](NC(=O)c3ccc4ccccc4c3O)CN2CC2CCCCC2)o1]

Step 1: Preparation of (2S,4S)-4-[(1-hydroxy-naphthalene-2-carbonyl)-amino]-2-(5-methyl-oxazol-2-yl)-pyrrolidine-1-carboxylic acid benzyl ester

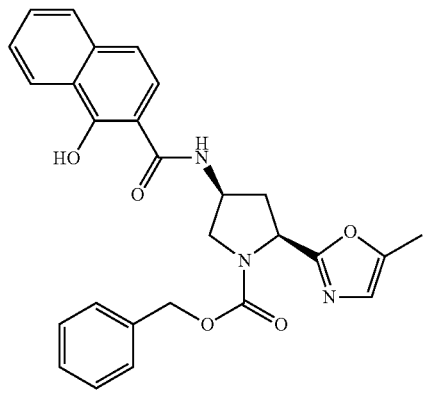 [SMILES: Cc1cnc([C@@H]2C[C@H](NC(=O)c3ccc4ccccc4c3O)CN2C(=O)OCc2ccccc2)o1]

(2S,4S)-4-[(1-hydroxy-naphthalene-2-carbonyl)-amino]-2-(5-methyl-oxazol-2-yl)-pyrrolidine-1-carboxylic acid benzyl ester was prepared from (2S,4S)-4-amino-2-(5-methyl-oxazol-2-yl)-pyrrolidine-1-carboxylic acid benzyl ester and 1-hydroxy-naphthalene-2-carboxylic acid in an analogous manner to example 1. MS calcd. for $C_{27}H_{26}N_3O_5 [(M+H)^+]$ 472, obsd. 472.

Step 2: Preparation of 1-hydroxy-naphthalene-2-carboxylic acid [(3S,5S)-5-(5-methyl-oxazol-2-yl)-pyrrolidin-3-yl]-amide

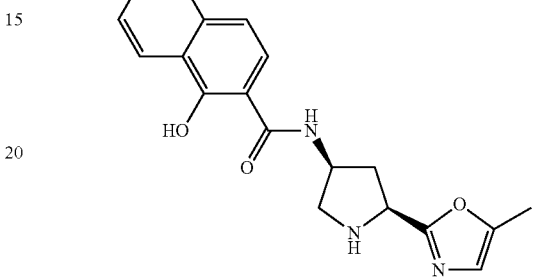

1-hydroxy-naphthalene-2-carboxylic acid [(3S,5S)-5-(5-methyl-oxazol-2-yl)-pyrrolidin-3-yl]-amide was prepared from (2S,4S)-4-[(1-hydroxy-naphthalene-2-carbonyl)-amino]-2-(5-methyl-oxazol-2-yl)-pyrrolidine-1-carboxylic acid benzyl ester in an analogous manner to example 26. MS calcd. for $C_{19}H_{20}N_3O_3 [(M+H)^+]$ 338, obsd. 338.

Step 3: Preparation of 1-hydroxy-naphthalene-2-carboxylic acid [(3S,5S)-1-cyclohexylmethyl-5-(5-methyl-oxazol-2-yl)-pyrrolidin-3-yl]-amide

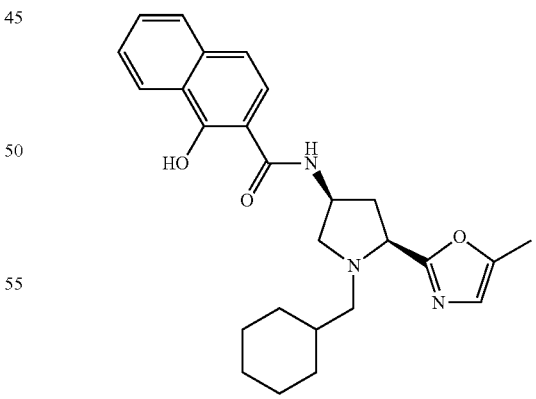

1-hydroxy-naphthalene-2-carboxylic acid [(3S,5S)-1-cyclohexylmethyl-5-(5-methyl-oxazol-2-yl)-pyrrolidin-3-yl]-amide was prepared from 1-hydroxy-naphthalene-2-carboxylic acid [(3S,5S)-5-(5-methyl-oxazol-2-yl)-pyrrolidin- 3-yl]-amide in an analogous manner to example 26. MS calcd. for $C_{26}H_{32}N_3O_3$ [(M+H)$^+$] 434, obsd. 434.

Example 28

1-Hydroxy-naphthalene-2-carboxylic acid [(3S,5S)-1-cyclohexylmethyl-5-(5-phenyl-oxazol-2-yl)-pyrrolidin-3-yl]-amide

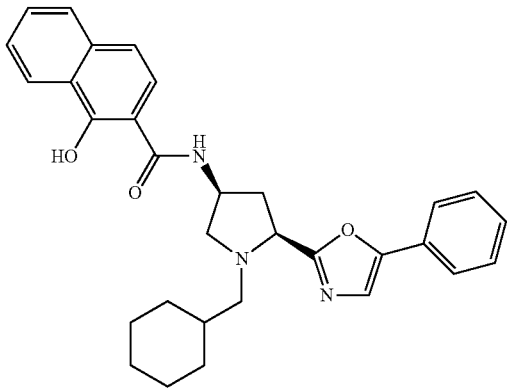 [SMILES: O=C(N[C@H]1C[C@@H](c2ncc(-c3ccccc3)o2)N(CC2CCCCC2)C1)c1ccc2ccccc2c1O]

Step 1: Preparation of (2S,4S)-4-[(1-hydroxy-naphthalene-2-carbonyl)-amino]-2-(5-phenyl-oxazol-2-yl)-pyrrolidine-1-carboxylic acid benzyl ester

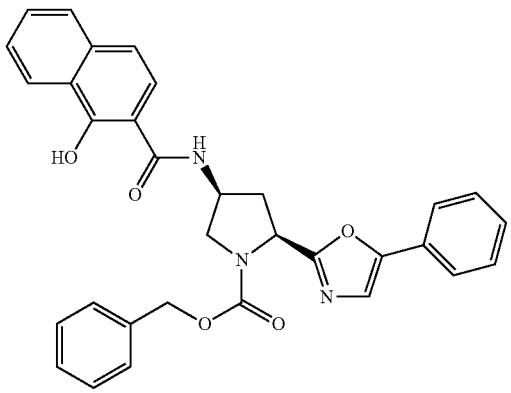 [SMILES: O=C(N[C@H]1C[C@@H](c2ncc(-c3ccccc3)o2)N(C(=O)OCc2ccccc2)C1)c1ccc2ccccc2c1O]

(2S,4S)-4-[(1-hydroxy-naphthalene-2-carbonyl)-amino]-2-(5-phenyl-oxazol-2-yl)-pyrrolidine-1-carboxylic acid benzyl ester was prepared from (2S,4S)-4-amino-2-(5-phenyl-oxazol-2-yl)-pyrrolidine-1-carboxylic acid benzyl ester and 1-hydroxy-naphthalene-2-carboxylic acid in an analogous manner to example 1. MS calcd. for $C_{32}H_{28}N_3O_5$ [(M+H)$^+$] 534, obsd. 534.

Step 2: Preparation of 1-hydroxy-naphthalene-2-carboxylic acid [(3S,5S)-5-(5-phenyl-oxazol-2-yl)-pyrrolidin-3-yl]-amide

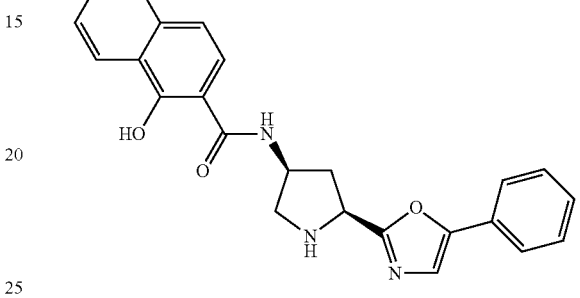

1-hydroxy-naphthalene-2-carboxylic acid [(3S,5S)-5-(5-phenyl-oxazol-2-yl)-pyrrolidin-3-yl]-amide was prepared from (2S,4S)-4-[(1-hydroxy-naphthalene-2-carbonyl)-amino]-2-(5-phenyl-oxazol-2-yl)-pyrrolidine-1-carboxylic acid benzyl ester in an analogous manner to example 26. MS calcd. for $C_{24}H_{22}N_3O_3$ [(M+H)$^+$] 400, obsd. 400.

Step 3: Preparation of 1-hydroxy-naphthalene-2-carboxylic acid [(3S,5S)-1-cyclohexylmethyl-5-(5-phenyl-oxazol-2-yl)-pyrrolidin-3-yl]-amide

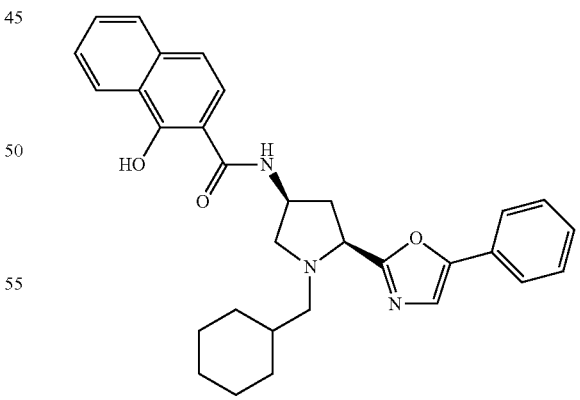

1-Hydroxy-naphthalene-2-carboxylic acid [(3S,5S)-1-cyclohexylmethyl-5-(5-phenyl-oxazol-2-yl)-pyrrolidin-3-yl]-amide was prepared from 1-hydroxy-naphthalene-2-carboxylic acid [(3S,5S)-5-(5-phenyl-oxazol-2-yl)-pyrrolidin- 3-yl]-amide in an analogous manner to example 26. MS calcd. for $C_{31}H_{34}N_3O_3$ [(M+H)$^+$] 496, obsd. 496.

Example 29

1-Hydroxy-naphthalene-2-carboxylic acid ((3S,5S)-5-benzooxazol-2-yl-1-cyclohexylmethyl-pyrrolidin-3-yl)-amide

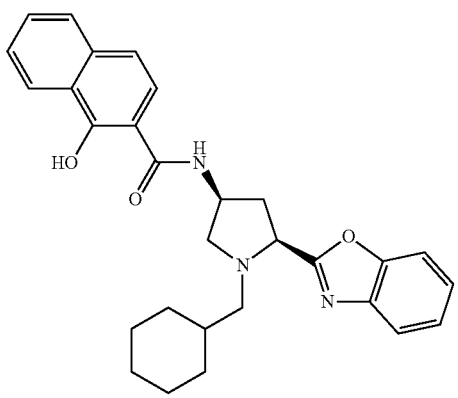 [SMILES: O=C(N[C@H]1C[C@@H](c2nc3ccccc3o2)N(CC2CCCCC2)C1)c1ccc2ccccc2c1O]

Step 1: Preparation of (2S,4S)-2-benzooxazol-2-yl-4-[(1-hydroxy-naphthalene-2-carbonyl)-amino]-pyrrolidine-1-carboxylic acid benzyl ester

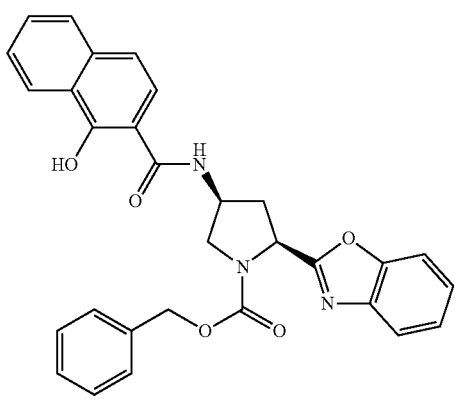 [SMILES: O=C(N[C@H]1C[C@@H](c2nc3ccccc3o2)N(C(=O)OCc2ccccc2)C1)c1ccc2ccccc2c1O]

(2S,4S)-2-benzooxazol-2-yl-4-[(1-hydroxy-naphthalene-2-carbonyl)-amino]-pyrrolidine-1-carboxylic acid benzyl ester was prepared from (2S,4S)-4-amino-2-benzooxazol-2-yl-pyrrolidine-1-carboxylic acid benzyl ester and 1-hydroxy-naphthalene-2-carboxylic acid in an analogous manner to example 1. MS calcd. for $C_{30}H_{26}N_3O_5$[(M+H)$^+$] 508, obsd. 508.

Step 2: Preparation of 1-hydroxy-naphthalene-2-carboxylic acid ((3S,5S)-5-benzooxazol-2-yl-pyrrolidin-3-yl)-amide

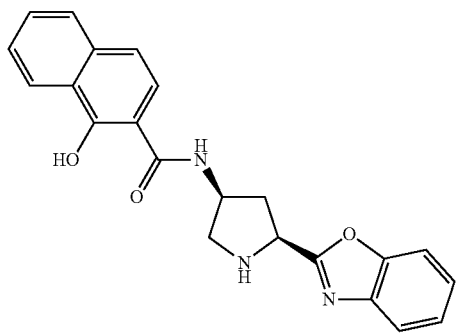 [SMILES: O=C(N[C@@H]1CN[C@H](c2nc3ccccc3o2)C1)c1ccc2ccccc2c1O]

1-hydroxy-naphthalene-2-carboxylic acid ((3S,5S)-5-benzooxazol-2-yl-pyrrolidin-3-yl)-amide was prepared from (2S,4S)-2-benzooxazol-2-yl-4-[(1-hydroxy-naphthalene-2-carbonyl)-amino]-pyrrolidine-1-carboxylic acid benzyl ester in an analogous manner to example 26. MS calcd. for $C_{22}H_{20}N_3O_3$ [(M+H)$^+$] 374, obsd. 374.

Step 3: Preparation of 1-hydroxy-naphthalene-2-carboxylic acid ((3S,5S)-5-benzooxazol-2-yl-1-cyclohexylmethyl-pyrrolidin-3-yl)-amide

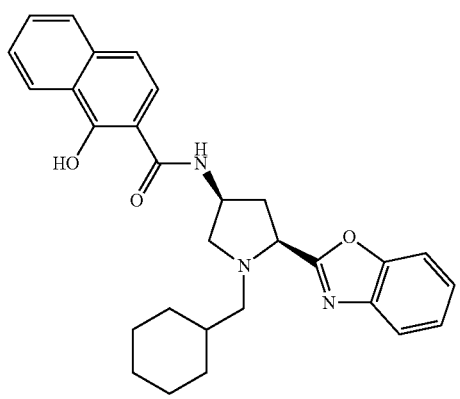 [SMILES: O=C(N[C@H]1C[C@@H](c2nc3ccccc3o2)N(CC2CCCCC2)C1)c1ccc2ccccc2c1O]

1-hydroxy-naphthalene-2-carboxylic acid ((3S,5S)-5-benzooxazol-2-yl-1-cyclohexylmethyl-pyrrolidin-3-yl)-amide was prepared from 1-hydroxy-naphthalene-2-carboxylic acid ((3S,5S)-5-benzooxazol-2-yl-pyrrolidin-3-yl)-amide in an analogous manner to example 26. MS calcd. for $C_{29}H_{32}N_3O_3$ [(M+H)$^+$] 470, obsd. 470.

Biological Examples

Determination of compounds HCV GT1b inhibitory replicon activity using the replicon luciferase reporter assay The 2209-23 cell line was developed at Roche by stable transfection of the hepatoma cell line Huh-7 with a GT-1b Con1 subgenomic bicistronic replicon as previously described. Subgenomic replicon cell line was established in cured Huh7 cells, obtained from R. Bartenschlager (J Virol. 2003 March; 77 (5):3007-19) The GT-1a H77 subgenomic replicon vector pRLuc H77 1b 75 S/I, was created by replacing the nonstructural region of the GT-1b Con1 subgenomic replicon by the one of the H77 strain, except for the first 75 amino acids of the NS3 protein that are from GT-1b Con1 strain. (1 Virol. 2001 77:5352-59) The GT-1a pRLuc H77 1b 75 S/I subgenomic replicon cell line was established in cured Huh7 cells, obtained from R. Bartenschlager. (J Virol. 2003 March; 77 (5):3007-19)

All the subgenomic replicon cell lines were cultured in Dulbecco's Modified Eagle Medium (DMEM-Glutamax™-I; Invitrogen Cat #10569-010). The medium was supplemented with 10% Fetal Bovine Serum (Invitrogen Cat #10082-147), 1% penicillin/streptomycin (Mediatech Cat #30-002-CI) and 500 µg/ml of G418 (Mediatech Cat #30-234-CI). Cells were maintained at 37° C. in a humidified 5% $CO_2$ atmosphere.

2209-23 cells were plated at a cell density of 5000 cells per well in 96 well plates (Becton Dickinson, Cat #35 3296). Cells were plated in 90 µl of Dulbecco's Modified Eagle Medium (DMEM-Glutamax™-I), (Invitrogen Cat #10569-010) medium was supplemented with 5% Fetal Bovine Serum (Invitrogen Cat #10082-147), 1% penicillin/streptomycin (Mediatech Cat #30-002-CI). The pRluc H77 1b 75 S/I cells were plated in 96-well plate at 3000 cells/well in DMEM-Glutamax™-I containing 5% FBS and 1% penicillin/streptomycin in 90 µl final volume. Cells were allowed to equilibrate for 24 hours at 37° C. and 5% CO2 at which time compounds were added. Compounds (or medium as a control) were added 24 hours post-plating in 3 fold dilutions at a final DMSO concentration of 1% in 10 µl volume. Renilla luciferase reporter signal was read 72 hours after addition of compounds using the Renilla Luciferase Assay System (Promega, cat # E2820). EC50 values were defined as the compound concentration at which a 50% reduction in the levels of renilla luciferase reporter was observed as compared to control samples in the absence of compound and was determined by non-linear fitting of compound dose-response data. The EC50 was approximated if maximum percentage inhibition was less than 90% and more than 70%.

Determination of compounds cytotoxicity using the HCV GT1b replicon cell line measuring WST1.

2209-23 cells were plated at a cell density of 5000 cells per well in clear flat-bottom 96 well plate (Becton Dickinson, Cat #35 3075) for cell viability studies. The WST-1 cell proliferation assay (Roche Diagnostic, Cat#11644807001) was used to determine cell viability. Assay plates were set up in the same format as in the replicon assay. After 3 days of compound incubation 10 µl of WST-1 reagent was added to each well for 2 hours at 37° C. and 5% $CO_2$, following manufacturer's instructions. Absorption reading at 450 nm (reference filter at 650 nm) was determined using MRX Revelation microtiter plate reader (Lab System). $CC_{50}$ values were defined as the compound concentration required for reducing cell viability by 50% as compared to the untreated control in absence of compound and was determined by non-linear fitting of compound dose-response data. Representative assay data can be found in Table II below:

TABLE II

| Compound # | GT-1a - $EC_{50}$ (nM) HCV, GT1b, $IC_{50}$ (□M) |
|---|---|
| I-1 | 0.047 |
| I-2 | 0.079 |
| I-3 | 0.051 |
| I-4 | 0.029 |
| I-5 | 0.052 |
| I-6 | 0.055 |
| I-7 | 0.070 |
| I-8 | 0.086 |
| I-9 | 0.114 |
| I-10 | 0.120 |
| I-11 | 0.121 |

TABLE II-continued

| Compound # | GT-1a - $EC_{50}$ (nM) HCV, GT1b, $IC_{50}$ (□M) |
|---|---|
| I-12 | 0.129 |
| I-13 | 0.163 |
| I-14 | 0.184 |
| I-15 | 0.187 |
| I-16 | 0.205 |
| I-17 | 0.219 |
| I-18 | 0.221 |
| I-19 | 0.223 |
| I-20 | 0.233 |
| I-21 | 0.247 |
| I-22 | 0.299 |
| I-23 | 0.336 |
| I-24 | 0.367 |
| I-25 | 0.509 |
| I-26 | 0.64 |
| I-27 | 0.659 |
| I-28 | 0.793 |
| I-29 | 0.826 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:
1. A compound of Formula I

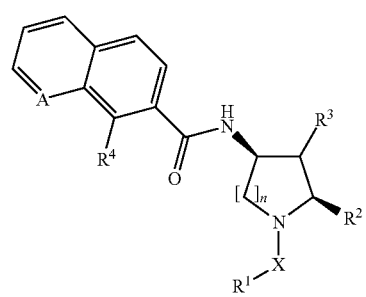

wherein:
A is CH or N;
n is 1 or 2;
$R^1$ is lower alkyl, cycloalkyl, phenyl, or heterocycloalkyl;
$R^2$ is —C(=O)O$R^{2'}$, —C(=O)N($R^{2'}$)$_2$, monocyclic or bicyclic heteroaryl, optionally substituted with one or more $R^{2'}$;
each $R^{2'}$ is independently H, lower alkyl or heterocycloalkyl;
$R^3$ is H or lower alkyl;
$R^4$ is hydroxyl or amino; and
X is $CH_2$ or C(=O);
or a pharmaceutically acceptable salt thereof.

2. The compound of claim 1, wherein $R^3$ is H and X is $CH_2$.

3. The compound of claim 2, wherein n is 2.

4. The compound of claim 2, wherein n is 1.

5. The compound of claim 4, wherein $R^2$ is —C(=O)N$(R^{2'})_2$.

6. The compound of claim 4, wherein $R^2$ is monocyclic or bicyclic heteroaryl, optionally substituted with one or more $R^{2'}$.

7. The compound of claim 4, wherein $R^2$ is —C(=O)O$R^{2'}$.

8. The compound of claim 7, wherein $R^{2'}$ is lower alkyl.

9. The compound of claim 8, wherein $R^1$ is lower alkyl or cycloalkyl.

10. The compound of claim 9, wherein $R^1$ is cyclohexyl.

11. A compound selected from the group consisting of:
- (2S,4S)-1-Cyclohexylmethyl-4-[(1-hydroxy-naphthalene-2-carbonyl)-amino]-pyrrolidine-2-carboxylic acid tert-butyl ester;
- (2S,4S)-1-(3,3-Dimethyl-butyl)-4-[(1-hydroxy-naphthalene-2-carbonyl)-amino]-pyrrolidine-2-carboxylic acid methyl ester;
- (2S,4R)-1-Cyclohexylmethyl-4-[(1-hydroxy-naphthalene-2-carbonyl)-amino]-piperidine-2-carboxylic acid ethyl ester;
- (2S,4S)-1-Cyclohexylmethyl-4-[(1-hydroxy-naphthalene-2-carbonyl)-amino]-pyrrolidine-2-carboxylic acid ethyl ester;
- 1-Hydroxy-naphthalene-2-carboxylic acid ((3S,5S)-5-benzooxazol-2-yl-1-cyclohexylmethyl-pyrrolidin-3-yl)-amide;
- (2S,4R)-1-Cyclohexylmethyl-4-[(1-hydroxy-naphthalene-2-carbonyl)-amino]-piperidine-2-carboxylic acid methyl ester;
- 1-Hydroxy-naphthalene-2-carboxylic acid [(3S,5S)-1-cyclohexylmethyl-5-(5-methyl-oxazol-2-yl)-pyrrolidin-3-yl]-amide;
- 1-Hydroxy-naphthalene-2-carboxylic acid [(3S,5S)-1-cyclohexylmethyl-5-(5-phenyl-oxazol-2-yl)-pyrrolidin-3-yl]-amide;
- 1-Hydroxy-naphthalene-2-carboxylic acid ((3S,5S)-1-cyclohexylmethyl-5-oxazol-2-yl-pyrrolidin-3-yl)-amide;
- (2S,4S)-1-Cyclohexylmethyl-4-[(1-hydroxy-naphthalene-2-carbonyl)-amino]-pyrrolidine-2-carboxylic acid methyl ester;
- (2S,4S)-1-Benzyl-4-[(1-hydroxy-naphthalene-2-carbonyl)-amino]-pyrrolidine-2-carboxylic acid methyl ester;
- (2S,4S)-1-Cyclopentylmethyl-4-[(1-hydroxy-naphthalene-2-carbonyl)-amino]-pyrrolidine-2-carboxylic acid ethyl ester;
- (2S,4S)-1-Cyclohexylmethyl-4-[(1-hydroxy-naphthalene-2-carbonyl)-amino]-pyrrolidine-2-carboxylic acid benzylamide;
- (2S,4S)-1-Cyclohexanecarbonyl-4-[(1-hydroxy-naphthalene-2-carbonyl)-amino]-pyrrolidine-2-carboxylic acid ethyl ester;
- (2S,4S)-1-Cyclohexylmethyl-4-[(1-hydroxy-naphthalene-2-carbonyl)-amino]-pyrrolidine-2-carboxylic acid isopropylamide;
- (2S,4S)-1-Cyclohexylmethyl-4-[(1-hydroxy-naphthalene-2-carbonyl)-amino]-pyrrolidine-2-carboxylic acid propylamide;
- (2S,4S)-1-Cyclobutylmethyl-4-[(1-hydroxy-naphthalene-2-carbonyl)-amino]-pyrrolidine-2-carboxylic acid ethyl ester;
- (2S,4S)-1-Cyclohexylmethyl-4-[(1-hydroxy-naphthalene-2-carbonyl)-amino]-pyrrolidine-2-carboxylic acid ethylamide;
- (2S,4R)-1-Cyclohexylmethyl-4-[(1-hydroxy-naphthalene-2-carbonyl)-amino]-piperidine-2-carboxylic acid ethylamide;
- (2R,4S)-1-Cyclohexylmethyl-4-[(1-hydroxy-naphthalene-2-carbonyl)-amino]-pyrrolidine-2-carboxylic acid methyl ester;
- (2S,4S)-1-Cyclohexylmethyl-4-[(1-hydroxy-naphthalene-2-carbonyl)-amino]-2-methyl-pyrrolidine-2-carboxylic acid methyl ester;
- (2S,4S)-4-[(1-Hydroxy-naphthalene-2-carbonyl)-amino]-1-isobutyl-pyrrolidine-2-carboxylic acid ethyl ester;
- (2S,4S)-4-[(1-Amino-naphthalene-2-carbonyl)-amino]-1-cyclohexylmethyl-pyrrolidine-2-carboxylic acid methyl ester;
- (2S,4S)-1-Cyclohexylmethyl-4-[(8-hydroxy-quinoline-7-carbonyl)-amino]-pyrrolidine-2-carboxylic acid ethyl ester;
- (2S,4S)-1-Cyclohexylmethyl-4-[(1-hydroxy-naphthalene-2-carbonyl)-amino]-pyrrolidine-2-carboxylic acid amide;
- 1-Hydroxy-naphthalene-2-carboxylic acid [(3S,5S)-1-cyclohexylmethyl-5-(pyrrolidine-1-carbonyl)-pyrrolidin-3-yl]-amide;
- (2S,4R)-1-Benzyl-4-[(1-hydroxy-naphthalene-2-carbonyl)-amino]-pyrrolidine-2-carboxylic acid ethyl ester;
- (2S,4R)-1-Cyclohexylmethyl-4-[(1-hydroxy-naphthalene-2-carbonyl)-amino]-pyrrolidine-2-carboxylic acid methyl ester; and
- 1-Hydroxy-naphthalene-2-carboxylic acid [(3S,5S)-5-(azetidine-1-carbonyl)-1-cyclohexylmethyl-pyrrolidin-3-yl]-amide.

12. A pharmaceutical composition comprising a compound of claim 1 and a pharmaceutically acceptable excipient.

13. A pharmaceutical composition comprising a compound of claim 2 and a pharmaceutically acceptable excipient.

14. A pharmaceutical composition comprising a compound of claim 3 and a pharmaceutically acceptable excipient.

15. A pharmaceutical composition comprising a compound of claim 4 and a pharmaceutically acceptable excipient.

16. A pharmaceutical composition comprising a compound of claim 5 and a pharmaceutically acceptable excipient.

17. A pharmaceutical composition comprising a compound of claim 6 and a pharmaceutically acceptable excipient.

18. A pharmaceutical composition comprising a compound of claim 7 and a pharmaceutically acceptable excipient.

19. A pharmaceutical composition comprising a compound of claim 8 and a pharmaceutically acceptable excipient.

20. A pharmaceutical composition comprising a compound of claim 9 and a pharmaceutically acceptable excipient.

21. A pharmaceutical composition comprising a compound of claim 10 and a pharmaceutically acceptable excipient.

22. A pharmaceutical composition comprising a compound of claim 11 and a pharmaceutically acceptable excipient.

\* \* \* \* \*